United States Patent
Carotta et al.

(10) Patent No.: US 12,065,427 B2
(45) Date of Patent: Aug. 20, 2024

(54) HETEROCYCLIC COMPOUNDS CAPABLE OF ACTIVATING STING

(71) Applicant: BOEHRINGER INGELHEIM INTERNATIONAL GMBH, Ingelheim am Rhein (DE)

(72) Inventors: Sebastian Carotta, Vienna (AT); Georg Dahmann, Biberach (DE); Cédrickx Godbout, Attenweiler (DE); Sandra Ruth Handschuh, Biberach an der Riss (DE); Herbert Nar, Ochsenhausen (DE); Thorsten Oost, Biberach an der Riss (DE); Ulrich Reiser, Vienna (AT); Matthias Treu, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/730,395

(22) Filed: Apr. 27, 2022

(65) Prior Publication Data

US 2022/0388986 A1    Dec. 8, 2022

(30) Foreign Application Priority Data

Apr. 29, 2021    (EP) .................................... 21171155

(51) Int. Cl.
  *C07D 401/14*    (2006.01)
  *A61K 45/06*    (2006.01)
(52) U.S. Cl.
  CPC ............ *C07D 401/14* (2013.01); *A61K 45/06* (2013.01)
(58) Field of Classification Search
  CPC .............................. A61P 31/00; C07D 405/14
  See application file for complete search history.

(56) References Cited

U.S. PATENT DOCUMENTS

| | | | |
|---|---|---|---|
| 11,130,773 B2 | 9/2021 | Hanada et al. | |
| 2020/0172534 A1 | 6/2020 | Roush et al. | |
| 2021/0087180 A1* | 3/2021 | Patman | A61P 35/00 |
| 2021/0355105 A1 | 11/2021 | Liu et al. | |
| 2022/0119379 A1* | 4/2022 | Li | A61P 29/00 |
| 2022/0389025 A1* | 12/2022 | Duan | C07D 519/00 |

FOREIGN PATENT DOCUMENTS

| | | |
|---|---|---|
| EP | 3868764 A1 | 8/2021 |
| WO | 2013134243 A1 | 9/2013 |
| WO | 2014151616 A1 | 9/2014 |
| WO | 2019234220 A1 | 12/2019 |
| WO | 2020010092 A1 | 1/2020 |
| WO | 2020073949 A1 | 4/2020 |
| WO | 2020075790 A1 | 4/2020 |
| WO | 2021064137 A2 | 4/2021 |
| WO | 2021143823 A1 | 7/2021 |
| WO | 2021174165 A1 | 9/2021 |

OTHER PUBLICATIONS

Ablasser et al., ""cGAS produces a 2'-5'-linked cyclic dinucleotide second messenger that activates STING, Nature, 2013, vol. 498, No. 7454, pp. 380-384.
Chen et al., "Agonist of stimulator of interferon genes as antitumor agents: a patent review (2008-2020)", Expert Opinion on Therapeutic Patents, 2021, vol. 31, No. 6, pp. 1-22.
Corrales et al., "Direct Activation of STING in the Tumor Microenvironment Leads to Potent and Systemic Tumor Regression and Immunity", Cell Reports, 2015, vol. 11, No. 7, pp. 1018-1030.
Deng et al., "STING-Dependent Cytosolic DNA Sensing Promotes Radiation-Induced Type I Interferon-Dependent Antitumor Immunity in Immunogenic Tumors", Immunity, 2014, vol. 41, No. 5, pp. 843-852.
Liu et al., "Phosphorylation of innate immune adaptor proteins MAVS, STING, and TRIF induces IRF3 activation", Science, 2015, vol. 347, No. 6227, pp. aaa2630 1-17.
Sistigu et al., "Cancer cell-autonomous contribution of type I interferon signaling to the efficacy of chemotherapy", Nature Medicine, 2014, vol. 20, No. 11, pp. 1301-1309.
Woo et al., "STING-Dependent Cytosolic DNA Sensing Mediates Innate Immune Recognition of Immunogenic Tumors", Immunity, 2014, vol. 41, No. 5, pp. 830-842.
Wu et al., "Agonists and inhibitors of the STING pathway: Potential agents for immunotherapy", Medicinal Research Reviews, 2020, vol. 40, No. 3, pp. 1117-1141.
Yi et al., "Single Nucleotide Polymorphisms of Human STING Can Affect Innate Immune Response to Cyclic Dinucleotides", Plos One, 2013, vol. 8, No. 10, pp. e77846 1-16.

(Continued)

*Primary Examiner* — Jeffrey S Lundgren
*Assistant Examiner* — Eric Tran
(74) *Attorney, Agent, or Firm* — Philip I. Datlow

(57) ABSTRACT

The present invention relates to heterocyclic compounds of formula (I) capable of activating STING (Stimulator of Interferon Genes).

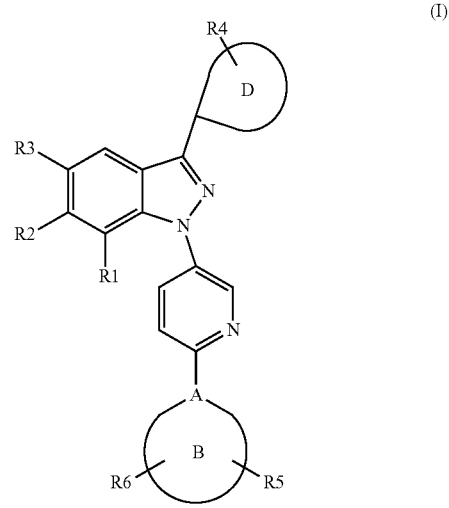

40 Claims, No Drawings

(56) References Cited

OTHER PUBLICATIONS

Zitvogel et al., "Type I interferons in anticancer immunity", Nature Reviews Immunology, 2015, vol. 15, No. 7, pp. 405-414.
International Search Report an Written Opinion for corresponding application, PCT/EP2022/061379, date of mailing Aug. 2, 2022.
English abstract for WO2021143823 dated Jul. 22, 2021.
Ding Chunyong et al., "Small molecules targeting the innate immune cGAS-STING-TBK1 signaling pathway", Acta Pharmaceutica Sinica B, Dec. 1, 2020, vol. 10, No. 12, pp. 2272-2298.
Klotz et al., "Type I interferons in the pathogenesis and treatment of canine diseases", Veterinary Immunology and Immunopathology, vol. 191, 2017, pp. 80-93.
U.S. Appl. No. 18/383,135, filed Oct. 24, 2023. The cited pending U.S. application is stored in the USPTO IFW system (MPEP 609.04(a)(II)(C)).
U.S. Appl. No. 18/493,126, filed Oct. 24, 2023. The cited pending U.S. application is stored in the USPTO IFW system (MPEP 609.04(a)(II)(C)).
U.S. Appl. No. 18/493,142, filed Oct. 24, 2023. The cited pending U.S. application is stored in the USPTO IFW system (MPEP 609.04(a)(II)(C)).
Zhang et al., "Identification and function analysis of canine stimulator of interferon gene (STING)", Microbial Pathogenesis, 2017, vol. 113, pp. 202-208.
Zhang et al., "The function of feline stimulator of interferon gene (STING) is evolutionarily conserved", Veterinary Immunology and Immunopathology, 2016, vol. 169, pp. 54-62.

\* cited by examiner

HETEROCYCLIC COMPOUNDS CAPABLE OF ACTIVATING STING

FIELD OF THE INVENTION

The present invention relates to small molecules capable of activating STING (Stimulator of Interferon Genes), and their salts. Specifically, the present invention relates to heterocyclic compounds capable of activating STING. Furthermore, the invention relates to pharmaceutical compositions and combinations comprising these compounds, as well as their use in methods for the treatment of diseases associated with or modulated by STING. Particularly, the pharmaceutical compositions of the invention are suitable for the therapy of inflammation, allergic and autoimmune diseases, infectious diseases, cancer, and as vaccine adjuvants.

BACKGROUND OF THE INVENTION

STING is one of the pattern-recognition receptors (PRRP) which plays a central role in the innate immune system, distinguishing pathogens and host cells by detecting extracellular and intracellular danger signals including damage-associated molecular patterns (DAMP) and pathogen-associated molecular patterns (PAMP). These recognition processes constitute the first line of defense against viral and bacterial infections and malignant cells. However, pathogens, as well as cancer cells, have evolved ways to evade recognition by the immune system. The aim of immunotherapies is thus to initiate an antigen specific immune response or to re-activate a pre-existing response in certain cell types of the immune system against the pathogenic invaders or cancerous cells.

Among the PRRPs, STING (also known as TMEM173, MPYS, MITA, ERIS) belongs to the family of nucleic acid sensors and is the adaptor for cytosolic DNA signaling. In mammalian cells, in a healthy state, DNA is compartmentalized in the nucleus. In pathogenic situations, such as invasions of DNA-containing pathogens, or in malignant cells, DNA is present in the cytoplasm. Here, STING is critical for detecting the above described cytosolic DNA and to induce an immune reaction against the pathogenic event.

In its basal state, STING exists as a dimer with its N-terminal domain anchored in the ER and the C-terminal domain residing in the cytosol. Cyclic dinucleotides (CDNs), generated by the protein cyclic GMP-AMP Synthase (cGAS) are the natural ligands of STING (Ablasser et al, Nature 498, 380-384, 2013). Binding of CDNs to STING induces conformational changes which allows the binding and activation of the TANK binding kinase (TBK1) and interferon regulatory factor 3 (IRF3), followed by the relocalisation from the ER to perinuclear endosomes (Liu et al, Science 347, Issue 6227, 2630-1-2630-14, 2015). Phosphorylation of the transcription factor IRF3 and NF-kB by TBK1 results in expression of multiple cytokines, including type I interferon (IFN).

Type I IFN production by antigen presenting cells, and other cell types, is considered a key event in the activation of T cells and thereby the differentiation of antigen specific effector CD4 and CD8 T cells. It was shown that the lack of type I IFN resulted in a reduced T cell dependent immune response against viral infections or tumor cells (Zitvogel et al, Nature Reviews Immunology 15, 405-414, 2015). On the other hand, the presence of a type I IFN signature during cancer therapy is associated with increased numbers of tumor infiltrating T cells and potentially favorable clinical outcome (Sistigu et al, Nature Medicine 20, 1301-1309, 2014).

Efficient secretion of type I IFN in the tumor microenvironment and the induction of a T cell dependent immune response against cancer cells depends on the presence of STING, as shown in recent studies in mice (Woo et al, Immunity 41, 5, 830-842, 2014; Corrales et al, Cell Reports 11, 1018-1030, 2015; Deng et al, Immunity 41, 5, 843-852, 2014). The deletion of STING resulted in reduced type I IFN levels in the tumor microenvironment and in a reduced anti-tumor effect in several mouse tumor models, thereby highlighting the importance of the presence of type I IFN. On the other hand, the specific activation of STING resulted in an improved, antigen specific T cell immune response against cancer cells.

Type I interferons can significantly enhance anti-tumor immune responses by inducing activation of both the adaptive and the innate immune cells.

Given the importance of type I IFN in several malignancies including viral infections and cancer therapy, strategies that allow the specific activation of STING are of therapeutic interest. STING activation may be synergistic with various approved chemotherapeutic agents or other anti-cancer therapies such as radiotherapy (Wu et al., Med Res Rev 2020 May; 40(3):1117-1141) or with infectious disease therapies.

In the prior art, small molecule modulators of STING are for example described in WO2020075790.

SUMMARY OF THE INVENTION

Compounds according to the present invention are novel activators of STING as demonstrated in an in vitro reporter system using the THP1-Blue reporter cell line.

In one aspect, the present invention relates to compounds of formula (I),

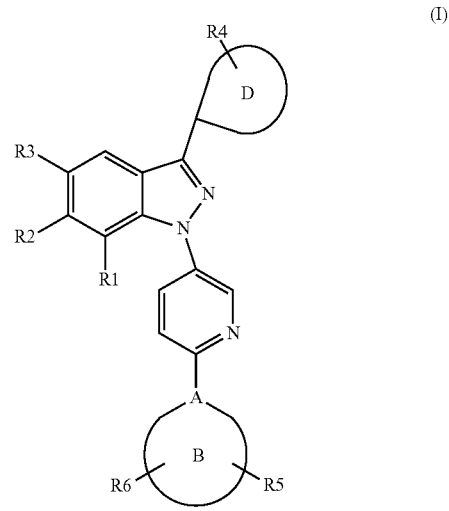

Wherein
A is N or C,
B is a group selected from among the group consisting of
a 5-7-membered monocyclic heterocyclyl containing 1 or 2 N-atoms,
a 6-membered bicyclic heterocyclyl containing 1 N-atom, a 7-11 membered bicyclic heterocyclyl containing 2 N-atoms, a 7-membered bicyclic heterocyclyl containing 1 N-atom and 1 O-atom, a 6-membered monocyclic heterocyclyl containing 1 N-atom and 1 heteroatom selected from the group consisting of O and S, a 9-membered bicyclic heterocyclyl containing 3 heteroatoms, 2 of which are N and the other is O, a 9-membered bicyclic heterocyclyl containing 1 N-atom and 1 S-atom, a 10-membered bicyclic heterocyclyl containing 3 N-atoms, 2 of which are substituted with $C_{1-6}$-alkyl, phenyl, a 9-membered bicyclic heteroaryl containing 3 N-atoms, —$C_{1-4}$-alkylene-pyrimidine, and —$C_{1-4}$-alkylene-O—$C_{1-3}$-alkyl;

D is a group selected from among the group consisting of
a 9-membered bicyclic heteroaryl containing 2 N-atoms,
a 10-membered bicyclic heteroaryl containing 1 N-atom, and
benzodioxole;

$R^1$ is selected from among the group consisting of —H, —$C_{1-6}$-alkyl, —$CF_3$, —$C_{2-6}$-alkynyl, —O—$C_{1-6}$-alkyl and halogen;

$R^2$ is selected from among the group consisting of —H, —$C_{1-6}$-alkyl, —$C_{1-6}$-alkylene-OH, —C(O)OH, —C(O)O—$C_{1-6}$-alkyl and -pyrazolyl-$C_{1-6}$-alkyl;

$R^3$ is —H or —$C_{1-6}$-alkyl;

$R^4$ is selected from among the group consisting of —H, —$C_{1-3}$-alkyl, —$NH_2$, —$NHC_{1-3}$-alkyl and $N(C_{1-3}$-alkyl$)_2$;

$R^5$ is absent or is selected from among the group consisting of —H, —$C_{1-6}$-alkyl, —$S(O_2)$—$C_{1-6}$-alkyl, —NH—S$(O_2)$—$C_{1-6}$-alkyl, =O, —C(O)—$C_{1-6}$-alkyl, —C(O)H, —C(O)OH, —C(O)$NH_2$, —C(O)O—$C_{1-6}$-alkyl, —$NR^{5.1}R^{5.2}$, —$C_{1-6}$-alkylene-C(O)OH, —$S(O_2)$—$NH_2$, -pyrolidin-2-one-1-yl, -tetrazolyl, and a 5-membered heteroaryl with 1 or 2 heteroatoms selected from the group consisting of N and O, substituted with $R^{5.3}$;

$R^{5.1}$ is selected from among the group consisting of —H, —$C_{1-6}$-alkyl, —C(O)—$C_{1-6}$-alkyl and —$C_{1-6}$-alkylene-O—$C_{1-6}$-alkyl;

$R^{5.2}$ is selected from among the group consisting of —H, —$C_{1-6}$-alkyl, —C(O)—$C_{1-6}$-alkyl, —$C_{1-6}$-alkylene-O—$C_{1-6}$-alkyl and —$C_{1-6}$-alkylene-$R^{5.3}$;

$R^{5.3}$ is selected from among the group consisting of —H, —$C_{1-6}$-alkyl and a 6-membered heteroaryl with 1 or 2 heteroatoms selected from a group consisting of N and O;

$R^6$ is absent or is selected from among the group consisting of —H, —$C_{1-6}$-alkyl, =O and —C(O)OH;

or a salt thereof.

The compounds of formula (I) or the salts thereof as defined herein are particularly suitable for the treatment of pathophysiological processes associated with or modulated by STING, particularly for the treatment of inflammation, allergic or autoimmune diseases, infectious diseases or cancer, or for the use as a vaccine adjuvants.

In another aspect, the invention relates to the method of treatment involving the compounds of formula (I) or the salts thereof. In another aspect, the invention relates to the use of a compound of general formula (I) as a medicament. In another aspect, the invention relates to a pharmaceutical composition comprising at least one compound of general formula (I). In another aspect, the invention relates to the use of a compound of general formula (I) in a medicament combination which comprises further active substances. In another embodiment, the invention provides the general synthesis schemes for compounds of general formula (I) including examples and methods.

DETAILED DESCRIPTION OF THE INVENTION

The compounds of the present invention exhibit several advantageous properties, such as favorable binding affinity to human STING, favorable cellular activity as measured by cellular EC50, i.e. in cells bearing different human STING alleles, and favorable permeability in cellular assays.

Thus, in a further aspect the invention provides new compounds of formula (I), including salts thereof, which activate STING and therefore induce cytokine production in STING-dependent fashion in vitro and/or in vivo and possess suitable pharmacological and pharmacokinetic properties for use in therapy, i.e. for use as medicaments.

The compounds according to the present invention typically show a cellular EC50 on STING "HAQ" version of below 10 µM, preferably below 7 µM, more preferably below 5 µM, most preferably below 3 µM.

Furthermore, compounds according to the present invention also show a cellular EC50 of below 10 µM, preferably below 7 µM, more preferably below 5 µM, most preferably below 3 µM on the human STING variant "H232R" (sometimes also designated as wildtype, Yi et al., 2013; PLOS ONE 8(10)).

Furthermore, compounds according to the present invention also show a cellular EC50 of below 10 µM, preferably below 7 µM, more preferably below 5 µM, most preferably below 3 µM on the human STING variant "R232H".

Furthermore, compounds according to the present invention also show a cellular EC50 of below 10 µM, preferably below 7 µM, more preferably below 5 µM, most preferably below 3 µM on the human STING variant "R293Q".

Furthermore, compounds according to the present invention also show a cellular EC50 of below 10 µM, preferably below 7 µM, more preferably below 5 µM, most preferably below 3 µM "AQ".

"H232R", "R232H" and "R293Q" are single amino substitutions at the given position. "AQ" is a variant that consists of two substitutions, G230A and R293Q and "HAQ" is a STING variant that consists of three substitutions: R71H, G230A, and R293Q (Yi et al., 2013; PLOS ONE 8(10)). Activity against different variants of human STING is advantageous as it maximizes the chances to induce the desired pharmacological response in patients with single nucleotide polymorphisms.

Furthermore, the compounds of the present invention display a favourable binding to the human STING protein. Favorable binding affinity to human STING in combination with favorable cellular activity, and/or favorable pharmacokinetic properties can enable lower doses for pharmacological efficacy. Lower doses have the advantages of lower "drug load" or "drug burden" (parent drug and metabolites thereof) for the patient causing potentially less side effects, and lower production costs for the drug product.

Binding of compounds to proteins can be determined by known methods such as surface plasmon resonance, scintillation proximity assay, isothermal titration calorimetry or differential scanning fluorimetry. In the latter test, the temperature at which a protein unfolds, also called the melting temperature $T_m$, is measured by changes in fluorescence of a dye that binds to the hydrophobic parts of the protein. $T_m$ shifts upon binding of a small molecule are correlated with the binding affinity of this small molecule. A high binding affinity of a STING agonist is reflected by a shift in $T_m$ of >10 K, preferably >13 K, more preferably >15K.

In another aspect of the invention, compounds of the invention display a good cellular permeability, facilitating target engagement of the intracellular STING protein, as measured in the Caco-2-cell line, with a $P_{app,AB}$ as measured from apical to basolateral side of the cell monolayer (Caco-2 A→B) of above 5×10E-6 cm/s, preferably above 8×10E-6 cm/s, more preferably above 10×10E-6 cm/s. Furthermore, the compounds of the invention show a low efflux ratio from the Caco cells (calculated as shown hereinafter) of <8, preferably <5, more preferably <3.5, signifying good residence time inside the cells and thereby facilitating longer duration of target engagement.

In another aspect of the invention, compounds of the invention have a solubility of >40 µg/ml at pH 6.8, preferably >50 µg/ml at pH 6.8, more preferably >60 µg/ml at pH 6.8 as shown hereinafter, thereby facilitating the use of these compounds for systemic as well as inhalative or intratumoral administration.

The compounds of the invention according to general formula (I)

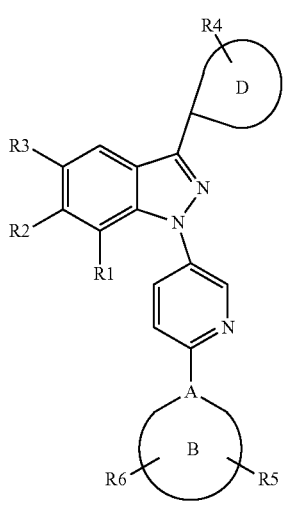

(I)

Wherein

A is N or C,

B is a group selected from among the group consisting of
a 5-7-membered monocyclic heterocyclyl containing 1 or 2 N-atoms,
a 6-membered bicyclic heterocyclyl containing 1 N-atom,
a 7-11 membered bicyclic heterocyclyl containing 2 N-atoms,
a 7-membered bicyclic heterocyclyl containing 1 N-atom and 1 O-atom,
a 6-membered monocyclic heterocyclyl containing 1 N-atom and 1 heteroatom selected from the group consisting of O and S,
a 9-membered bicyclic heterocyclyl containing 3 heteroatoms, 2 of which are N and the other is O,
a 9-membered bicyclic heterocyclyl containing 1 N-atom and 1 S-atom,
a 10-membered bicyclic heterocyclyl containing 3 N-atoms, 2 of which are substituted with $C_{1-6}$-alkyl, phenyl,
a 9-membered bicyclic heteroaryl containing 3 N-atoms,
—$C_{1-4}$-alkylene-pyrimidine, and
—$C_{1-4}$-alkylene-O—$C_{1-3}$-alkyl;

D is a group selected from among the group consisting of
a 9-membered bicyclic heteroaryl containing 2 N-atoms,
a 10-membered bicyclic heteroaryl containing 1 N-atom, and
benzodioxole;

$R^1$ is selected from among the group consisting of —H, —$C_{1-6}$-alkyl, —$CF_3$, —$C_{2-6}$-alkynyl, —O—$C_{1-6}$-alkyl and halogen;

$R^2$ is selected from among the group consisting of —H, —$C_{1-6}$-alkyl, —$C_{1-6}$-alkylene-OH, —C(O)OH, —C(O)O—$C_{1-6}$-alkyl and -pyrazolyl-$C_{1-6}$-alkyl;

$R^3$ is —H or —$C_{1-6}$-alkyl;

$R^4$ is selected from among the group consisting of —H, —$C_{1-3}$-alkyl, —$NH_2$, —$NHC_{1-3}$-alkyl and $N(C_{1-3}$-alkyl$)_2$;

$R^5$ is absent or is selected from among the group consisting of —H, —$C_{1-6}$-alkyl, —$S(O_2)$—$C_{1-6}$-alkyl, —NH—S$(O_2)$—$C_{1-6}$-alkyl, =O, —C(O)—$C_{1-6}$-alkyl, —C(O)H, —C(O)OH, —C(O)NH$_2$, —C(O)O—$C_{1-6}$-alkyl, —$NR^{5.1}R^{5.2}$, —$C_{1-6}$-alkylene-C(O)OH, —$S(O_2)$—$NH_2$, -pyrolidin-2-one-1-yl, -tetrazolyl, and a 5-membered heteroaryl with 1 or 2 heteroatoms selected from the group consisting of N and O, substituted with $R^{5.3}$;

$R^{5.1}$ is selected from among the group consisting of —H, —$C_{1-6}$-alkyl, —C(O)—$C_{1-6}$-alkyl and —$C_{1-6}$-alkylene-O—$C_{1-6}$-alkyl;

$R^{5.2}$ is selected from among the group consisting of —H, —$C_{1-6}$-alkyl, —C(O)—$C_{1-6}$-alkyl, —$C_{1-6}$-alkylene-O—$C_{1-6}$-alkyl and —$C_{1-6}$-alkylene-$R^{5.3}$;

$R^{5.3}$ is selected from among the group consisting of —H, —$C_{1-6}$-alkyl and a 6-membered heteroaryl with 1 or 2 heteroatoms selected from a group consisting of N and O;

$R^6$ is absent or is selected from among the group consisting of —H, —$C_{1-6}$-alkyl, =O and —C(O)OH;

or a salt thereof as defined herein are particularly suitable for the treatment of pathophysiological processes associated with or modulated by STING, particularly for the treatment of inflammation, allergic or autoimmune diseases, infectious diseases or cancer, or for the use as a vaccine adjuvants. Accordingly, in another aspect the present invention further relates to compounds of formula (I) as defined herein or pharmaceutically acceptable salts thereof for use as a medicament. Other aspects of the present invention will become apparent to the person skilled in the art directly from the foregoing and following description and examples.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, in groups like HO, $H_2N$, (O)S, $(O)_2S$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkylene" means an aryl group which is bound to a $C_{1-3}$-alkyl-group, the latter of which is bound to the core or to the group to which the substituent is attached.

In case a compound of the present invention is depicted in the form of a chemical name and as a formula, in case of any discrepancy the formula shall prevail. A wavy line may be used in sub-formulas to indicate the bond which is connected to the core molecule as defined.

For example, the term "3-carboxypropyl-group" represents the following substituent:

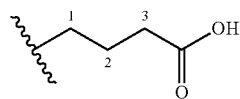 [SMILES: *CCCC(=O)O]

wherein the carboxy group is attached to the third carbon atom of the propyl group. The terms "1-methylpropyl-", "2,2-dimethylpropyl-" or "cyclopropylmethyl-" group represent the following groups:

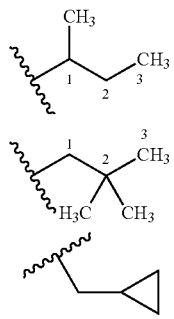

The wavy line may be used in sub-formulas to indicate the bond which is connected to the core molecule as defined.

1.1.1.1 Term Substituted

The term "substituted" as used herein, means that one or more hydrogens on the designated atom are replaced by a group selected from a defined group of substituents, provided that the designated atom's normal valence is not exceeded, and that the substitution results in a stable compound. Likewise, the term "substituted" may be used in connection with a chemical moiety instead of a single atom, e.g. "substituted alkyl", "substituted aryl" or the like.

1.1.1.2 Stereochemistry-Solvates-Hydrates

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as solvates thereof such as for instance hydrates.

Unless specifically indicated, also "pharmaceutically acceptable salts" as defined in more detail below shall encompass solvates thereof such as for instance hydrates.

1.1.1.3 Stereoisomers

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

1.1.1.4 Salts

The phrase "pharmaceutically acceptable" is employed herein to refer to those compounds, materials, compositions, and/or dosage forms which are, within the scope of sound medical judgment, suitable for use in contact with the tissues of human beings without excessive toxicity, irritation, allergic response, or other problem or complication, and commensurate with a reasonable benefit/risk ratio.

As used herein, "pharmaceutically acceptable salt" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent such as ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

1.1.1.5 Halogen

The term halogen denotes fluorine, chlorine, bromine and iodine.

1.1.1.6 Heteroatoms

Heteroatoms can be present in all the possible oxidation stages. For example, sulphur can be present as sulphoxide (R—S(O)—R') and sulphone (—R—S(O)$_2$—R').

1.1.1.7 Alkyl

The term "$C_{1-n}$-alkyl", wherein n is an integer selected from 2, 3, 4, 5 or 6, preferably 4, 5 or 6, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

1.1.1.8 Alkylene

The term "$C_{1-n}$-alkylene" wherein n is an integer selected from 2, 3, 4, 5 or 6, preferably 4, 5 or 6, either alone or in combination with another radical, denotes an acyclic, saturated, branched or linear chain divalent alkyl radical containing from 1 to n carbon atoms. For example the term $C_{1-4}$-alkylene includes —CH$_2$—, —CH$_2$—CH$_2$—, —CH(CH$_3$)—, —CH$_2$—CH$_2$—CH$_2$—, —C(CH$_3$)$_2$—, —CH(CH$_2$CH$_3$)—, —CH(CH$_3$)—CH$_2$—, —CH$_2$—CH(CH$_3$)—, —CH$_2$—CH$_2$—CH$_2$—CH$_2$—, —CH$_2$—CH$_2$—CH(CH$_3$)—, —CH(CH$_3$)—CH$_2$—CH$_2$—, —CH$_2$—CH(CH$_3$)—CH$_2$—, —CH$_2$—C(CH$_3$)$_2$—, —C(CH$_3$)$_2$—CH$_2$—, —CH(CH$_3$)—CH(CH$_3$)—, —CH$_2$—CH(CH$_2$CH$_3$)—, —CH(CH$_2$CH$_3$)—CH$_2$—, —CH(CH$_2$CH$_2$CH$_3$)—, —CH(CH(CH$_3$))$_2$— and —C(CH$_3$)(CH$_2$CH$_3$)—.

1.1.1.9 Alkenyl

The term "$C_{2-m}$-alkenyl" is used for a group "$C_{2-m}$-alkyl" wherein m is an integer selected from 3, 4, 5 or 6, preferably 4, 5 or 6, if at least two carbon atoms of said group are bonded to each other by a double bond.

1.1.1.10 Alkenylene

The term "$C_{2-m}$-alkenylene" is used for a group "$C_{2-m}$-alkylene" wherein m is an integer selected from 3, 4, 5 or 6, preferably 4, 5 or 6, if at least two carbon atoms of said group are bonded to each other by a double bond.

1.1.1.11 Alkynyl

The term "$C_{2-m}$-alkynyl" is used for a group "$C_{2-m}$-alkyl" wherein m is an integer selected from 3, 4, 5 or 6, preferably 4, 5 or 6, if at least two carbon atoms of said group are bonded to each other by a triple bond.

1.1.1.12 Alkynylene

The term "$C_{2-m}$-alkynylene" is used for a group "$C_{2-m}$-alkylene" wherein m is an integer selected from 3, 4, 5 or 6, preferably 4, 5 or 6, if at least two of those carbon atoms of said group are bonded to each other by a triple bond.

1.1.1.13 Cycloalkyl

The term "$C_{3-k}$-cycloalkyl", wherein k is an integer selected from 3, 4, 5, 6, 7 or 8, preferably 4, 5 or 6, either alone or in combination with another radical denotes a cyclic, saturated, unbranched hydrocarbon radical with 3 to k C atoms. For example the term $C_{3-7}$-cycloalkyl includes cyclopropyl, cyclobutyl, cyclopentyl, cyclohexyl and cycloheptyl.

1.1.1.14 Cycloalkenyl

The term "$C_{3-k}$-cycloalkenyl", wherein k is an integer integer selected from 3, 4, 5, 6, 7 or 8, preferably 4, 5 or 6, either alone or in combination with another radical, denotes a cyclic, unsaturated, but non-aromatic, unbranched hydrocarbon radical with 3 to k C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

1.1.1.15 Halo-(Alkyl, Alkylene or Cycloalkyl)

The term "halo" added to an "alkyl", "alkylene" or "cycloalkyl" group (saturated or unsaturated) defines an alkyl, alkylene or cycloalkyl group wherein one or more hydrogen atoms are replaced by a halogen atom selected from among fluorine, chlorine or bromine, preferably fluorine and chlorine, particularly preferred is fluorine. Examples include: H$_2$FC—, HF$_2$C—, F$_3$C—.

1.1.1.16 Carbocyclyl

The term "carbocyclyl", either alone or in combination with another radical, means a mono-, bi- or tricyclic ring structure consisting of 3 to 14 carbon atoms. The term "carbocyclyl" refers to fully saturated, partially saturated and aromatic ring systems. The term "carbocyclyl" encompasses fused, bridged and spirocyclic systems.

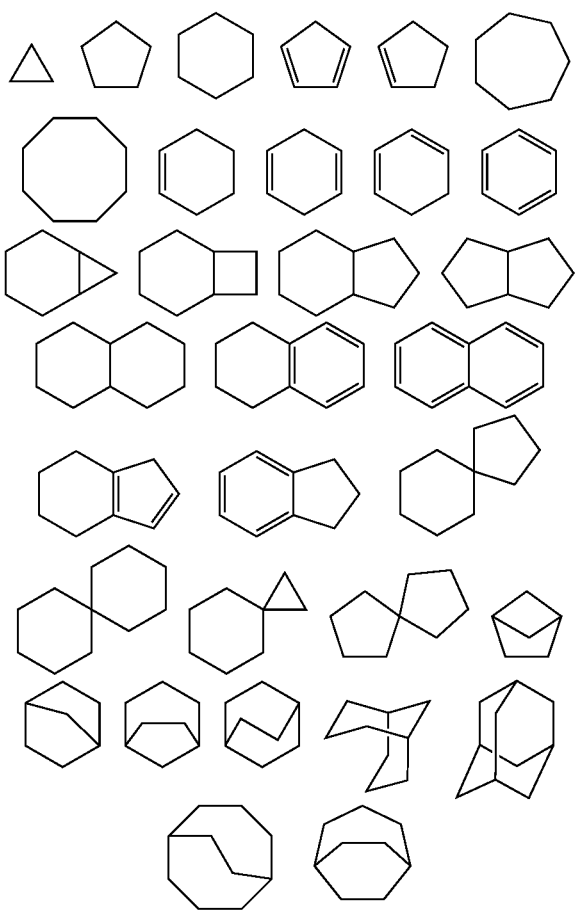

1.1.1.17 Aryl

The term "aryl" as used herein, either alone or in combination with another radical, denotes a carbocyclic aromatic monocyclic group containing 6 carbon atoms which is optionally further fused to a second five- or six-membered, carbocyclic group which is aromatic, saturated or unsaturated. Aryl includes, but is not limited to, phenyl, indanyl, indenyl, naphthyl, anthracenyl, phenanthrenyl, tetrahydronaphthyl and dihydronaphthyl.

1.1.1.18 Heterocyclyl

The term "heterocyclyl" means a saturated or unsaturated mono- or polycyclic ring system optionally comprising aromatic rings, containing one or more heteroatoms selected from N, O, S, SO, SO$_2$, consisting of 3 to 14 ring atoms wherein none of the heteroatoms is part of the aromatic ring. The term "heterocyclyl" is intended to include all the possible isomeric forms.

Thus, the term "heterocyclyl" includes the following exemplary structures (not depicted as radicals as each form is optionally attached through a covalent bond to any atom so long as appropriate valences are maintained):

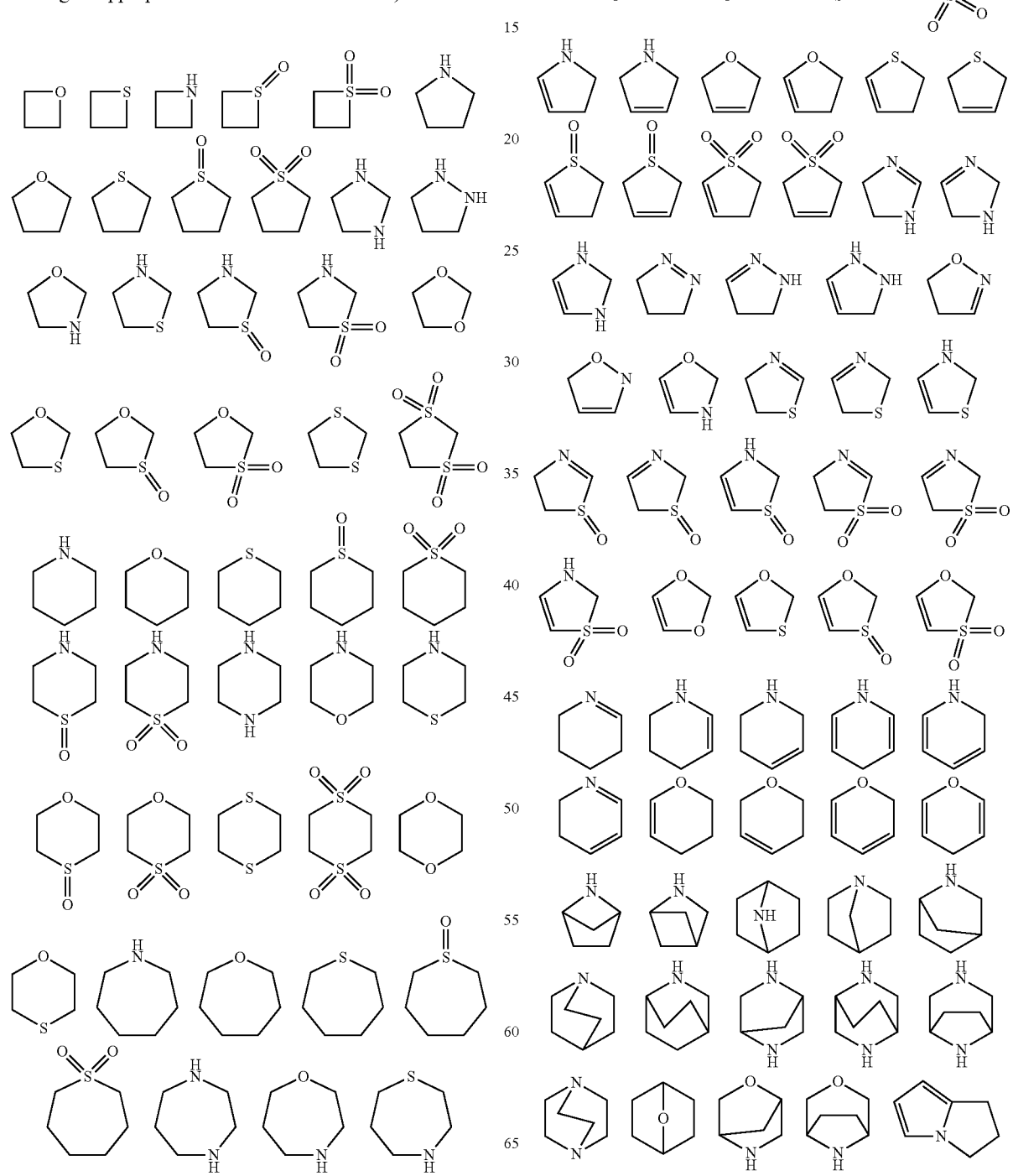

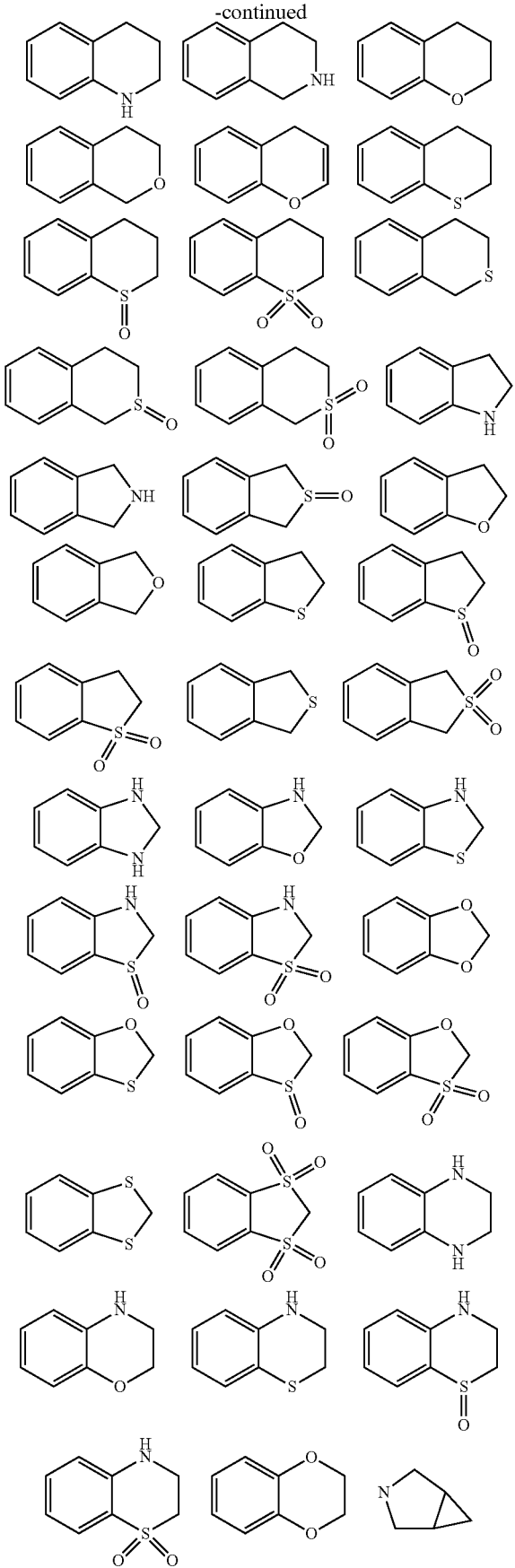
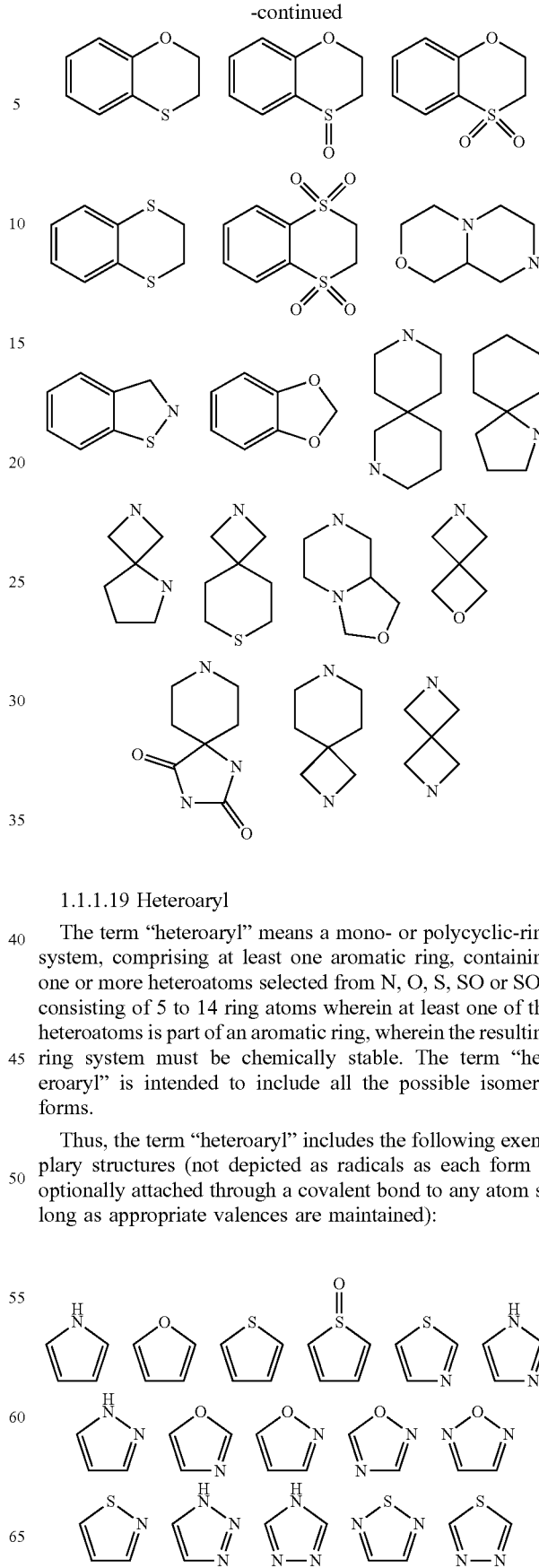

1.1.1.19 Heteroaryl

The term "heteroaryl" means a mono- or polycyclic-ring system, comprising at least one aromatic ring, containing one or more heteroatoms selected from N, O, S, SO or $SO_2$, consisting of 5 to 14 ring atoms wherein at least one of the heteroatoms is part of an aromatic ring, wherein the resulting ring system must be chemically stable. The term "heteroaryl" is intended to include all the possible isomeric forms.

Thus, the term "heteroaryl" includes the following exemplary structures (not depicted as radicals as each form is optionally attached through a covalent bond to any atom so long as appropriate valences are maintained):

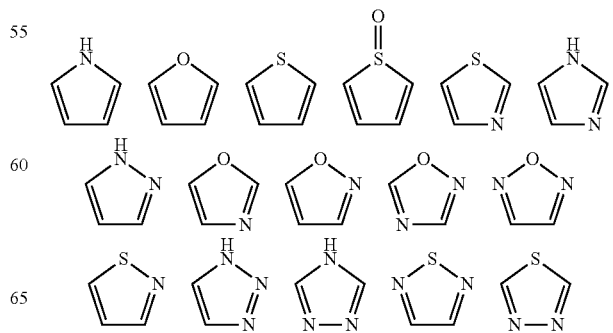

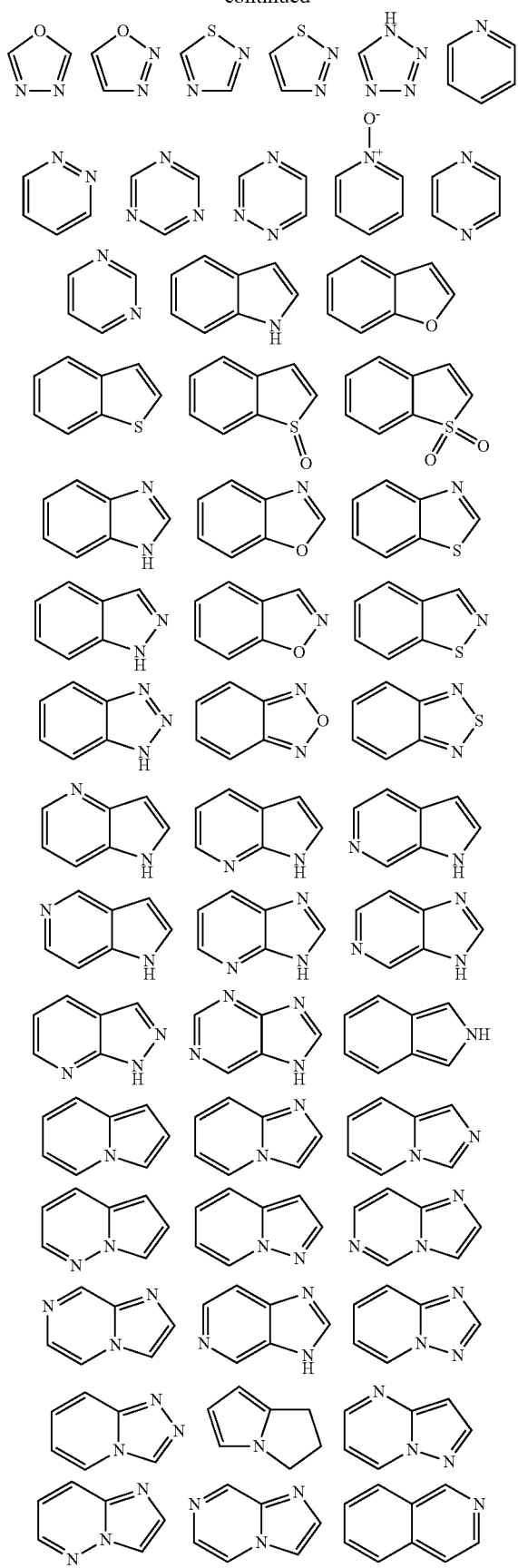

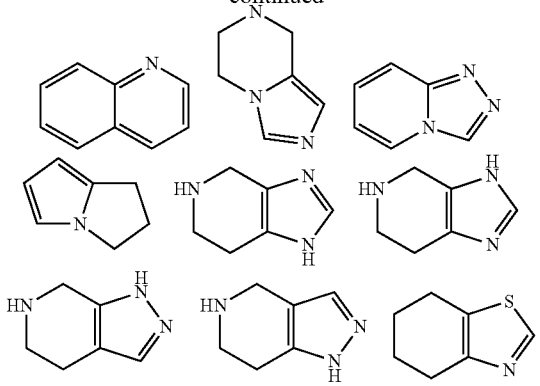

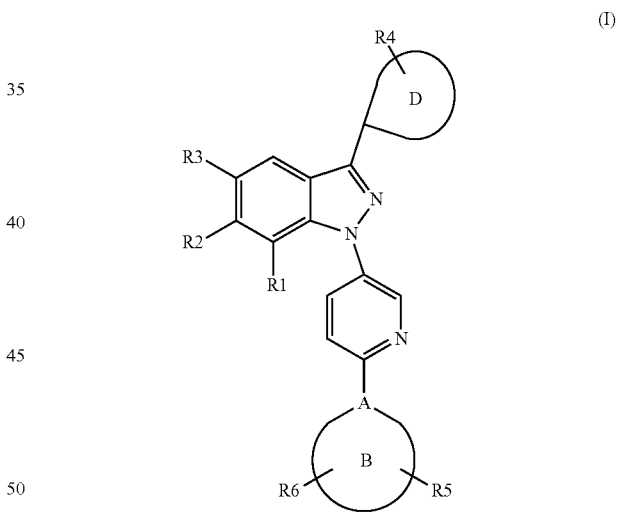

Many of the terms given above may be used repeatedly in the definition of a formula or group and in each case have one of the meanings given above, independently of one another.

The term "bicyclic ring systems" means groups consisting of 2 joined cyclic substructures including spirocyclic, fused, and bridged ring systems.

PREFERRED EMBODIMENTS

One particular embodiment of the invention relates to compounds of formula (I) or salts thereof, wherein $R^1$ is selected from among the group consisting of —$C_{1-6}$-alkyl, —$CF_3$, —O—$C_{1-6}$-alkyl and halogen.

Another particular embodiment relates to compounds of formula (I) or salts thereof wherein $R^1$ is selected from among the group consisting of —$C_{1-6}$-alkyl, —$CF_3$, —O—$C_{1-6}$-alkyl, —Br and —Cl.

Another particular embodiment relates to compounds of formula (I) or salts thereof wherein $R^1$ is selected from among the group consisting of —$C_{1-6}$-alkyl, —$CF_3$, —Br and —Cl.

Another particular embodiment relates to compounds of formula (I) or salts thereof wherein $R^1$ is selected from among the group consisting of —$C_{1-6}$-alkyl, —$CF_3$, —O—$C_{1-6}$-alkyl, halogen and wherein $R^4$ is —H or —$C_{1-3}$-alkyl.

Another particular embodiment of the invention relates to compounds of formula (I) or salts thereof wherein $R^2$ is —H.

Another particular embodiment of the invention relates to compounds of formula (I) or salts thereof wherein $R^3$ is —H.

Another particular embodiment of the invention relates to compounds of formula (I) or salts thereof wherein $R^2$ is —H and wherein $R^3$ is —H.

Another particular embodiment of the invention relates to compounds of formula (I) or salts thereof wherein $R^4$ is —H or —$C_{1-3}$-alkyl.

Another particular embodiment of the invention relates to compounds of formula (I) or salts thereof wherein $R^5$ is selected from among the group consisting of —H, —$C_{1-6}$-alkyl, —S(O$_2$)—$C_{1-6}$-alkyl, =O, —C(O)H, —C(O)NH$_2$, —C(O)OH, —C(O)O—$C_{1-6}$-alkyl, —NR$^{5.1}$R$^{5.2}$ and a 5-membered heteroaryl with 1 or 2 heteroatoms selected from a group consisting of N and O, substituted with $R^{5.3}$; and wherein $R^{5.1}$ is selected from among the group consisting of —H, —$C_{1-6}$-alkyl, —C(O)—$C_{1-6}$-alkyl and —$C_{1-6}$-alkylene-O—$C_{1-6}$-alkyl; and wherein $R^{5.2}$ is selected from among the group consisting of —H, —$C_{1-6}$-alkyl, —C(O)—$C_{1-6}$-alkyl, —$C_{1-6}$-alkylene-O—$C_{1-6}$-alkyl and —$C_{1-6}$-alkyl-$R^{5.3}$; and wherein $R^{5.3}$ is —H or —$C_{1-6}$-alkyl.

Another particular embodiment of the invention relates to compounds of formula (I) or salts thereof wherein $R^5$ is selected from among the group consisting of —H, —$C_{1-6}$-alkyl, —S(O$_2$)—$C_{1-6}$-alkyl, —NH—S(O$_2$)—$C_{1-6}$-alkyl, =O, —C(O)—$C_{1-6}$-alkyl, —C(O)H, —C(O)OH, —C(O)NH$_2$, —C(O)O—$C_{1-6}$-alkyl, —NR$^{5.1}$R$^{5.2}$, —$C_{1-6}$-alkylene-C(O)OH, —S(O$_2$)—NH$_2$, -pyrolidin-2-one-1-yl and a 5-membered heteroaryl with 1 or 2 heteroatoms selected from the group consisting of N and O, substituted with $R^{5.3}$; and wherein $R^{5.1}$ is selected from among the group consisting of —H, —$C_{1-6}$-alkyl, —C(O)—$C_{1-6}$-alkyl and —$C_{1-6}$-alkylene-O—$C_{1-6}$-alkyl; and wherein $R^{5.2}$ is selected from among the group consisting of —H, —$C_{1-6}$-alkyl, —C(O)—$C_{1-6}$-alkyl, —$C_{1-6}$-alkylene-O—$C_{1-6}$-alkyl and —$C_{1-6}$-alkylene-$R^{5.3}$; and wherein $R^{5.3}$ is selected from among the group consisting of —H, —$C_{1-6}$-alkyl and a 6-membered heteroaryl with 1 or 2 heteroatoms selected from a group consisting of N and O.

Another particular embodiment of the invention relates to compounds of formula (I) or salts thereof wherein $R^5$ is selected from among the group consisting of —H, —$C_{1-6}$-alkyl, —S(O$_2$)—$C_{1-6}$-alkyl, =O, —C(O)H, C(O)NH$_2$, —C(O)OH, —C(O)O—$C_{1-6}$-alkyl and —NR$^{5.1}$R$^{5.2}$; and wherein $R^{5.1}$ is selected from among the group consisting of —H, —$C_{1-6}$-alkyl, —C(O)—$C_{1-6}$-alkyl and —$C_{1-6}$-alkyl-O—$C_{1-6}$-alkyl; and wherein $R^{5.2}$ is selected from among the group consisting of —H, —$C_{1-6}$-alkyl, —C(O)—$C_{1-6}$-alkyl and —$C_{1-6}$-alkylene-O—$C_{1-6}$-alkyl.

Another particular embodiment of the invention relates to compounds of formula (I) or salts thereof wherein $R^5$ is selected from among the group consisting of —H, —$C_{1-6}$-alkyl, —S(O$_2$)—$C_{1-6}$-alkyl, =O, —C(O)H, —C(O)NH$_2$, —C(O)OH and —C(O)O—$C_{1-6}$-alkyl.

Another particular embodiment of the invention relates to compounds of formula (I) or salts thereof wherein $R^5$ is selected from among the group consisting of —C(O)H, C(O)NH$_2$, —C(O)OH and —C(O)O—$C_{1-6}$-alkyl.

Another particular embodiment of the invention relates to compounds of formula (I) or salts thereof wherein $R^5$ is —C(O)OH or —C(O)O—$C_{1-3}$-alkyl.

Another particular embodiment of the invention relates to compounds of formula (I) or salts thereof wherein $R^5$ is absent if necessitated by atom valency.

Another particular embodiment of the invention relates to compounds of formula (I) or salts thereof wherein $R^6$ is —H or —C(O)OH.

Another particular embodiment of the invention relates to compounds of formula (I) or salts thereof wherein $R^6$ is absent if necessitated by atom valency.

Another particular embodiment of the invention relates to compounds of formula (I) or salts thereof wherein $R^5$ is —H and $R^6$ is —H.

Another particular embodiment of the invention relates to compounds of formula (I) or salts thereof wherein A is N.

Another particular embodiment of the invention relates to compounds of formula (I) or salts thereof wherein B is a group selected from among the group consisting of a 5-7-membered monocyclic heterocyclyl containing 1 or 2 N-atoms, a 6-membered bicyclic heterocyclyl containing 1 N-atom, a 7-11 membered bicyclic heterocyclyl containing 2-3 N-atoms, a 7-membered bicyclic heterocyclyl containing 1 N-atom and 1 O-atom, a 6-membered monocyclic heterocyclyl containing 1 N-atom and 1 heteroatom selected from the group consisting of O and S, a 9-membered bicyclic heterocyclyl containing 3 heteroatoms, 2 of which are N and the other is O, a 9-membered bicyclic heterocyclyl containing 1 N-atom and 1 S-atom and a 10-membered bicyclic heterocyclyl containing 3 N-atoms, 2 of which are substituted with $C_{1-6}$-alkyl.

Another particular embodiment of the invention relates to compounds of formula (I) or salts thereof wherein B is a group selected from among the group consisting of

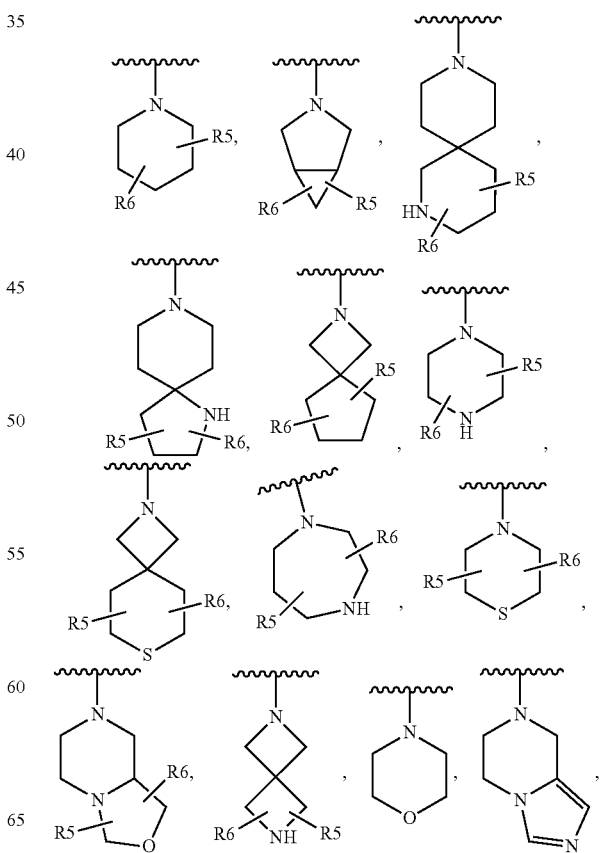

-continued
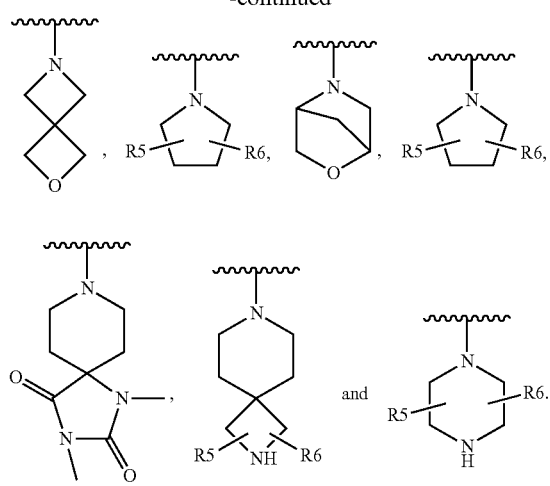
Another particular embodiment of the invention relates to compounds of formula (I) or salts thereof wherein B is a group selected from among the group consisting of
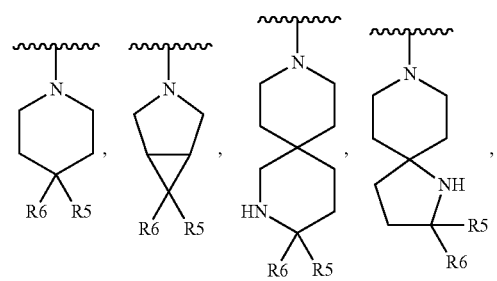
-continued
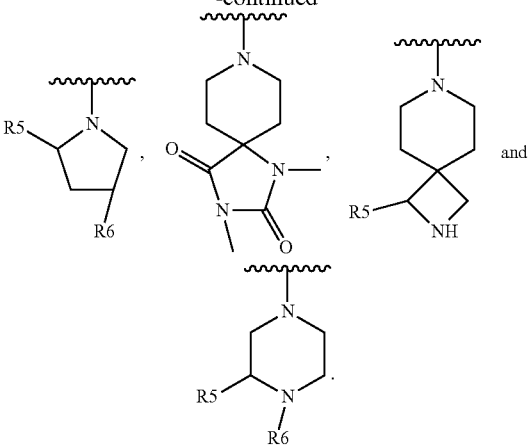
Another particular embodiment of the invention relates to compounds of formula (I) or salts thereof wherein B is selected from among the group consisting of
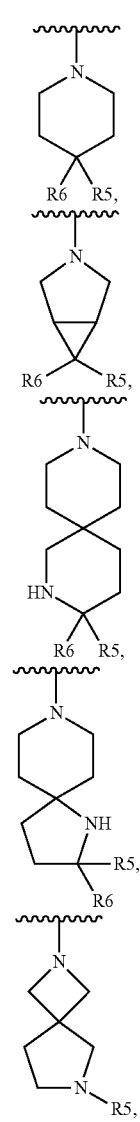

-continued

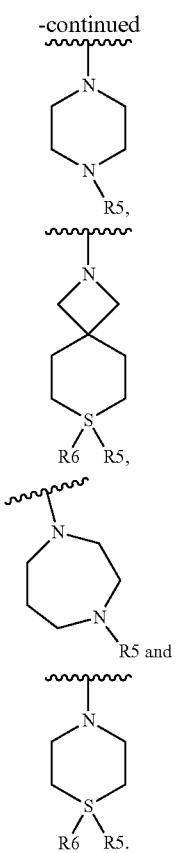

Another particular embodiment of the invention relates to compounds of formula (I) or salts thereof wherein D is selected from among the group consisting of a 9-membered bicyclic heteroaryl containing 2 N-atoms and a 10-membered bicyclic heteroaryl containing 1 N-atom.

Another particular embodiment of the invention relates to compounds of formula (I) or salts thereof wherein D is selected from among the group consisting of

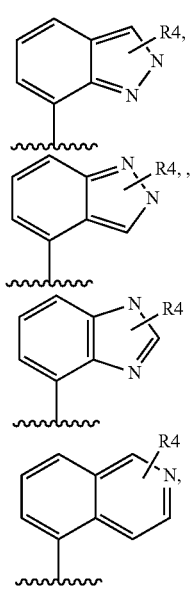

-continued

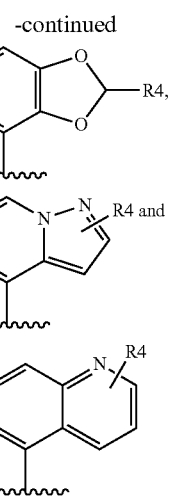

Another particular embodiment of the invention relates to compounds of formula (I) or salts thereof wherein D is selected from among the group consisting of

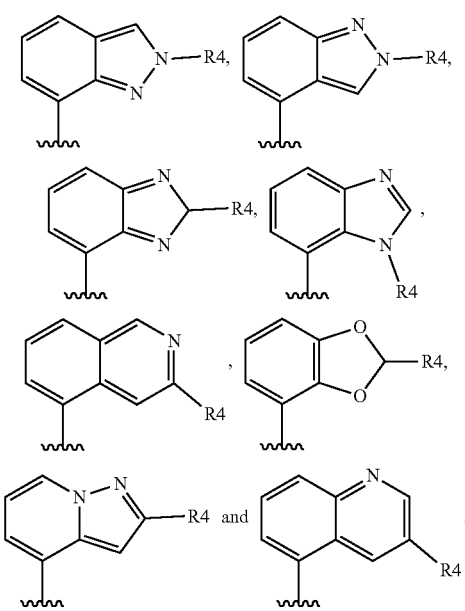

Another particular embodiment of the invention relates to compounds of formula (I) or salts thereof wherein D is selected from among the group consisting of

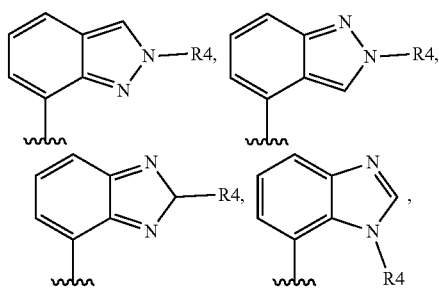

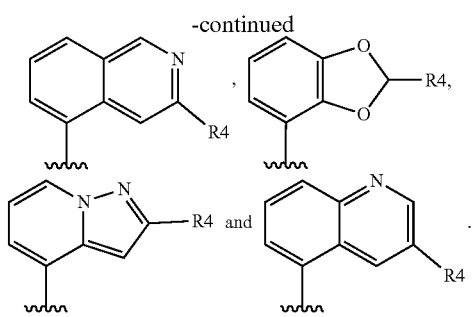

and wherein R¹ is selected from among the group consisting of —$C_{1-6}$-alkyl, —$CF_3$, —O—$C_{1-6}$-alkyl, halogen and wherein R² is —H and wherein R³ is —H and wherein R⁴ is —H or —$C_{1-3}$-alkyl.

Another particular embodiment of the invention relates to compounds of formula (I) or salts thereof wherein D is selected from among the group consisting of

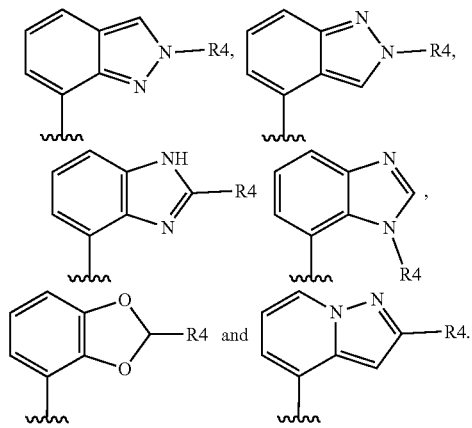

Another particular embodiment of the invention relates to compounds of formula (I) or salts thereof wherein D is selected from among the group consisting of

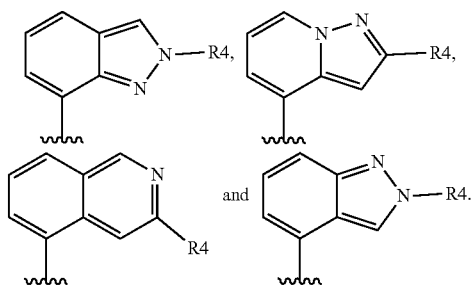

Another particular embodiment of the invention relates to compounds of formula (I) or salts thereof wherein D is

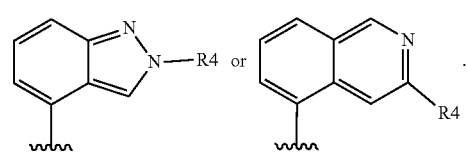

Another particular embodiment of the invention relates to compounds of formula (I) or salts thereof wherein D is selected from among the group consisting of

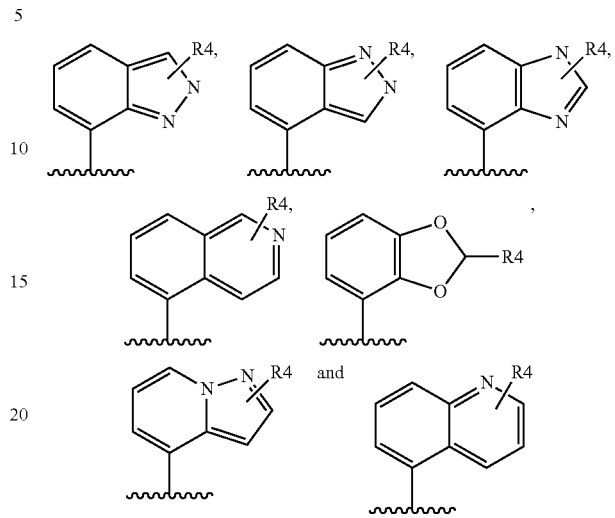

and wherein R² is —H and wherein R³ is —H.

Another particular embodiment of the invention relates to compounds of formula (I) or salts thereof wherein D is selected from among the group consisting of

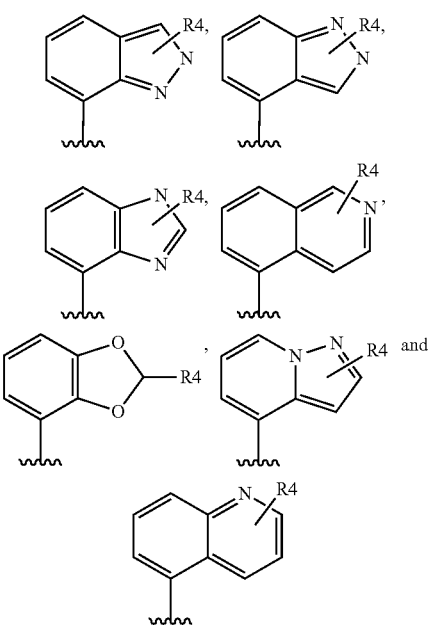

and wherein R¹ is selected from among the group consisting of —Br and —Cl, and wherein R² is —H and wherein R³ is —H.

Another particular embodiment of the invention relates to compounds of formula (I) or salts thereof wherein D is selected from among the group consisting of Another particular embodiment of the invention relates to compounds of formula (I) or salts thereof wherein D is selected from among the group consisting of

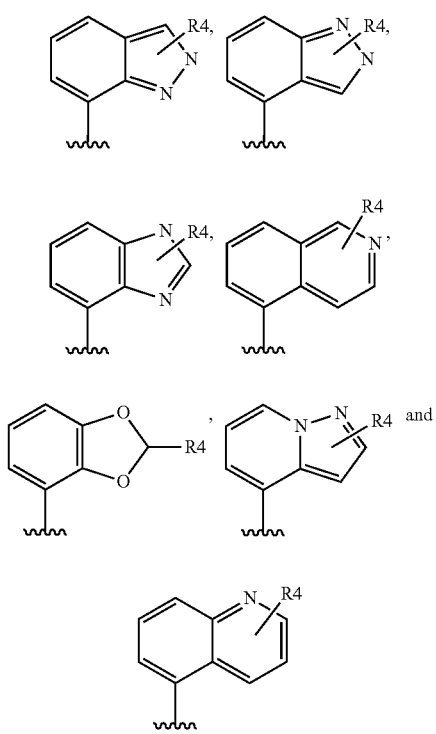

and wherein R¹ is selected from among the group consisting of —C$_{1-6}$-alkyl, —CF$_3$, —O—C$_{1-6}$-alkyl, —Br and —Cl.

Another particular embodiment of the invention relates to compounds of formula (I) or salts thereof wherein D is selected from among the group consisting of

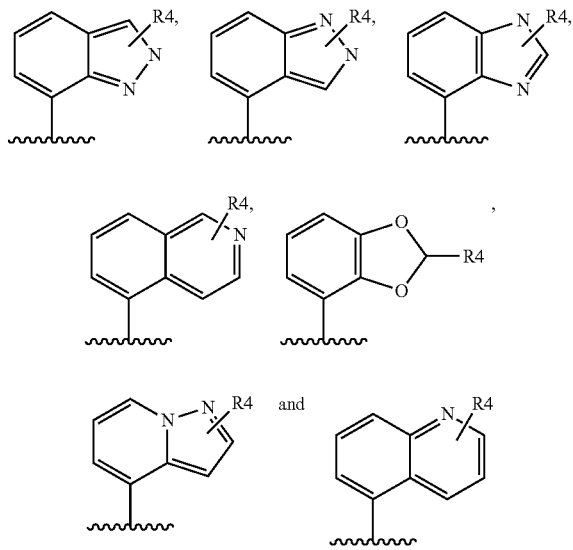

and wherein R¹ is selected from among the group consisting of —C$_{1-6}$-alkyl, —CF$_3$, —O—C$_{1-6}$-alkyl, —Br and —Cl; and wherein R² is —H; and wherein R³ is —H.

Another particular embodiment of the invention relates to compounds of formula (I) or salts thereof wherein D is

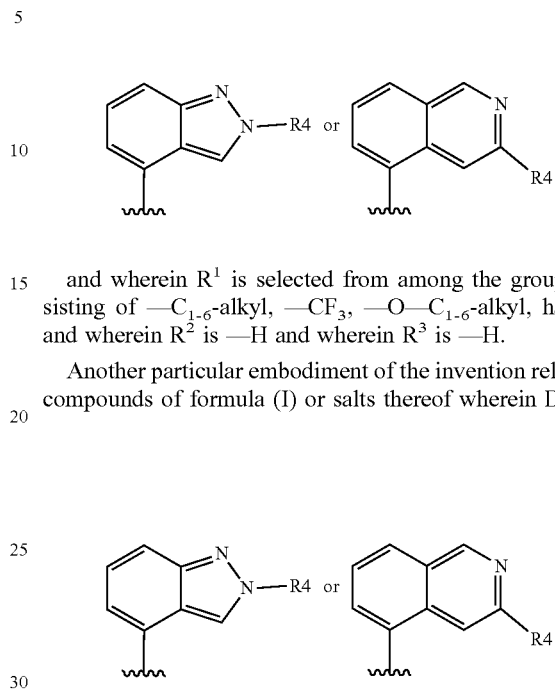

and wherein R¹ is selected from among the group consisting of —C$_{1-6}$-alkyl, —CF$_3$, —O—C$_{1-6}$-alkyl, halogen and wherein R² is —H and wherein R³ is —H.

Another particular embodiment of the invention relates to compounds of formula (I) or salts thereof wherein D is

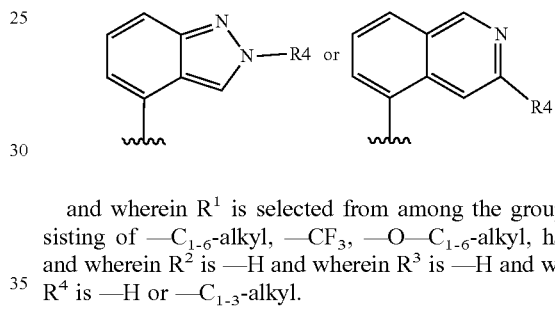

and wherein R¹ is selected from among the group consisting of —C$_{1-6}$-alkyl, —CF$_3$, —O—C$_{1-6}$-alkyl, halogen and wherein R² is —H and wherein R³ is —H and wherein R⁴ is —H or —C$_{1-3}$-alkyl.

Another particular embodiment of the invention relates to compounds of formula (I) or salts thereof selected from among the group consisting of

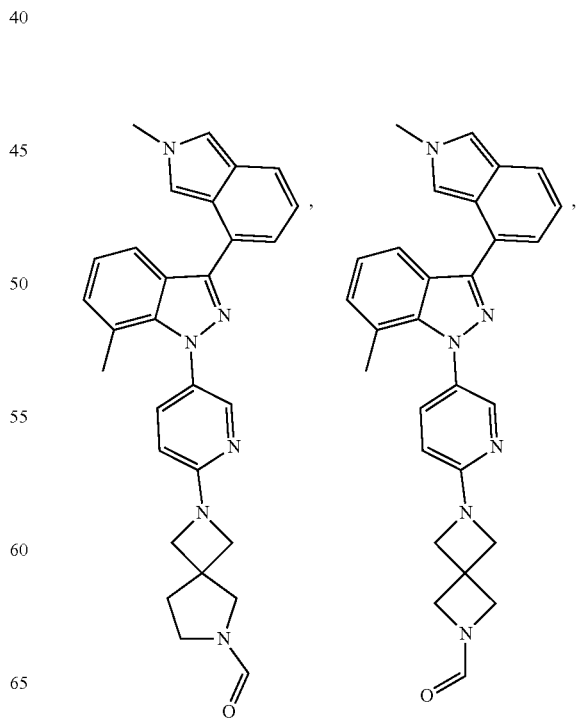

-continued
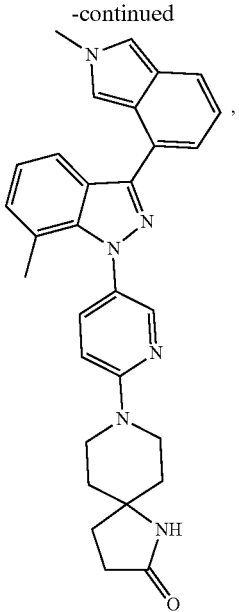
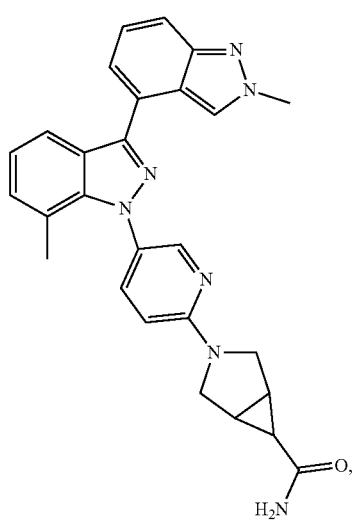
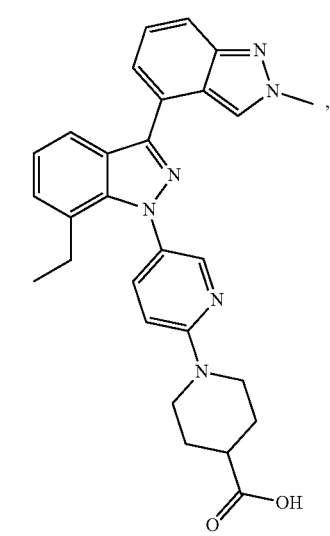
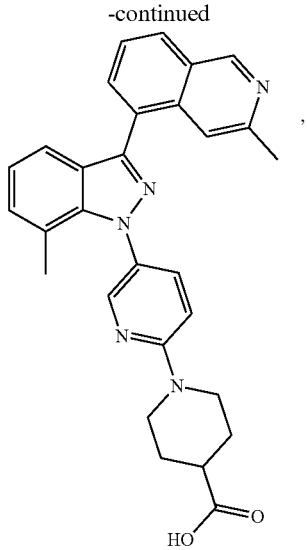
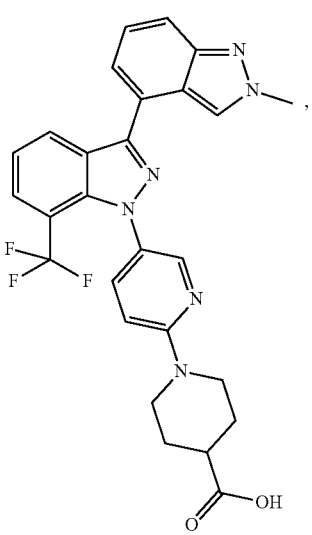

29

31
-continued
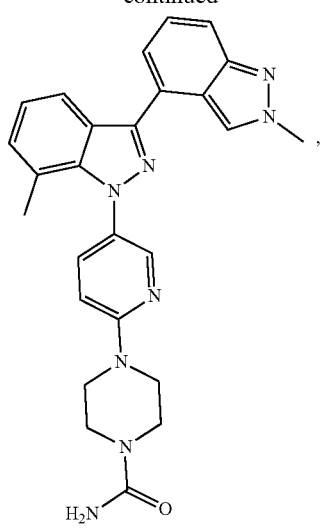
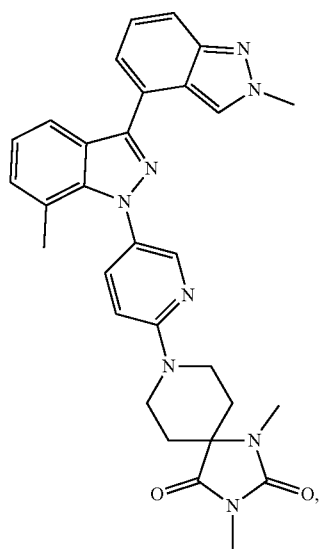
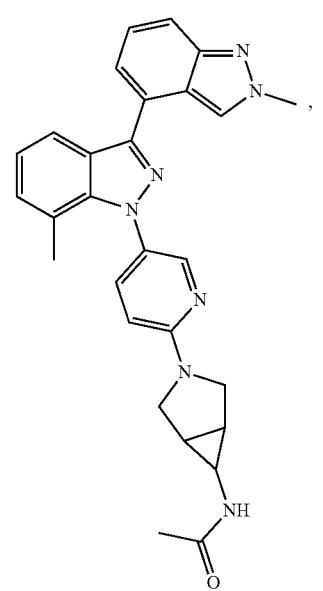
32
-continued
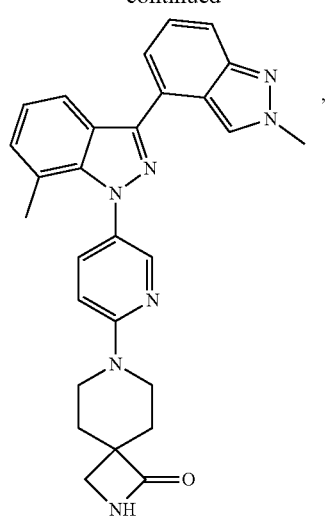
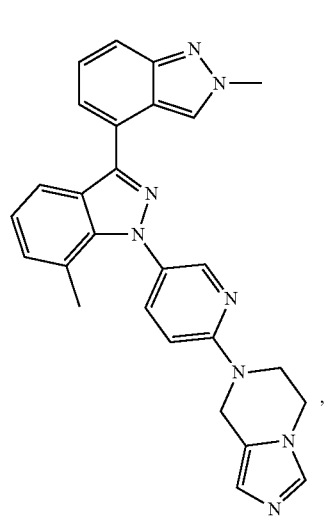
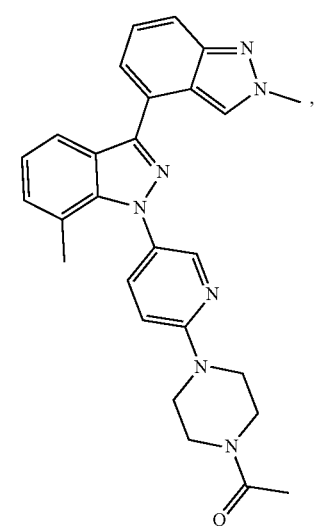

33
-continued
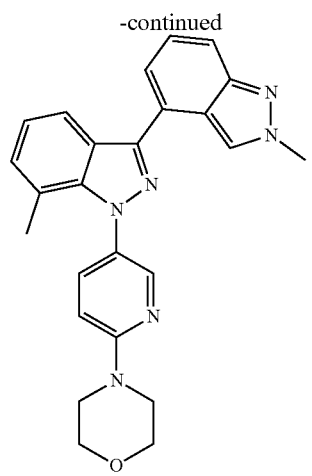
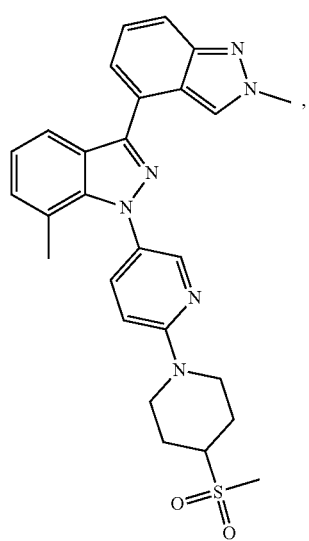
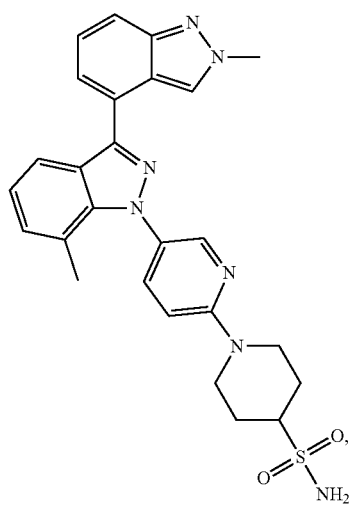
34
-continued
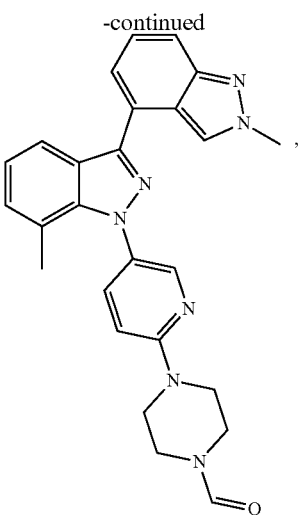
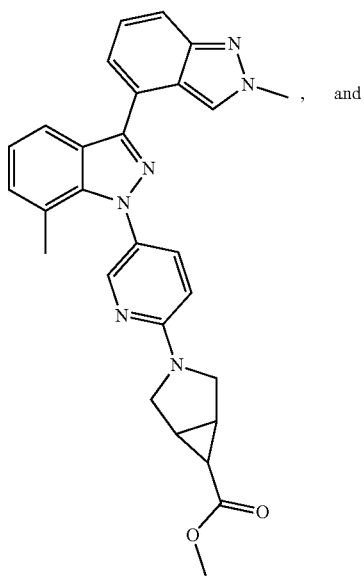
, and

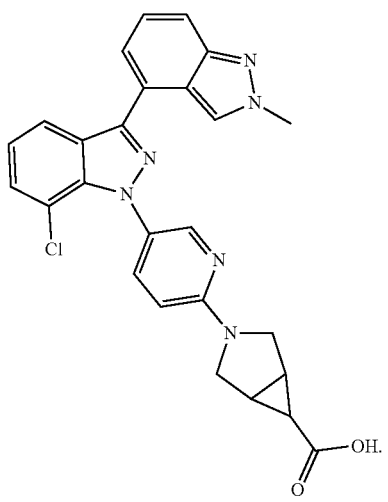
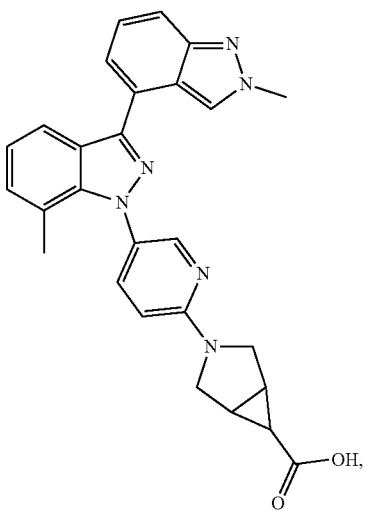
Another particular embodiment of the invention relates to compounds of formula (I) or salts thereof selected from among the group consisting of
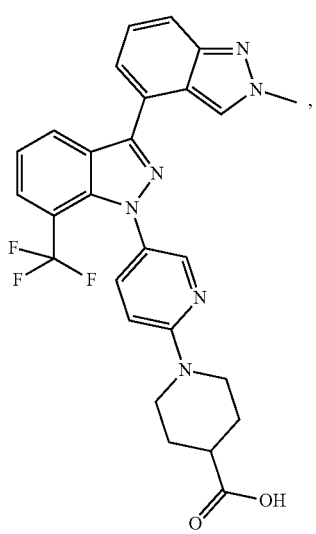
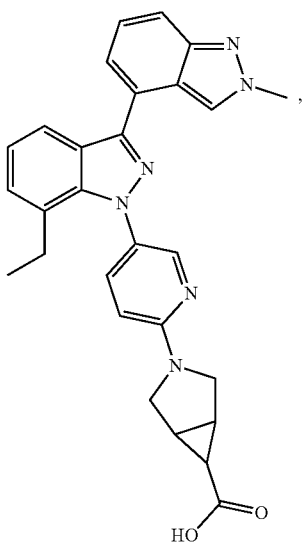
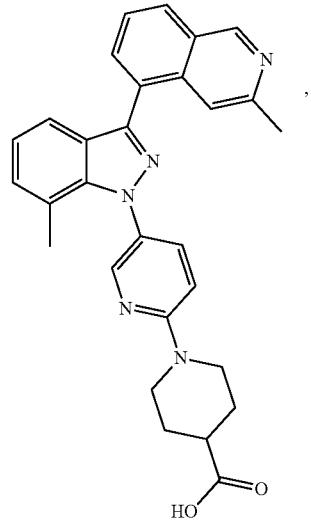
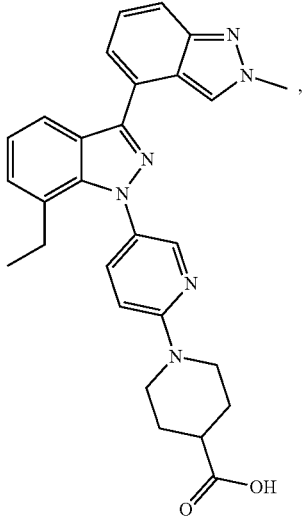

37
-continued
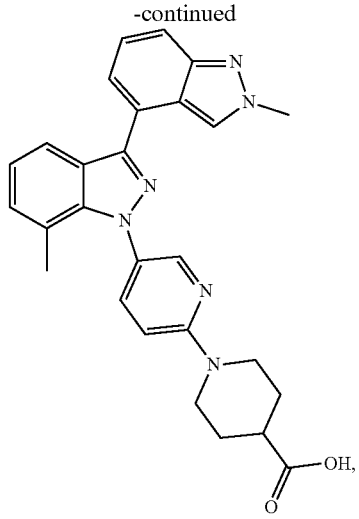
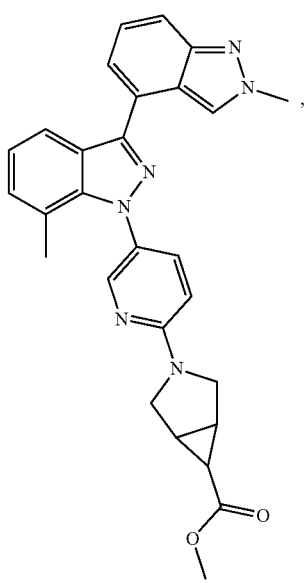
38
-continued
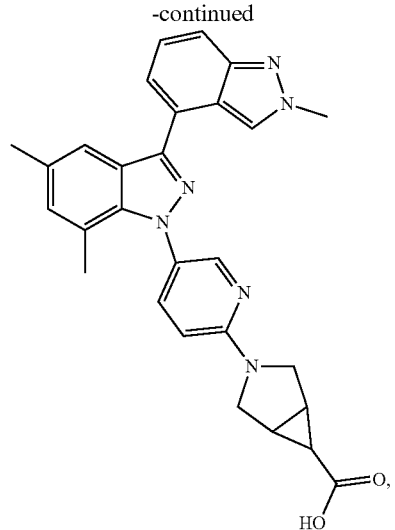
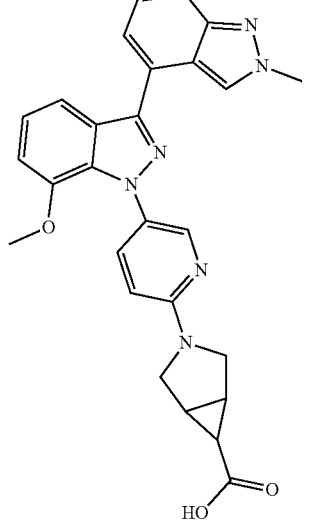
and
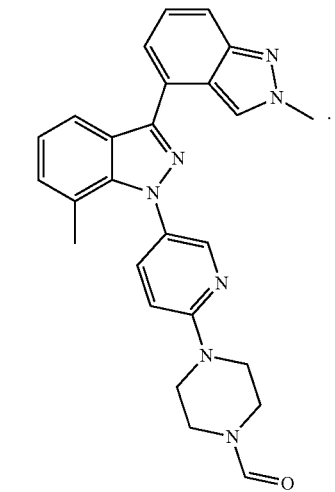

In one aspect, the invention relates to relates to compounds of formula (I) or salts thereof,

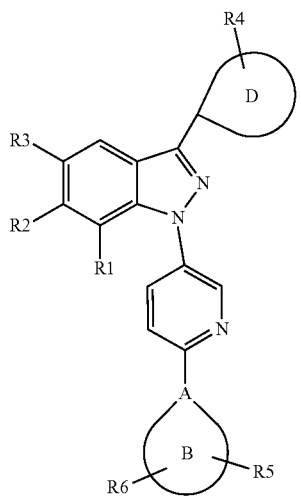

(I)

Wherein, as depicted in the structural representation of formula (I), A is part of B, i.e. B includes A. For example, when A is a heteroatom, this heteroatom could be the sole heteroatom of B, when B is a heterocyclyl. Also, for example, if B is a heterocyclyl defined by a certain number of members (e.g. 5-7-membered, 6-membered, etc.), A is one of such members. Also, as another example, if B is a 6-membered monocyclic heterocyclyl containing 1 N-atom, then A can be this N-atom.

In one aspect, the invention relates to compounds of formula (I) or salts thereof, wherein, B is a group selected from among —$C_{1-4}$-alkylene-pyrimidine and —$C_{1-4}$-alkylene-O—$C_{1-3}$-alkyl, provided that A is nitrogen.

Any and each of the definitions of A, B, D, $R^1$, $R^2$, $R^3$, $R^4$, $R^5$, $R^{5.1}$, $R^{5.2}$, $R^{5.3}$, $R^6$ may be combined with each other.

In one aspect, the invention relates to compounds of formula (I) in their salt free forms.

In one aspect, the invention relates to compounds of formula (I) or a pharmaceutically acceptable salt thereof for use as a medicament. In one aspect, the invention relates to compounds of formula (I) or a pharmaceutically acceptable salt thereof for use in the treatment of a disease selected from among the group consisting of inflammation, allergic or autoimmune diseases, infectious diseases and cancer or for use as vaccine adjuvants. In one aspect, the invention relates to compounds of formula (I) or a pharmaceutically acceptable salt thereof and a pharmaceutically acceptable carrier. In one aspect, the invention relates to compounds of formula (I) or a pharmaceutically acceptable salt thereof as further active substances a substance selected from the group consisting of cytostatic substances, cytotoxic substances, cell proliferation inhibitors, anti-angiogenic substances, steroids, viruses, immunogenic cell death inducers, cancer targeting agents, immuno-modulating agents, antibodies and nanobodies.

Method of Treatment

In another aspect of the present invention, it is found that compounds of general formula (I) or salts thereof may be useful in the prevention and/or for the treatment of diseases and/or conditions wherein the modulation of STING is of therapeutic benefit. Furthermore, due to their activity the compounds of the present invention are suitable as vaccine adjuvants.

Diseases and conditions associated with or modulated by STING embrace, but are not limited to inflammation, allergic or autoimmune diseases, for example allergic rhinitis or asthma, infectious diseases or cancer.

Autoimmune diseases include, but are not limited to systemic lupus erythematosus, psoriasis, insulin-dependent diabetes mellitus (IDDM), dermatomyositis and Sjogren's syndrome (SS).

The compounds of the invention may be used to treat inflammation of any tissue and organs of the body, including but not limited to musculoskeletal inflammation, vascular inflammation, neural inflammation, digestive system inflammation, ocular inflammation, inflammation of the reproductive system, and other inflammation.

Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic). Examples of ocular inflammation which may be treated with the compounds of the invention include blepharitis, blepharochalasis, conjunctivitis, dacryoadenitis, keratitis, keratoconjunctivitis sicca (dry eye), scleritis, trichiasis, and uveitis. Examples of inflammation of the nervous system which may be treated with the compounds of the invention include encephalitis, Guillain-Barre syndrome, meningitis, neuromyotonia, narcolepsy, multiple sclerosis, myelitis and schizophrenia. Examples of inflammation of the vasculature or lymphatic system which may be treated with the compounds of the invention include arthrosclerosis, arthritis, phlebitis, vasculitis, and lymphangitis. Examples of inflammatory conditions of the digestive system which may be treated with the compounds of the invention include cholangitis, cholecystitis, enteritis, enterocolitis, gastritis, gastroenteritis, inflammatory bowel disease (such as Crohn's disease and ulcerative colitis), ileitis, and proctitis. Examples of inflammatory conditions of the reproductive system which may be treated with the compounds of the invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The compounds may be used to treat autoimmune conditions having an inflammatory component. Such conditions include acute disseminated alopecia universalis, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, Goodpasture's syndrome. Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, multiple sclerosis, myasthenia gravis, opsoclonus myoclonus syndrome, optic neuritis, Ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

The compounds may be used to treat T-cell mediated hypersensitivity diseases having an inflammatory component. Such conditions include contact hypersensitivity, contact dermatitis (including that due to poison ivy), urticaria, skin allergies, respiratory allergies (hayfever, allergic rhinitis) and gluten-sensitive enteropathy (Celiac disease).

Other inflammatory conditions which may be treated with the compounds include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, pericarditis, peritonitis, pharyngitis, pleuritis, pneumonitis, prostatitis, pyelonephritis, and stomatitis, transplant rejection (involving organs such as kidney, liver, heart, lung, pancreas (e.g., islet cells), bone marrow, cornea, small bowel, skin allografts, skin homografts, and heart valve xenografts, serum sickness, and graft vs host disease), acute pancreatitis, chronic pancreatitis, acute respiratory distress syndrome. Sexary's syndrome, congenital adrenal hyperplasia, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis. Type 1 diabetes, asthma, inflammatory bowel disease, systemic lupus erythematosis, psoriasis, chronic pulmonary disease, and inflammation accompanying infectious conditions (e.g., sepsis).

In one aspect the disease or condition to be treated using compounds of the invention is cancer. Examples of cancer diseases and conditions in which compounds of formula (I), or salts or solvates thereof may have potentially beneficial anti-tumor effects include, but are not limited to, cancers of the lung, bone, pancreas, skin, brain, head, neck, uterus, ovaries, stomach, colon, colorectal, breast, esophagus, small intestine, bowel, endocrine system, thyroid gland, parathyroid gland, adrenal gland, urethra, prostate, penis, testes, ureter, bladder, kidney or liver, bile duct; urothelial cancer; rectal cancer; cancer of the anal region; carcinomas of the fallopian tubes, endometrium, cervix, vagina, vulva, renal pelvis, renal cell; sarcoma; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hanlartoma; mesothelioma; Hodgkin's Disease or a combination of one or more of the foregoing cancers.

Preferred cancers, which may be treated with compounds according to the invention, are skin, lung, e.g. small-cell lung cancer, non-small cell lung cancer, liver, pancreas, colon, colorectal, brain, breast, ovary, prostate, kidney, bladder, bile duct, endometrium, thyroid gland, cervix, stomach, head, neck, sarcoma, sarcoma of soft tissue, esophagus, head-and-neck-cancer, rectal and urothelial cancer, as well as lymphoma.

The new compounds may be used for the prevention, palliative, curative or semi-curative, short-term or long-term treatment of the above-mentioned diseases, optionally also in combination with surgery, radiotherapy or other "state-of-the-art" compounds, such as e.g. cytostatic or cytotoxic substances, cell proliferation inhibitors, anti-angiogenic substances, steroids, antibodies, nanobodies, cancer-targeting agents, viruses, including but not limited to oncolytic viruses, or immunogenic cell death inducers.

The new compounds may also be used for the prevention, palliative, curative or semi-curative, short-term or long-term treatment of the above-mentioned diseases by combining different administration routes, e.g. intravenous, intratumoral, subcutaneous, inhalative, oral etc. for the compounds, optionally also in combination with surgery, radiotherapy or other "state-of-the-art" compounds, such as e.g. cytostatic or cytotoxic substances, cell proliferation inhibitors, anti-angiogenic substances, steroids, antibodies, nanobodies, cancer-targeting agents, viruses, including but not limited to oncolytic viruses, or immunogenic cell death inducers. Merely as an example of surgery, partial or complete tumor excision may be combined with the compounds of the invention. Merely as an example of radiotherapy, external beam radiotherapy may be combined with the compounds of the invention.

In their role as adjuvants, in certain embodiments the present compounds and compositions may be used as adjuvants in a therapeutic or prophylactic strategy employing vaccine(s).

Thus, the compounds of the present invention, or salts thereof, may be used together with one or more vaccines selected to stimulate an immune response to one or more predetermined antigens. The compounds of the present invention, or salts thereof, may be provided together with, or in addition to, such vaccines.

Such vaccine(s) can comprise inactivated or attenuated bacteria or viruses comprising the antigens of interest, purified antigens, live viral or bacterial delivery vectors recombinantly engineered to express and/or secrete the antigens, antigen presenting cell (APC) vectors comprising cells that are loaded with the antigens or transfected with a composition comprising a nucleic acid encoding the antigens, liposomal antigen delivery vehicles, or naked nucleic acid vectors encoding the antigens. This list is not meant to be limiting. By way of example, such vaccine(s) may also comprise an inactivated tumor cell or an oncolytic virus that expresses and secretes one or more of GM-CSF, CCL20, CCL3, IL-12p70, FLT-3 ligand, cytokines.

Accordingly, the present invention relates to a compound of general formula (I) for use as a medicament or vaccine adjuvants.

In a further aspect the invention provides new compounds of formula (I), including salts thereof, for use in a method for the treatment of a disease or condition associated with or modulated by STING.

In a further aspect the invention provides new compounds of formula (I), or salts thereof, for the treatment of inflammation, allergic or autoimmune diseases, for example allergic rhinitis or asthma, for the treatment of infectious diseases or of cancer, or for the use as vaccine adjuvants.

Furthermore, the present invention relates to the use of a compound of general formula (I) for the treatment and/or prevention of a disease and/or condition associated with or modulated by STING. Diseases and conditions associated with or modulated by STING embrace, but are not limited to inflammation, allergic or autoimmune diseases, for example allergic rhinitis or asthma, infectious diseases or cancer, including but not limited to the specific diseases as mentioned above. Furthermore, due to their activity the compounds of the present invention are suitable as vaccine adjuvants, including but not limited to the specific applications as mentioned above.

Accordingly, the present invention relates to a compound of general formula (I) for use as a medicament or vaccine adjuvants.

Furthermore, the present invention relates to the use of a compound of general formula (I) for the treatment and/or prevention of above-mentioned diseases and conditions.

In a further aspect the present invention relates to a compound of general formula (I) for use in the treatment and/or prevention of above-mentioned diseases and conditions.

In a further aspect the present invention relates to a compound of general formula (I) for use in the treatment and/or prevention of above-mentioned cancers, before or after tumor excision and/or radiotherapy.

In a further aspect the present invention relates to the use of a compound of general formula (I) for the preparation of a medicament for the treatment and/or prevention of above-mentioned diseases and conditions.

In a further aspect the present invention relates to methods of treatment or prevention of above-mentioned diseases and conditions, which method comprises the administration of an effective amount of a compound of general formula (I) to a human being.

The dose range of the compounds of general formula (I) applicable per day is usually from 0.00001 to 100 mg per kg body weight, for example from 0.00001 to 10 mg per kg body weight of the patient. Each dosage unit may conveniently contain from 0.001 to 1000 mg, for example from 0.001 to 100 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

In a related aspect, the present invention relates to methods of inducing, stimulating, or adjuvanting an immune response in an individual. These methods comprise administering the compounds of the present invention, to the individual.

In a further aspect the invention provides the use of a compound of general formula (I), for the manufacture of an immunogenic composition comprising an antigen or antigen composition, for the treatment or prevention of a disease.

In a further aspect the invention provides a method of treating or preventing a disease comprising the administration to a human subject suffering from or susceptible to a disease, an immunogenic composition comprising an antigen or antigen composition and a compound of general formula (I).

In a further aspect the invention provides a vaccine composition comprising an antigen or antigen composition and a compound of general formula (I), for use in the treatment or prevention of a disease.

In a further aspect the invention provides the use of a compound of general formula (I), for the manufacture of a vaccine composition comprising an antigen or antigen composition, for the treatment or prevention of a disease.

In a further aspect the invention provides a method of treating or preventing a disease comprising the administration to a human subject suffering from or susceptible to disease, a vaccine composition comprising an antigen or antigen composition and a compound of general formula (I).

Pharmaceutical Compositions

In another aspect of the present invention, it is found that pharmaceutical compositions of the above-mentioned compounds may be formulated that are suitable for the administration of therapeutically effective amounts of said compounds. Suitable preparations for administering the compounds of formula (I) will be apparent to those with ordinary skill in the art and include for example tablets, pills, capsules, suppositories, lozenges, troches, solutions, syrups, elixirs, sachets, injectable solutions (subcutaneously, intravenously, intramuscularly, intra-peritoneal, intra-tumorally and peri-tumorally), inhalables, infusions, elixirs, emulsions, and powders. Furthermore, the compounds according to the invention may be administered via targeted delivery platforms, for example such targeted delivery platforms may be antibody-drug conjugates, nanobody-drug conjugates, peptide-drug conjugates, virus-like particles, or nanoparticle formulations.

Suitable tablets may be obtained, for example, by mixing one or more compounds according to formula I with known excipients, for example inert diluents, carriers, disintegrants, adjuvants, surfactants, binders and/or lubricants.

For the purposes of this disclosure, the pharmaceutical compositions may be administered by a variety of means, including non-parenterally, parenterally, by inhalation spray, topically, nasally, orally, or rectally in formulations containing pharmaceutically acceptable carriers, adjuvants and vehicles. The pharmaceutical compositions of the disclosure may be administered in the form of a sterile injectable preparation, such as a sterile injectable aqueous or oleaginous suspension.

According to another embodiment, a vaccine comprising one or more compounds of general formula (I), is provided. In a further aspect the invention provides a vaccine adjuvant comprising a compound of general formula (I). In a further aspect the invention provides an immunogenic composition comprising an antigen or antigen composition and a compound of general formula (I).

In a further aspect the invention provides an immunogenic composition comprising an antigen or antigen composition and a compound of general formula (I) for use in the treatment or prevention of a disease.

Combination Therapy

The compounds of the invention may be used on their own or may be combined with pharmaceutically acceptable excipients, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression.

In certain embodiments, the compounds and compositions thereof described herein are administered in conjunction with one or more additional compositions including vaccines intended to stimulate an immune response to one or more predetermined antigens; adjuvants; CTLA-4 and PD-1 pathway antagonists, lipids, liposomes, chemotherapeutic agents, immunomodulatory cell lines, cancer-targeting agents, immunogenic cell-death inducers, immuno-modulating agents, wherein the immunomodulating agents may be understood as agents of a general activation-modulation type in general as well as agents modulating and/or increasing the frequency of a certain immune cell subtype, etc.

The compounds and compositions thereof described herein may be administered before, after, and/or simultaneously with an additional therapeutic or prophylactic composition or modality.

The compounds, compositions, including any combinations with one or more additional therapeutic agents, according to the invention may be administered by mucosal (e.g. oral, sublingual, vaginal, nasal, cervical, etc.), intra-tumoral, intra-peritoneal, peri-tumoral, transdermal, inhalative, or parenteral (e.g. subcutaneous, intravenous, intramuscular, intraarterial, intradermal, intrathecal and epidural administrations) route.

Furthermore, the compounds, compositions, including any combinations with one or more additional therapeutic agents, according to the invention may be administered via targeted delivery platforms, for example such targeted delivery platforms can be antibody-drug conjugates, nanobody-drug conjugates, peptide-drug conjugates, virus-like particles, or nanoparticles.

Of the possible methods of administration, intra-peritoneal, intra-tumoral, peri-tumoral, subcutaneous, inhalative or intravenous administration is preferred. The compounds, compositions, including any combinations with one or more additional therapeutic agents, according to the invention may also be administered before, after, and/or simultaneously by a combination of different methods of administration. Simply by way of an example, an inhalative or intravenous administration may be followed by an intra-tumoral or peri-tumoral administration or an intra-tumoral or peri-tumoral administration may be followed by an inhalative or intravenous administration. Additionally, such an administration of the compounds via different routes may be before or after additional therapeutic step, such as tumor excision or radiotherapy. Simply by way of an example, the compounds of the invention may be administered after radiotherapy. Furthermore, the compounds of the invention may be given by intravenous administration after radiotherapy. Furthermore, the compounds of the invention may be given by intravenous administration after tumor excision. Furthermore, the compounds of the invention may be given by intra-tumoral administration after radiotherapy. Furthermore, the compounds of the invention may be given by peri-tumoral administration after radiotherapy. Furthermore, the compounds of the invention may be given by inhalative administration after tumor excision. Furthermore, the compounds of the invention may be given by intravenous administration, followed by intra-tumoral administration, and both administrations take place after radiotherapy. Furthermore, the compounds of the invention may be given by intra-tumoral administration, followed by intravenous administration, and both administrations take place after radiotherapy. Furthermore, the compounds of the invention may be given by intravenous administration, followed by peri-tumoral administration, and both administrations take place after radiotherapy. Furthermore, the compounds of the invention may be given by peri-tumoral administration, followed by intravenous administration, and both administrations take place after radiotherapy.

Methods for co-administration with an additional therapeutic agent are well known in the art.

Because of the adjuvant properties of the compounds of the present invention, their use may also combined with other therapeutic modalities including other vaccines, adjuvants, antigen, antibodies, and immune modulators.

In addition to the compounds of the present invention and compositions thereof described herein, the compositions or methods of the present invention may further comprise one or more additional substances which, because of their nature, can act to stimulate or otherwise utilize the immune system to respond to the cancer antigens present on the targeted tumor cell(s).

The compounds of the present invention can be used in combination with an immune checkpoint inhibitor, such as an immune checkpoint inhibitor selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, or a TIGIT pathway antagonist.

The compounds of the present invention can be used in combination with an immuno-oncological agonist in combination with a T-cell receptor agonist, or in combination with a TNF receptor superfamily agonist or antagonist.

The compounds of the present invention can be used in combination with therapeutic antibodies or therapeutic nanobodies. In some embodiments, the mechanism of action of the therapeutic antibody is Antibody-Dependent Cell-Mediated Cytotoxicity (ADCC).

In additional embodiments of the methods described herein, the compounds of the present invention are used in combination with chemotherapeutic agents (e.g. small molecule pharmaceutical compounds) as known to the skilled person. Thus the methods further involve administering to the subject an effective amount of one or more chemotherapeutic agents as an additional treatment or a combination treatment.

Additional pharmacologically active substance(s) which can also be used together/in combination with the compound of formula (I)—or a pharmaceutically acceptable salt thereof—(including all individual embodiments or generic subsets of compounds (I)) or in the medical uses, uses, methods of treatment and/or prevention as herein (above and below) disclosed include, without being restricted thereto: hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide); aromatase inhibitors (e.g. anastrozole, letrozole, liarozole, vorozole, exemestane, atamestane); LHRH agonists and antagonists (e.g. goserelin acetate, luprolide); inhibitors of growth factors and/or of their corresponding receptors (growth factors are for example: platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4),) and/or their corresponding receptors; inhibitors are for example (anti-)growth factor antibodies, (anti-)growth factor receptor antibodies and tyrosine kinase inhibitors, such as for example afatinib, dacomitinib, canertinib, neratinib, avitinib, poziotinib, AV 412, PF-6274484, HKI 357, olmutinib, osimertinib, almonertinib, nazartinib, lazertinib, pelitinib, erlotinib, gefitinib, icotinib, sapitinib, lapatinib, varlitinib, vandetanib, TAK-285, AEE788, BMS599626/AC-480, GW 583340, necitumumab, panitumumab, cetuximab, amivantanab, pertuzumab, trastuzumab, trastuzumab emtansine, or inhibitors of mutant EGFR, an inhibitor of HER2 with exon 20 mutations, and hepatocyte growth factor (HGF, c-MET, e.g. emibetuzumab, amivantanab, savolitinib, cabozantinib, foretinib); antimetabolites (e.g. methotrexate, raltitrexed, 5-fluorouracil (5-FU), capecitabine, floxuridine, gemcitabine, mercaptopurine, thioguanine, cladribine, pentostatin, cytarabine (ara C), fludarabine, combination of trifluridine and tipiracil (=TAS102)); antitumor antibiotics (e.g. anthracyclins such as doxorubicin, doxil (pegylated liposomal doxorubicin hydrochloride), myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids e.g. vinblastine, vindesin, vinorelbin and vincristine; and taxanes such as paclitaxel, docetaxel, nab-paclitaxel (Abraxane)); angiogenesis inhibitors (e.g. tasquinimod, bevacizumab), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone); serine/threonine kinase inhibitors (e.g. PDK 1 inhibitors, Raf inhibitors, A-Raf inhibitors, B-Raf inhibitors, C-Raf inhibitors, mTOR inhibitors (e.g. rapamycin, temsirolimus, everolimus, ridaforolimus, zotarolimus, sapanisertib, Torin 1, dactosilib, GDC-0349, vs-5584; vistusertib; AZD8055), mTORC1/2 inhibitors, PI3K inhibitors, PI3Kα inhibitors (e.g. alpelisib, serabelisib, GDC-0077, HH-CYH33, AMG 511, buparlisib, dactolisib, pictilisib, taselisib), dual mTOR/PI3K inhibitors, STK 33 inhibitors, AKT inhibitors, PLK 1 inhibitors, inhibitors of CDK4/6 (e.g. palbociclib, ribociclib, abemaciclib, trilaciclib, PF-06873600), Aurora kinase inhibitors); tyrosine kinase inhibitors (e.g. PTK2/FAK inhibitors); protein protein interaction inhibitors (e.g. IAP inhibitors/SMAC mimetics, MCL-1 (e.g. AZD-5991, AMG176, AMG-397, 564315, S63845, A-1210477), MDM2, MDM2/MDMX); MEK inhibitors (e.g. trametinib, cobimetinib, binimetinib, selumetinib, refametinib); SOS1-inhibitor (i.e. a compound that modulates/inhibits the GEF functionality of SOS1, e.g. by binding to SOS1 and preventing protein-protein interaction between SOS1 and a (mutant) Ras protein, e.g. KRAS; e.g. BAY-293), an inhibitor of GDP-loaded or GTP-loaded RAS and/or of any mutants thereof (i.e. a compound that modulates/inhibits the functionality of (mutant) RAS protein by, e.g., binding to GDP-loaded or GTP-loaded (mutant) RAS protein, e.g. KRAS, NRAS and/or HRAS, preferably KRAS); an irreversible inhibitor of KRAS G12C (AMG510, MRTX849, ARS-324, GDC-6036); a reversible or irreversible binder to GDP-loaded (mutant) KRAS; a reversible or irreversible binder to GTP-loaded (mutant) KRAS; ALK inhibitors (e.g. crizotinib, alectinib, entrectinib, brigatinib, ceritinib); ERK inhibitors; FLT3 inhibitors; BRD4 inhibitors; IGF-1R inhibitors; TRAILR2 agonists; Bcl-xL inhibitors; Bcl-2 inhibitors (e.g. venetoclax, obatoclax, navitoclax, oblimersen); Bcl-2/Bcl-xL inhibitors; ErbB receptor inhibitors; BCR-ABL inhibitors; ABL inhibitors; Src inhibitors (e.g. dasatinib, ponatinib, bosutinib, vandetanib, KX-01, saracatinib, KX2-391, SU 6656, WH-4-023); rapamycin analogs (e.g. everolimus, temsirolimus, ridaforolimus, sirolimus); androgen synthesis inhibitors; androgen receptor inhibitors; DNMT inhibitors; HDAC inhibitors; ANG1/2 inhibitors; histone deacetylase inhibitor; an inhibitor of IL6; inhibitor of JAK and/or any mutants thereof; an inhibitor of A-Raf and/or B-Raf and/or C-Raf and/or any mutants thereof (encorafenib, dabrafenib, vemurafenib, PLX-8394, RAF-709 (=example 131 in WO 2014/151616), LXH254, sorafenib, LY-3009120 (=example 1 in WO 2013/134243), lifirafenib, TAK-632, agerafenib, CCT196969, RO5126766, RAF265); an inhibitor of a receptor tyrosine kinase (RTK) and/or of any mutants thereof; an inhibitor of SHP2 and/or of any mutants thereof (e.g. SHP099, TNO155, RMC-4550, RMC-4630, IACS-13909); CYP17 inhibitors; radiopharmaceuticals; proteasome inhibitors (e.g. carfilzomib); immunotherapeutic agents such as immune checkpoint inhibitors (e.g. CTLA4, PD1, PD-L1, PD-L2, LAG3, SIRPalpha-antibodies, and TIM3 binding molecules/immunoglobulins (ipilimumab, nivolumab, pembrolizumab, tislelizumab, atezolizumab, avelumab, durvalumab, pidilizumab, PDR-001 (=spartalizumab), AMG-404, ezabenlimab, sintilimab, camrelizumab, toribalimab, tislelizumab,); ADCC (antibody-dependent cell-mediated cytotoxicity) enhancers (e.g. anti-CD33 antibodies, anti-CD37 antibodies, anti-CD20 antibodies); T-cell engagers, e.g. PSMA×CD3, B7H6/CD3 (as e.g. disclosed in WO2021/064137), DLL3/CD3 (as e.g. disclosed in WO2019/234220), e.g. bi-specific T-cell engagers (BiTEs®) like e.g. CD3×BCMA, CD3×CD33, CD3×CD19), cancer vaccines, MDM2-inhibitors, oncolytic viruses and various chemotherapeutic agents such as amifostin, anagrelid, clodronat, filgrastin, interferon, interferon alpha, leucovorin, procarbazine, levamisole, mesna, mitotane, pamidronate and porfimer. The compounds of the present invention can be used in combination with an OX40 agonist, an ICOS-ligand, a CD27 agonist, a GITR agonist, a Toll like receptor agonist.

In a preferred embodiment, additional pharmacologically active substance(s) which can also be used together/in combination with the compound of formula (I)—or a pharmaceutically acceptable salt thereof—(including all individual embodiments or generic subsets of compounds (I)) or in the medical uses, uses, methods of treatment and/or prevention as herein (above and below) disclosed include check-point inhibitors (ipilimumab, nivolumab, pembrolizumab, tislelizumab, atezolizumab, avelumab, durvalumab, pidilizumab, PDR-001 (=spartalizumab), AMG-404, ezabenlimab, sintilimab, camrelizumab, toribalimab, tislelizumab), taxanes (paclitaxel, docetaxel, nab-paclitaxel (Abraxane)), T-cell-engagers e.g. PSMA×CD3, B7H6/CD3 (as e.g. disclosed in WO2021/604137), DLL3/CD3 (as e.g. disclosed in WO2019/234220), e.g. bi-specific T-cell engagers (BiTEs®) like e.g. CD3×BCMA, CD3×CD33, CD3×CD19, cancer vaccines, MDM2-inhibitors, and oncolytic viruses.

In additional embodiments of the methods described herein, the compounds of the present invention are used in combination with chemotherapeutic agents and/or additional agents e.g. cancer-targeting therapies, for treating the indications as described in the methods herein. Thus the methods further involve administering to the subject an effective amount of one or more cancer-targeting agents as an additional treatment or a combination treatment. In additional embodiments the methods described herein, the compounds of the present invention are used in combination with chemotherapeutic agents and/or additional agents for treating the indications as described in the methods herein and/or additional therapies such as radiotherapy and/or tumor excision.

In yet another aspect the present invention relates a method for treating a disease or condition associated with or modulated by STING in a patient that includes the step of administering to the human patient in need of such treatment a therapeutically effective amount of a compound of the present invention in combination with a therapeutically effective amount of one or more additional therapeutic agents described hereinbefore.

The use of the compound according to the invention in combination with the additional therapeutic agent may take place simultaneously or at staggered times.

The compound according to the invention and the one or more additional therapeutic agents may both be present together in one formulation or separately in two identical or different formulations, for example as a so-called kit-of-parts.

Thus, in a further aspect the present invention provides a combination comprising a compound of general formula (I), and at least one further therapeutic agent.

A further aspect of the present invention is to provide a pharmaceutical composition comprising a compound of formula (I), or a pharmaceutically acceptable salt thereof, and at least one further therapeutic agent and one or more of pharmaceutically acceptable excipients.

In a further aspect the invention provides a combination comprising a compound of formula (I), or a pharmaceutically acceptable salt thereof, and at least one further therapeutic agent for use in therapy.

In a further aspect the invention provides a combination comprising a compound of formula (I), or a pharmaceutically acceptable salt thereof, and at least one further therapeutic agent for use in the treatment of a disease or condition in which modulation of STING is beneficial.

In a further aspect the invention provides a combination comprising a compound of formula (I), or a pharmaceutically acceptable salt thereof, and at least one further therapeutic agent for use in the treatment of inflammation, allergic and autoimmune diseases, infectious diseases and cancer.

In a further aspect the invention provides a method of treatment of a disease or condition in which modulation of STING is beneficial, in a patient, comprising administering a therapeutically effective amount of a combination comprising a compound of formula (I), or a pharmaceutically acceptable salt thereof, and at least one further therapeutic agent.

In a further aspect the invention provides a method of treatment of inflammation, allergic or autoimmune diseases, infectious diseases or cancer, in a patient, comprising administering a therapeutically effective amount of a combination comprising a compound of formula (I), or a pharmaceutically acceptable salt thereof, and at least one further therapeutic agent.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

In another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

Chemical Synthesis

| LIST OF ABBREVIATIONS | |
| --- | --- |
| ACN | acetonitrile |
| A.M. | Analytical method |
| Bu | butyl |
| conc. | concentrated |
| d | day(s) |
| DCM | dichloromethane |
| DIPEA | diisopropylethyl amine |
| DMA | N,N-dimethylacetamide |
| DMAP | N,N-dimethylpyridin-4-amine |
| DMF | N,N-dimethyl formamide |
| DMSO | dimethylsulphoxide |
| Et | ethyl |
| EtOAc | ethyl acetate |
| h | hour(s) |
| HATU | N-[(dimethylamino)-(1H-1,2,3-triazolo[4,5-b]pyridin-1-yl)-methylene]-N-methylmethan-aminium hexafluorophosphate N-oxide |
| HPLC | high performance liquid chromatography |
| iPr | isopropyl |
| M | molar |
| m.p. | melting point |
| Me | methyl |
| min | minute(s) |
| mL | millilitre |
| MS | mass spectrometry |
| N | normal |
| NMP | N-methylpyrrolindinone |
| NMR | nuclear resonance spectroscopy |
| NP | normal phase |
| ppm | part per million |
| prep | preparative |
| $R_f$ | retention factor |
| RP | reversed phase |
| RT | room temperature |
| tert | tertiary |
| TBDMS | tert-butyldimethylsilyl |
| TFA | trifluoroacetic acid |
| THF | tetrahydrofuran |
| TLC | thin layer chromatography |
| tR | retention time |

Other features and advantages of the present invention will become apparent from the following more detailed examples which exemplarily illustrate the principles of the invention without restricting its scope.

General

Unless stated otherwise, all the reactions are carried out in commercially obtainable apparatuses using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with IUPAC guidelines. If a compound is to be represented both by a structural formula and by its nomenclature, in the event of a conflict the structural formula is decisive.

Chromatography

Thin layer chromatography is carried out on ready-made TLC plates of silica gel 60 on glass (with fluorescence indicator F-254) made by Merck.

A Biotage Isolera Four apparatus is used for automated preparative NP chromatography together with Interchim Puri Flash columns (50 µm, 12-300 g) or glass columns filled with silica gel made by Millipore (Granula Silica Si-60A 35-70 µm).

Preparative RP HPLC is carried out with columns made by Waters (Sunfire C18, 10 μm, 30×100 mm Part. No. 186003971 or X-Bridge C18, 10 μm, 30×100 mm Part. No. 186003930). The compounds are eluted using either different gradients of $H_2O$/acetonitrile or $H_2O$/MeOH, where 0.2% HCOOH is added to the water, or with different gradients utilizing a basic aqueous buffer solution (1 L water contains 5 mL of an ammonium hydrogencarbonate solution (158 g per 1 L $H_2O$) and 2 mL ammonia (7 mol/l solution in MeOH)) instead of the water-HCOOH-mixture.

The analytical HPLC (reaction monitoring) of intermediate compounds is carried out with columns made by Waters and Phenomenex. The analytical equipment is also provided with a mass detector in each case.

HPLC Mass Spectroscopy/UV Spectrometry

The retention times/MS-ESI$^+$ for characterizing the example compounds according to the invention are determined using an HPLC-MS apparatus (high performance liquid chromatography with mass detector) e.g. made by Agilent. Compounds that elute at the injection peak are given the retention time tR=0.

Analytical HPLC Methods (A.M.)

Method_1
HPLC: Agilent 1100/1200 Series
MS: Agilent LC/MSD SL
Column: Waters X-Bridge BEH C18, 2.5 μm, 2.1×30 mm XP
Eluant: A: 5 mM $NH_4HCO_3$/19 mM $NH_3$ in $H_2O$; B: ACN (HPLC grade)
Detection: MS: Positive and negative mode
Mass range: 100-800 m/z
Flow: 1.4 ml/min
Column temp.: 45° C.
Gradient: 0.00-0.01 min: 5% B
 0.01-1.00 min: 5%→100% B
 1.00-1.37 min: 100% B
 1.37-1.40 min: 100%→5% B Method_2
HPLC: Agilent 1100/1200 Series
MS: Agilent LC/MSD (API-ES+/−3000 V, Quadrupol, G6140)
Column: Waters, XBridge C18, 2.5 μm, 2.1×20 mm column
Solvent: A: 20 mM $NH_4HCO_3$/$NH_3$ in $H_2O$ pH 9; B: ACN (HPLC grade)
Detection: MS: positive and negative mode
Mass range: 120-900 m/z
Flow: 1.00 m/min
Column temp.: 60° C.
Gradient: 0.00-1.50 min: 10%→95% B
 1.50-2.00 min: 95% B
 2.00-2.10 min: 95%→10% B Method_3
HPLC Agilent 1260 system
MS 1200 Series LC/MSD (MM-ES+APCI+/−3000 V, Quadrupol, G6130)
Column YMC; Part. No. TA12S03-0302WT; Triart C18, 3 μm, 12 nm; 30×2.0 mm column
Eluant A: H2O+0.11% HCOOH; B: MeCN+0.1% HCOOH (HPLC grade)
detection signal UV 254 nm (bandwidth 10, reference off)
Mass range: pos 150-750 m/z
Flow 1.4 mL/min
Column temp.: 45° C.

| Gradient | 0.0-1.0 min | 15% → 100% B |
| --- | --- | --- |
| | 1.0-1.23 min | 100% B |

Method_4
UPLC/MS: Waters Acquity-UPLC-SQ Detector-2
Column: AQUITY UPLC BEH C18 1.7 μm, 2.1×50 mm
Solvent: A: 0.05% HCOOH in ACN; B: $H_2O$+0.05% HCOOH
Detection: MS: positive and negative mode
Mass range: 100-1500 m/z
Flow: 0.6 mL/min
Column temp.: 35° C.
Gradient: 0.00-0.30 min: 97% B
 0.30-2.20 min: 97%→2% B
 2.20-3.30 min: 2% B
 3.30-4.50 min: 2% B
 4.50-4.51 min: 2% B→97% B Method_5
UPLC/MS: Waters Acquity-UPLC-SQ Detector-2
Column: AQUITY UPLC BEH C18 1.7 μm, 2.1×50 mm
Solvent: A: 0.07% HCOOH in ACN; B: $H_2O$+0.07% HCOOH
Detection: MS: positive and negative mode
Mass range: 100-1500 m/z
Flow: 0.6 mL/min
Column temp.: 35° C.
Gradient: 0.00-0.30 min: 97% B
 0.30-2.20 min: 97%→2% B
 2.20-3.30 min: 2% B
 3.30-4.50 min: 2% B
 4.50-4.51 min: 2% B→97% B Method_6
UPLC/MS: Waters Acquity-UPLC-SQ Detector-2
Column: AQUITY UPLC BEH C18 1.7 μm, 2.1×50 mm
Solvent: A: $H_2O$+0.07% HCOOH B: 0.07% HCOOH in ACN
Detection: MS: positive and negative mode
Mass range: 100-1500 m/z
Flow: 0.6 mL/min
Column temp.: 35° C.
Gradient: 0.00-0.30 min: 97% A
 0.30-2.70 min: 97%→2% A
 2.70-3.50 min: 2% A
 3.50-3.51 min: 2%→97% A Method_7
HPLC Agilent 1100/1200 system
MS 1200 Series LC/MSD (MM-ES+APCI+/−3000 V, Quadrupol, G6130B)
Column Waters, Part. No. 186003389, XBridge BEH C18, 2.5 μm, 2.1×30 mm) column
Eluant A: 5 mM $NH_4HCO_3$/18 mM $NH_3$ (pH=9.2); B: ACN (HPLC grade)
detection signal UV 254 nm, 230 nm, 214 nm (bandwidth 8, reference off)
Mass range pos 150-750 m/z
Flow 1.4 mL/min
Column temp. 45° C.

| Gradient | 0.0-1.0 min | 15% → 95% B |
| --- | --- | --- |
| | 1.0-1.3 min | 95% B |

Method_8

HPLC Agilent 1100/1200 system

MS 1200 Series LC/MSD (MM-ES+APCI+/−3000 V, Quadrupol, G6130B)

Column Waters, Part. No. 186003389, XBridge BEH C18, 2.5 μm, 2.1×30 mm) column

Eluant A: 5 mM NH$_4$HCO$_3$/18 mM NH$_3$ (pH=9.2); B: ACN (HPLC grade)

Mass range pos/neg 150-750 detection signal UV 254 nm, 230 nm, 214 nm (bandwidth 8, reference off)

Flow 1.4 mL/min

Column temp. 45° C.

| Gradient | 0.0-1.0 min | 15% → 95% B |
|---|---|---|
| | 1.0-1.3 min | 95% B |

Preparation of the Compounds According to the Invention

The compounds according to the present invention and their intermediates may be obtained using methods of synthesis which are known to the one skilled in the art and described in the literature of organic synthesis. These methods are intended as an illustration of the invention, without restricting its subject matter and the scope of the compounds claimed to these examples. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

One method for the preparation of compounds of formula (I) is exemplified in Scheme I: Indazoles B can be synthesized from ortho-methyl aniline derivatives A. Subsequent iodination leads to 3-iodo-indazoles C. Intermediates D can be obtained e.g. by Chan-Lam coupling utilizing (6-fluoro-pyridin-3-yl)boronic acid. Conversion into intermediates E can be achieved e.g. via Suzuki coupling. Finally, compounds F are synthesized e.g. by nucleophilic aromatic substitution. The products are isolated by conventional means and preferably purified by chromatography.

Scheme I

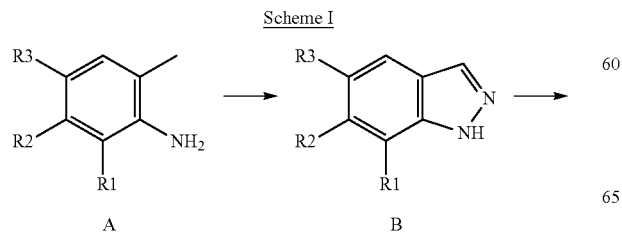

A  B

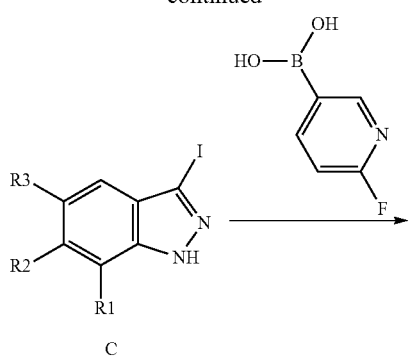

C

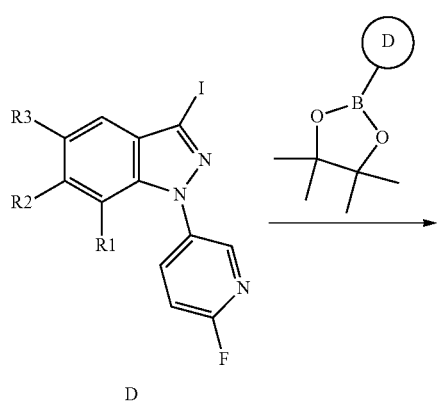

D

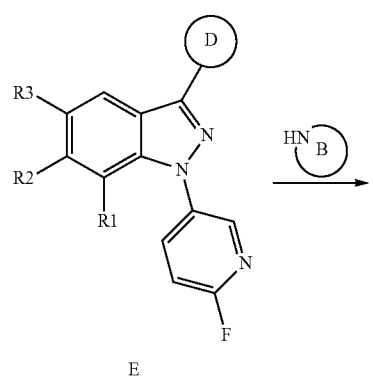

E

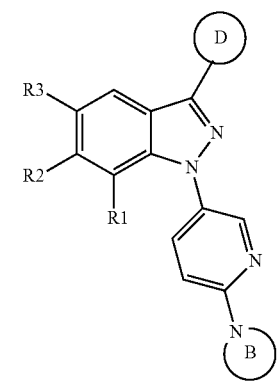

F

Preparation of Intermediates B

B1 7-methyl-6-nitro-1H-indazole

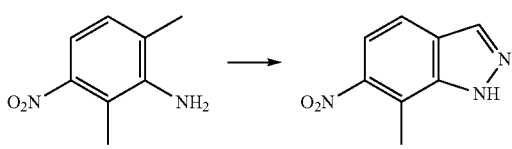

A mixture of 2,6-dimethyl-3-nitro-phenylamine (2.0 g, 12 mmol) in acetic acid (177 ml) is cooled to 5° C. Sodium nitrite (1.08 g, 15.6 mmol) in water (4 ml) is added drop wise. The mixture is stirred for 24 h and concentrated in vacuo. The title compound is obtained by recrystallization from methanol. Yield 0.7 g (34%). HPLC-MS: M+H=178; tR=1.85 min (Method_4)

B2 Methyl 7-methyl-1H-indazole-6-carboxylate

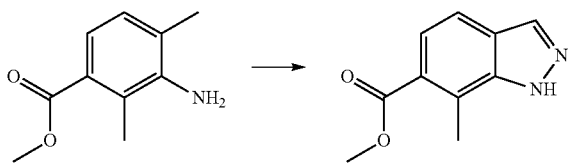

To a mixture of 3-amino-2,4-dimethyl-benzoic acid methyl ester (5.0 g, 27.9 mmol) in water (15 ml) at 0° C. is added aqueous conc. HCl (7 ml) before NaNO₂ (2.3 g, 33.5 mmol in 4 ml of water) is added as well as sodium tetrafluoroborate (4.0 g, 36.3 mmol in 4 ml water). The mixture is stirred for 45 min. The solid is collected by filtration, rinsed with diethylether, dried and taken up in chloroform (40 ml). Under stirring potassium acetate (2.2 g, 22.3 mmol) and 18-Crown-6 (synonym: 1,4,7,10,13,16-Hexaoxacyclooctadecan; 0.22 g, 0.84 mmol) is added and stirring continued at RT for 2 h. Water (70 ml) is added and the mixture is extract with EtOAc. The combined organic layers are dried over MgSO₄, concentrated in vacuo and rinsed with pentane. Yield 3.5 g (66%). HPLC-MS: M+H=191; tR=1.85 min (Method_5)

B3 (7-methyl-1H-indazol-6-yl)methanol

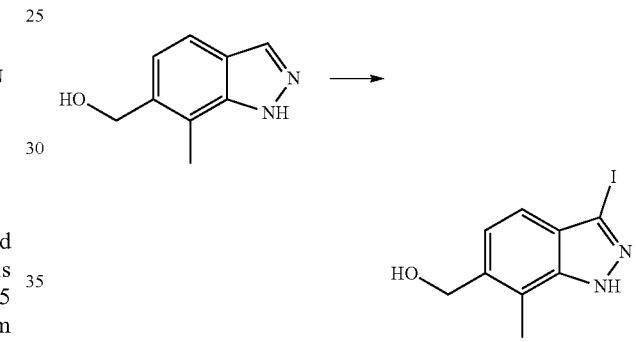

To Methyl 7-methyl-1H-indazole-6-carboxylate B2 (3.5 g, 18.4 mmol) in THF (40 ml) is added lithium aluminium hydride (1.05 g, 27.6 mmol) at 0° C. After stirring at RT for 5 min 4N NaOH aq. (1 ml) is added. The mixture is extracted with EtOAc. The combined organic layers are dried over MgSO₄ and concentrated in vacuo. Yield of crude product: 3.0 g (99%). HPLC-MS: M+H=163; tR=1.47 min (Method_5)

Preparation of Intermediates C

C1 (3-iodo-7-methyl-1H-indazol-6-yl)methanol

To (7-methyl-1H-indazol-6-yl)-methanol B3 (0.35 g, 2.16 mmol) in DMF (6 ml) at 0° C. is added iodine (298 mg, 4.32 mmol) and K₂CO₃ (895 mg, 6.47 mmol). After stirring for 2 h at RT EtOAc (100 ml) is added and the mixture is extracted with water, 10% aqueous Na₂S₂O₃ solution and brine. The combined organic layers are dried over Na₂SO₄ and concentrated in vacuo. Yield of crude product: 0.3 g (48%). HPLC-MS: M+H=289; tR=1.75 min (Method_5)

The following intermediates are prepared analogously from intermediates B:

| # | Structure | IUPAC Name | tR [min] | [M + H] | A.M. |
|---|---|---|---|---|---|
| C2 | 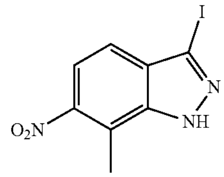 | 3-iodo-7-methyl-6-nitro-1H-indazole | 2.12 | 304 | Method_5 |
| C3 | 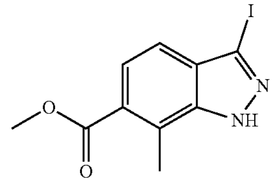 | methyl 3-iodo-7-methyl-1H-indazole-6-carboxylate | 2.13 | 317 | Method_5 |

| # | Structure | IUPAC Name | tR [min] | [M + H] | A.M. |
|---|---|---|---|---|---|
| C4 | 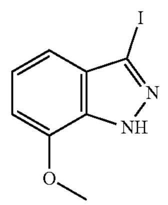 | 3-iodo-7-methoxy-1H-indazole | 0.53 | 275 | Method_7 |
| C5 | 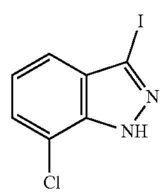 [SMILES: Clc1cccc2c(I)n[nH]c12] | 7-chloro-3-iodo-1H-indazole | 0.919 | 279 | Method_1 |

C6 6-{[(tert-butyldimethylsilyl)oxy]methyl}-3-iodo-7-methyl-1H-indazole

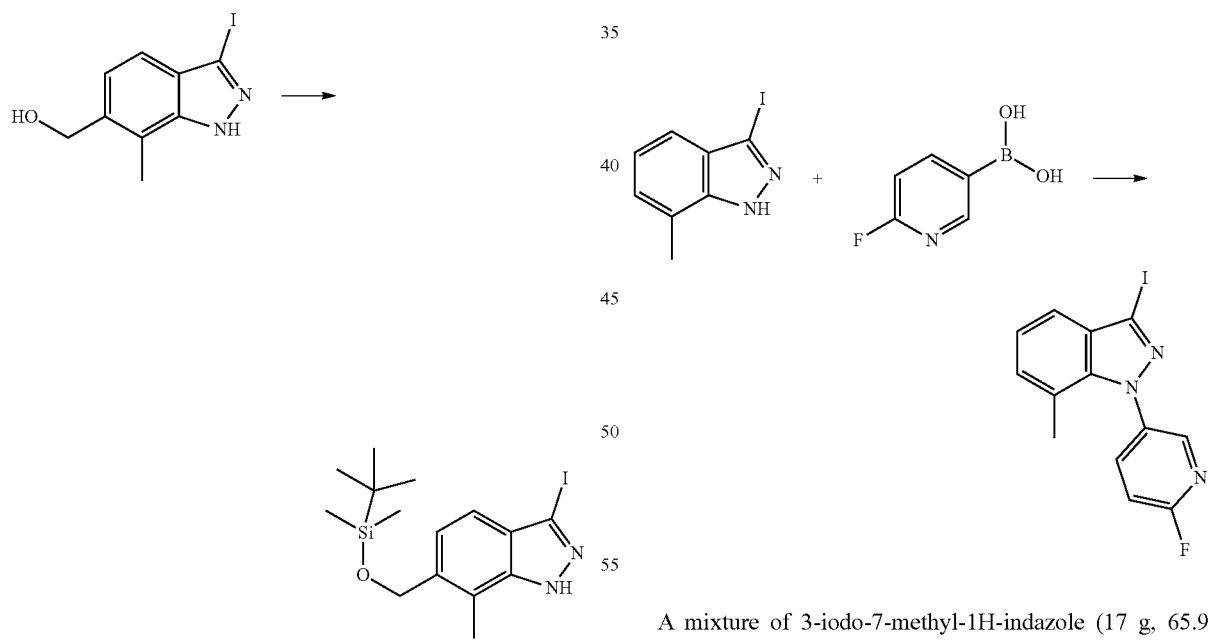

To a stirred solution of (3-Iodo-7-methyl-1H-indazol-6-yl)-methanol C1 (100 mg, 347 μmol) in DMF (2 ml) is added at 0° C. imidazole (35 mg, 521 μmol) and TBDMS chloride (63 mg, 417 μmol). The mixture is stirred for 16 h at RT and then partitioned between EtOAc and ice water. The organic layer is dried over MgSO$_4$, concentrated in vacuo and the product purified by NP chromatography. Yield: 70 mg (50%). HPLC-MS: M+H=403; tR=2.85 min (Method_5)

Preparation of Intermediates D

D1 1-(6-fluoropyridin-3-yl)-3-iodo-7-methyl-1H-indazole

A mixture of 3-iodo-7-methyl-1H-indazole (17 g, 65.9 mmol), (6-fluoropyridin-3-yl)boronic acid (15.8 g, 112 mmol), copper(II) acetate (17.9 g, 98.8 mmol) and pyridine (10.4 g, 132 mmol) in DCM (340 ml) is stirred at RT for 16 h with exposure to air. The solids are filtered off, the mixture is concentrated in vacuo and the product purified by RP chromatography. Yield: 14 g (60%). HPLC-MS: M+H=354; tR=1.50 min (Method_2).

The following intermediates are prepared analogously from corresponding 3-iodo-indazoles (intermediates C):

| # | Structure | IUPAC Name | tR [min] | [M + H] | A.M. |
|---|---|---|---|---|---|
| D2 | 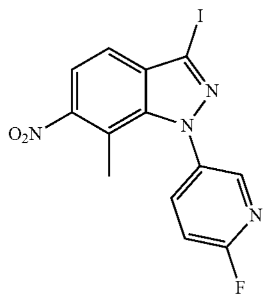 [SMILES: Cc1c([N+](=O)[O-])ccc2c(I)nn(-c3ccc(F)nc3)c12] | 1-(6-fluoropyridin-3-yl)-3-iodo-7-methyl-6-nitro-1H-indazole | 2.42 | 399 | Method_5 |
| D3 | 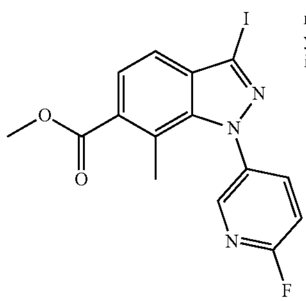 | methyl 1-(6-fluoropyridin-3-yl)-3-iodo-7-methyl-1H-indazole-6-carboxylate | 2.24 | 421 | Method_6 |
| D4 | 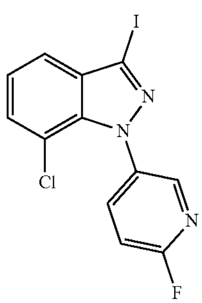 [SMILES: Fc1ccc(-n2nc(I)c3cccc(Cl)c32)cn1] | 7-chloro-1-(6-fluoropyridin-3-yl)-3-iodo-1H-indazole | 1.074 | 374 | Method_1 |
| D5 | 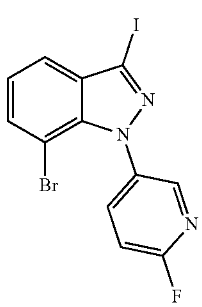 [SMILES: Fc1ccc(-n2nc(I)c3cccc(Br)c32)cn1] | 7-bromo-1-(6-fluoropyridin-3-yl)-3-iodo-1H-indazole | 1.06 | 418/420 | Method_1 |
| D6 | 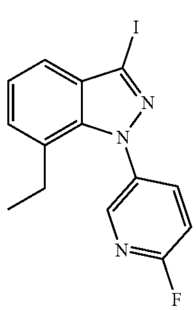 [SMILES: CCc1cccc2c(I)nn(-c3ccc(F)nc3)c12] | 7-ethyl-1-(6-fluoropyridin-3-yl)-3-iodo-1H-indazole | 1.06 | 368 | Method_1 |

-continued

| # | Structure | IUPAC Name | tR [min] | [M + H] | A.M. |
|---|---|---|---|---|---|
| D7 | 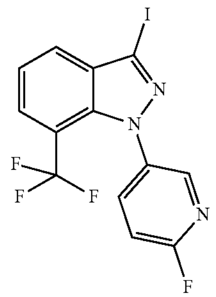 [SMILES: Fc1ccc(-n2nc(I)c3cccc(C(F)(F)F)c32)cn1] | 1-(6-fluoropyridin-3-yl)-3-iodo-7-(trifluoromethyl)-1H-indazole | 1.05 | 408 | Method_1 |
| D8 | 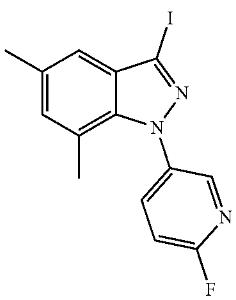 [SMILES: Cc1cc(C)c2c(c1)c(I)nn2-c1ccc(F)nc1] | 1-(6-fluoropyridin-3-yl)-3-iodo-5,7-dimethyl-1H-indazole | — | — | — |
| D9 | 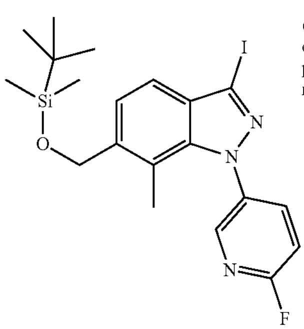 | 6-{[(tert-butyldimethylsilyl)oxy]methyl}-1-(6-fluoropyridin-3-yl)-3-iodo-7-methyl-1H-indazole | 3.06 | 498 | Method_5 |

D10 [1-(6-fluoropyridin-3-yl)-3-iodo-7-methyl-1H-indazol-6-yl]methanol

E1 1-(6-fluoropyridin-3-yl)-2',7-dimethyl-1H,2'H-3,4'-biindazole

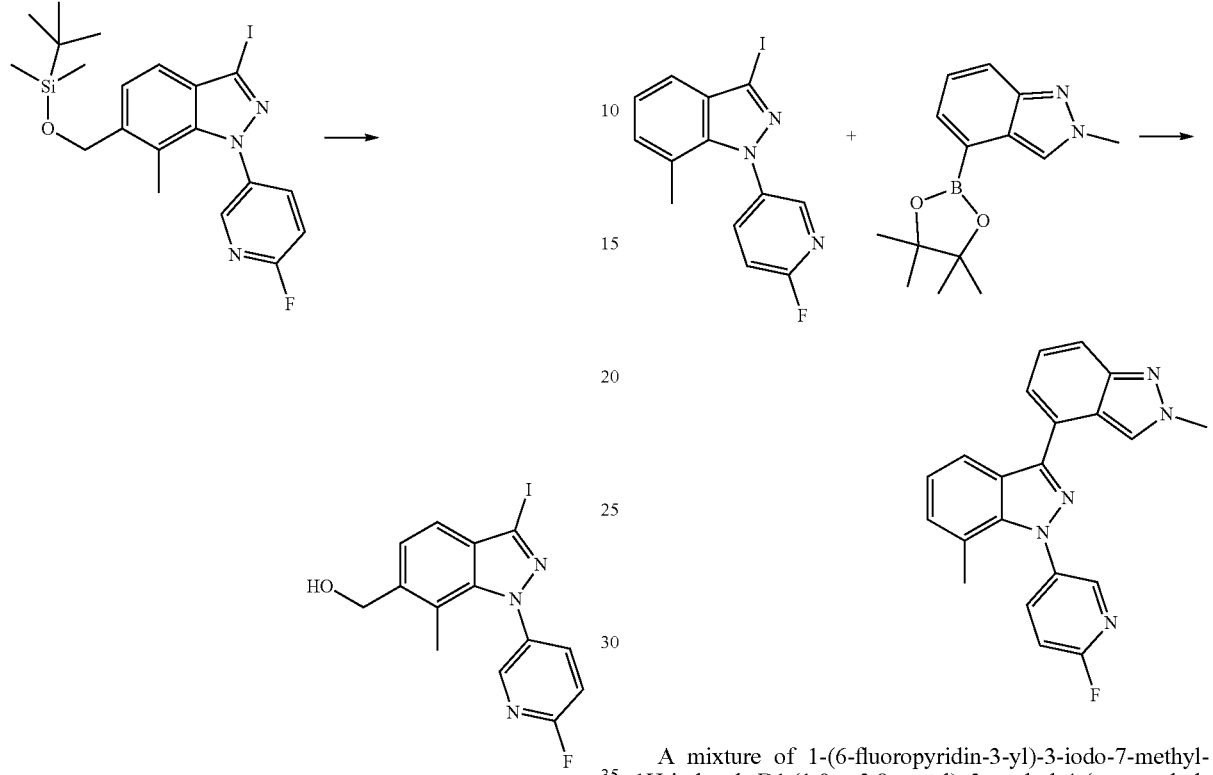

To 6-{[(tert-butyldimethylsilyl)oxy]methyl}-1-(6-fluoropyridin-3-yl)-3-iodo-7-methyl-1H-indazole D9 (50 mg, 101 µmol) in THF (2 ml) is added tetra-N-butyl ammonium fluoride (1 mol/l in THF, 202 µl, 202 µmol). The mixture is stirred for 16 h at RT. Saturated aqueous solution of ammonium chloride is added and the mixture is extracted with EtOAc. The organic layer is dried over MgSO$_4$, concentrated in vacuo and the product purified by RP chromatography. Yield: 26 mg (68%). HPLC-MS: M+H=384; tR=1.82 min (Method_6)

Preparation of Intermediates E

A mixture of 1-(6-fluoropyridin-3-yl)-3-iodo-7-methyl-1H-indazole D1 (1.0 g, 2.8 mmol), 2-methyl-4-(tetramethyl-1,3,2-dioxaborolan-2-yl)-2H-indazole (1.1 g, 4.2 mmol), 1,1'-Bis(diphenylphosphino)ferrocene]dichloropalladium (II) (0.21 g, 0.28 mmol), Na$_2$CO$_3$ (0.9 g, 8.5 mmol) in dioxane (20 ml) and water (5 ml) is stirred under argon atmosphere for 2 h at 110° C. At RT water (100 ml) is added and the mixture extracted with EtOAc. The combined organic layers are dried over MgSO$_4$, concentrated in vacuo and the product purified by RP HPLC. Yield: 0.8 g (79%). HPLC-MS: M+H=358; tR=0.997 min (Method_1).

The following intermediates are prepared analogously from intermediates D utilizing corresponding boronic acid derivatives:

| # | Structure | IUPAC Name | tR [min] | [M + H] | A.M. |
|---|---|---|---|---|---|
| E2 | 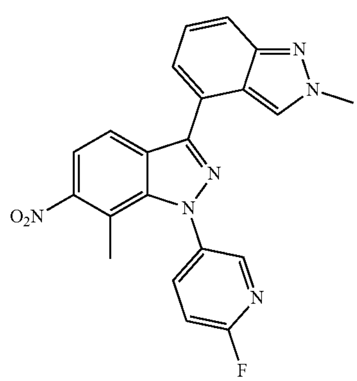 [SMILES: Cc1c([N+](=O)[O-])ccc2c(-c3cccc4nn(C)cc34)nn(-c3ccc(F)nc3)c12] | 1-(6-fluoropyridin-3-yl)-2',7-dimethyl-6-nitro-1H,2'H-3,4'-biindazole | 2.27 | 403 | Method_5 |

| # | Structure | IUPAC Name | tR [min] | [M + H] | A.M. |
|---|---|---|---|---|---|
| E3 | 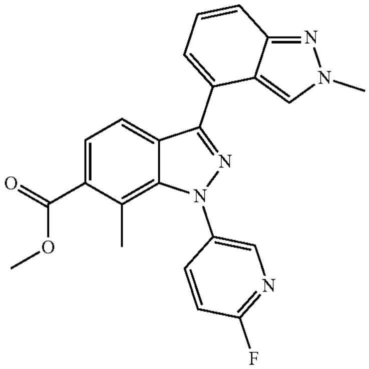 [SMILES: COC(=O)c1ccc2c(-c3cccc4nn(C)cc34)nn(-c3ccc(F)nc3)c2c1C] | methyl 1-(6-fluoropyridin-3-yl)-2',7-dimethyl-1H,2'H-[3,4'-biindazole]-6-carboxylate | 0.96 | 416 | Method_1 |
| E4 | 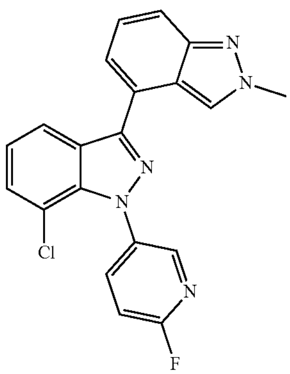 [SMILES: Cn1cc2c(-c3nn(-c4ccc(F)nc4)c4c(Cl)cccc34)cccc2n1] | 7-chloro-1-(6-fluoro-pyridin-3-yl)-2'-methyl-1H,2'H-3,4'-biindazole | 1.027 | 378 | Method_1 |
| E5 | 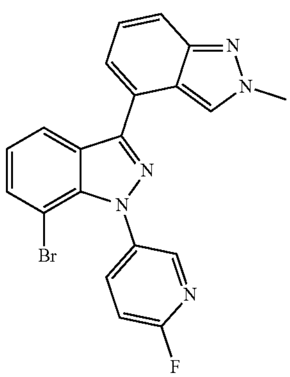 [SMILES: Cn1cc2c(-c3nn(-c4ccc(F)nc4)c4c(Br)cccc34)cccc2n1] | 7-bromo-1-(6-fluoro-pyridin-3-yl)-2'-methyl-1H,2'H-3,4'-biindazole | 1.04 | 422/424 | Method_1 |
| E6 | 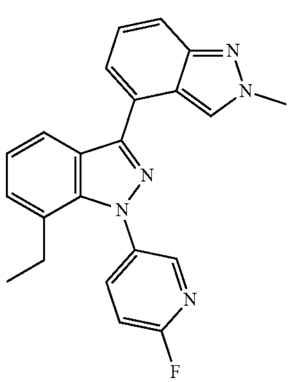 [SMILES: CCc1cccc2c(-c3cccc4nn(C)cc34)nn(-c3ccc(F)nc3)c12] | 7-ethyl-1-(6-fluoropyridin-3-yl)-2'-methyl-1H,2'H-3,4'-biindazole | 1,.48 | 372 | Method_2 |

-continued

| # | Structure | IUPAC Name | tR [min] | [M + H] | A.M. |
|---|---|---|---|---|---|
| E7 | 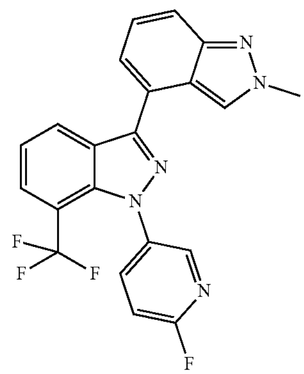 [SMILES: Cn1cc2c(-c3nn(-c4ccc(F)nc4)c4c(C(F)(F)F)cccc34)cccc2n1] | 1-(6-fluoropyridin-3-yl)-2'-methyl-7-(trifluoromethyl)-1H,2'H-3,4'-biindazole | 1.46 | 412 | Method_2 |
| E8 | 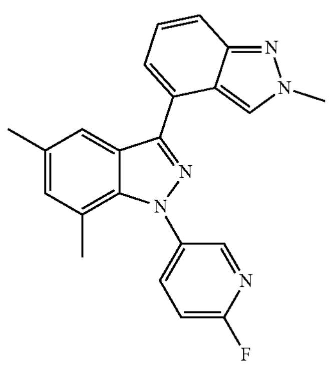 | 1-(6-fluoropyridin-3-yl)-2',5,7-trimethyl-1H,2'H-3,4'-biindazole | 1.02 | 372 | Method_1 |
| E9 | 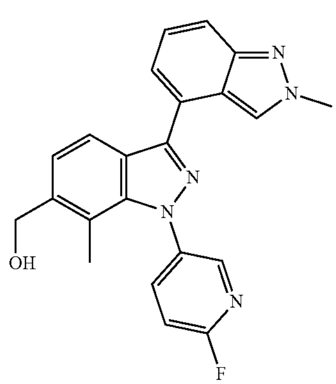 [SMILES: Cc1c(CO)ccc2c(-c3cccc4nn(C)cc34)nn(-c3ccc(F)nc3)c12] | [1-(6-fluoropyridin-3-yl)-2',7-dimethyl-1H,2'H-[3,4'-biindazol]-6-yl]methanol | 0.83 | 388 | Method_1 |

Additional intermediates E are synthesized as follows:

E10 1-(6-fluoropyridin-3-yl)-2',7-dimethyl-1H,2'H-[3,4'-biindazol]-6-amine

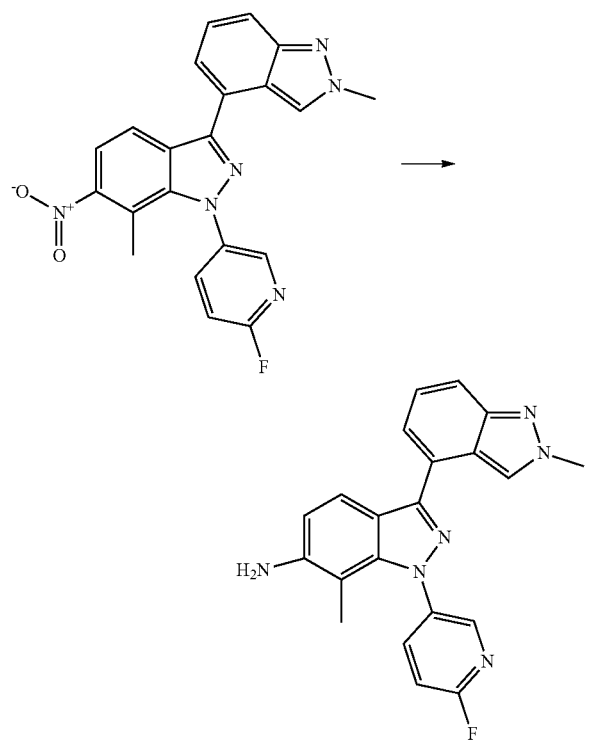

To 1-(6-fluoro-pyridin-3-yl)-7,2'-dimethyl-6-nitro-1H,2'H-[3,4']biindazolyl E2 (0.5 g, 1.2 mmol) in methanol (5 ml) and THF (5 ml) is added palladium on carbon (41 mg, 0.39 mmol). The mixture is hydrogenated for 16 h at RT (hydrogen pressure 50 psi). The reaction is filtered through celite and washed with methanol (50 ml). The filtrate is concentrated in vacuo and the crude product used without further purification. Yield: 0.35 g (76%). HPLC-MS: M+H=373; tR=1.96 min (Method_5)

E11 1-(6-fluoropyridin-3-yl)-6-iodo-2',7-dimethyl-1H,2'H-3,4'-biindazole

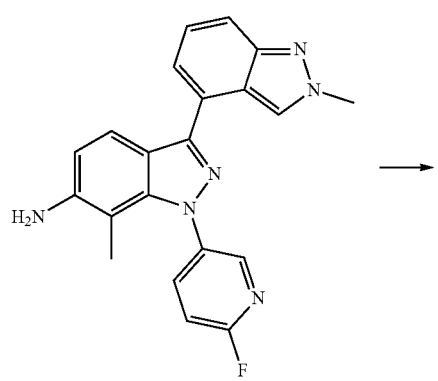

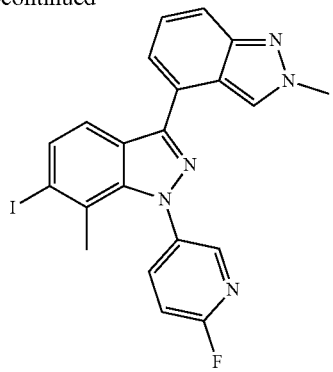

To 1-(6-fluoropyridin-3-yl)-2',7-dimethyl-1H,2'H-[3,4'-biindazol]-6-amine E10 (0.1 g, 270 µmol) in water (1 ml) is added at 0° C. aqueous conc. HCl (1 ml) followed by sodium nitrite (20 mg; 295 µmol) in water (1 ml). The reaction mixture is stirred at RT for 1 h. Sodium tetra fluoroborate (43 mg, 394 µmol) is added and stirring continued for 10 min. The mixture is filtered, the solids washed with 10% NaBF4 solution and diethyl ether and dried under vacuum. Together with 1 ml of DMSO this is added to a mixture consisting of iodine (68 mg, 270 µmol) and potassium iodide (70 mg, 414 µmol) in DMSO (2 ml). The mixture stirred at RT for 1 h then at 45° C. for 30 min before the addition of FeSO$_4$*7H$_2$O (90 mg, 324 µmol) and stirring for additional 30 min. The mixture is poured into an aqueous solution of sodium thiosulfate and extracted with EtOAc. The combined organic layers are washed with aqueous sodium thiosulfate solution and water, dried over Na$_2$SO$_4$ and concentrated in vacuo. Yield of crude product: 50 mg (39%). HPLC-MS: M+H=484; tR=2.59 min (Method_5)

E12 1-(6-fluoropyridin-3-yl)-2',7-dimethyl-6-(1-methyl-1H-pyrazol-4-yl)-1H,2'H3,4'-biindazole

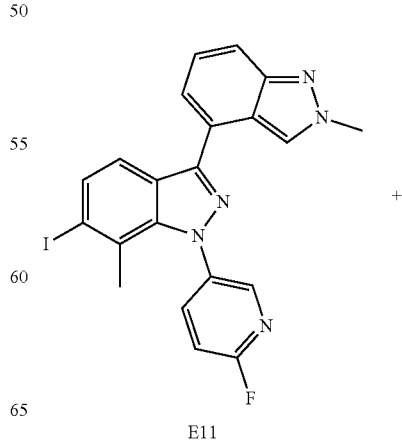

E11

-continued

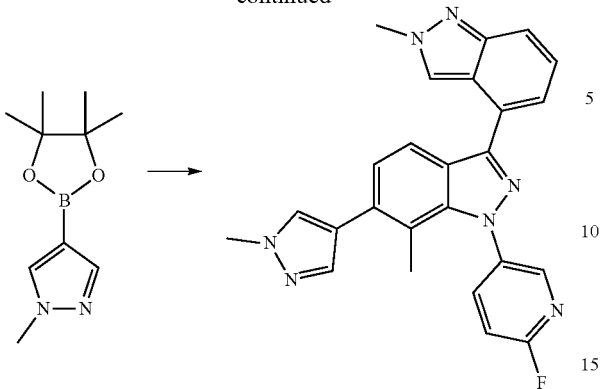

E12

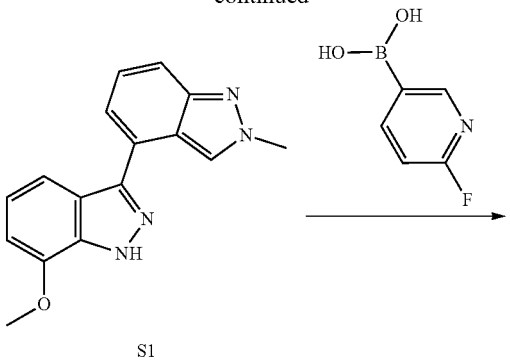

A mixture of 1-(6-fluoropyridin-3-yl)-6-iodo-2',7-dimethyl-1H,2'H-3,4'-biindazole E11 (100 mg, 200 μmol), 1-methyl-4-(4,4,5,5-tetramethyl-1,3,2-dioxaborolan-2-yl)-1H-pyrazole (52 mg, 240 μmol), ({[1,1'-biphenyl]-2-yl}amino)palladiumylium dicyclohexyl({2',6'-dimethoxy-[1,1'-biphenyl]-2-yl})phosphane methanesulfonate (8 mg, 10 μmol), K$_3$PO$_4$ (87 mg, 400 μmol), dioxane (1 ml) and water (0.5 ml) is stirred under argon atmosphere for 16 h at 80° C. At RT water (30 ml) is added and the mixture extracted with DCM. The combined organic layers are dried over Na$_2$SO$_4$, concentrated in vacuo to give 50 mg (56%) crude E12 which is used in the next step without further purification.

By following an alternative sequence of the synthetic steps shown in Scheme 1 additional intermediates E can be obtained via intermediates S:

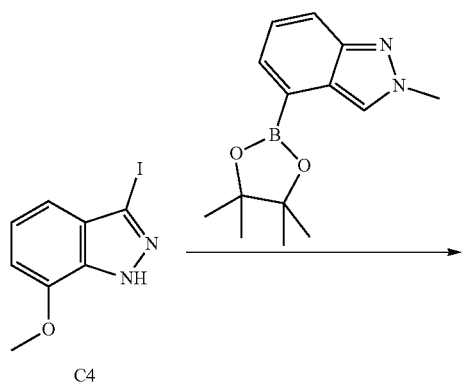

C4

E13

S1 7-methoxy-2'-methyl-1H,2'H-3,4'-biindazole

A mixture of 3-iodo-7-methoxy-1H-indazole C4 (500 mg, 1.62 mmol), 2-methyl-4-(4,4,5,5-tetramethyl-1,3,2-dioxaborolan-2-yl)-2H-indazole (512 mg, 1.94 mmol), ({[1,1'-biphenyl]-2-yl}amino)palladiumylium dicyclohexyl({2',6'-dimethoxy-[1,1'-biphenyl]-2-yl})phosphane methanesulfonate (126 mg, 162 μmol), K$_3$PO$_4$ (695 mg, 3.24 mmol), dioxane (5 ml) and water (1 ml) is stirred under argon atmosphere for 16 h at 80° C. At RT the mixture is diluted with DCM and extracted with water. The organic layer is dried over Na$_2$SO$_4$, concentrated in vacuo and the intermediate 7-methoxy-2'-methyl-1H,2'H-3,4'-biindazole purified by NP chromatography. Yield: 256 mg (57%). HPLC-MS: M+H=279; tR=0.55 min (Method_7)

The following intermediate S2 is synthesized analogously to S1:

| # | Structure | IUPAC Name | tR [min] | [M + H] | A.M. |
|---|---|---|---|---|---|
| S2 | 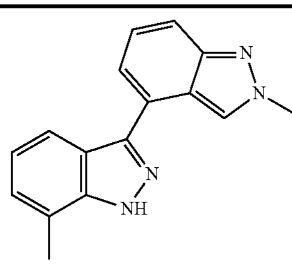 | 2',7-dimethyl-1H,2'H-3,4'-biindazole | 1.16 | 263 | Method_1 |

E13 1-(6-fluoropyridin-3-yl)-7-methoxy-2'-methyl-1H,2'H-3,4'-biindazole

To 7-methoxy-2'-methyl-1H,2'H-3,4'-biindazole S1 (256 mg, 920 µmol) is added (6-fluoropyridin-3-yl)boronic acid (259 mg, 1.84 mmol), copper(II) acetate (167 mg, is 920 µmol) and pyridine (218 µl, 2.8 mmol) in DCM (5 ml) and DMF (2.25 ml). The mixture is stirred at RT for 60 h with exposure to air. The solids are filtered off, the filtrate is concentrated in vacuo and the product purified by NP chromatography. Yield: 185 mg (54%). HPLC-MS: M+H=374; tR=0.70 min (Method_7).

In addition, intermediates D can be boronylated to intermediates T for Suzuki coupling with e.g. heteroaryl bromides to yield further intermediates E:

T1 3-(5,5-dimethyl-1,3,2-dioxaborinan-2-yl)-1-(6-fluoropyridin-3-yl)-7-methyl-1H-indazole

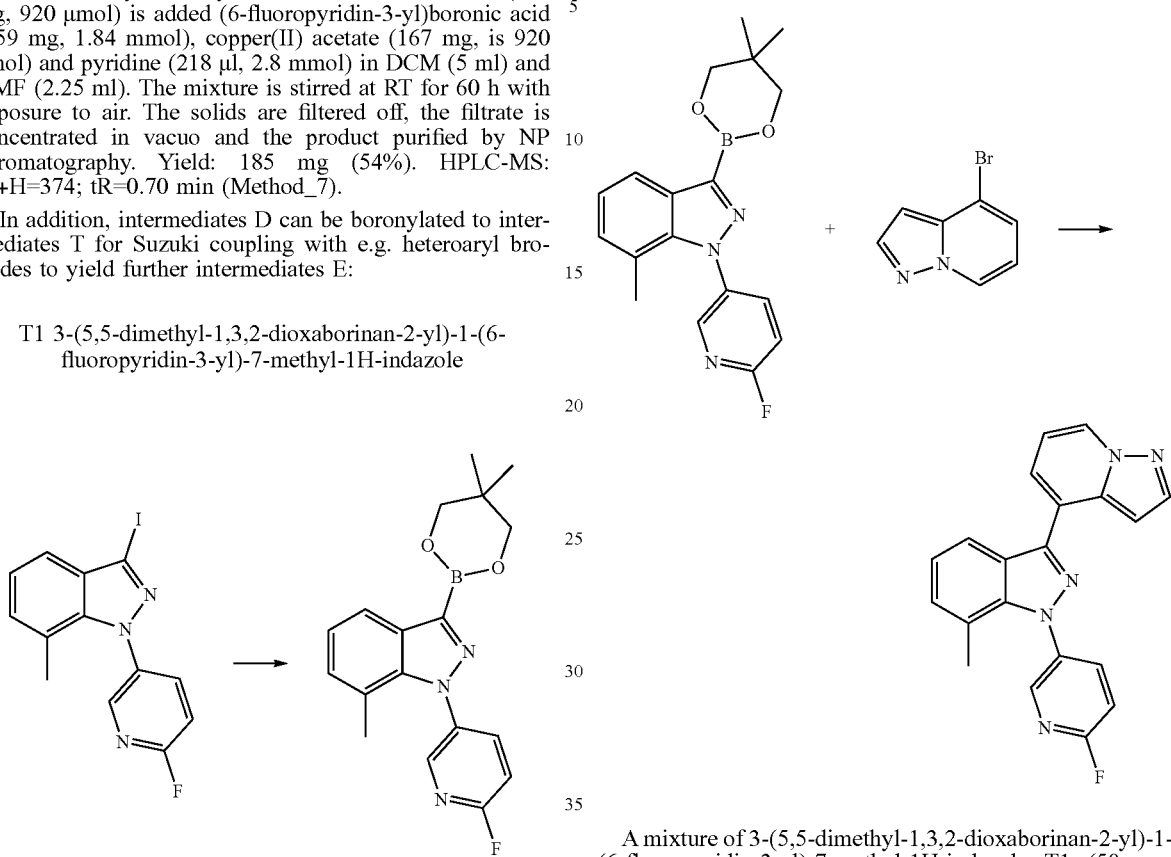

To 1-(6-fluoro-pyridin-3-yl)-3-iodo-7-methyl-1H-indazole D1 (17 g, 48.1 mmol) in dioxane (170 ml) is added bisneopentyl glycolato diborane (16.3 g, 72.2 mmol), potassium acetate (14.2 g, 144 mmol), dichlorobis(triphenylphosphine)palladium(II) (3.38 g, 4.8 mmol) under argon atmosphere and the mixture is stirred at 100° C. for 16 h. At RT EtOAc and water is added and the aqueous layer is extracted with EtOAc. The combined organic layer is concentrated in vacuo and rinsed with petrol ether. The crude product is used in the next step without further purification. Yield of crude product: 4 g (25%).

E14 1-(6-fluoropyridin-3-yl)-7-methyl-3-{pyrazolo[1,5-a]pyridin-4-yl}-1H-indazole A mixture of 3-(5,5-dimethyl-1,3,2-dioxaborinan-2-yl)-1-(6-fluoropyridin-3-yl)-7-methyl-1H-indazole T1 (50 mg, 147 µmol), 4-bromopyrazolo[1,5-a]pyridine (44 mg, 223 µmol), 1,1'-Bis(diphenylphosphino)ferrocene]dichloropalladium(II) (11 mg, 15 µmol), Na2CO3 (47 mg, 443 µmol) in dioxane (1 ml) and water (250 µl) is stirred under argon atmosphere for 1 h at 110° C. At RT water (20 ml) is added and the mixture extracted with DCM. The combined organic layers are dried over MgSO4, concentrated in vacuo and the product purified by RP HPLC. Yield: 35 mg (69%). HPLC-MS: M+H=344; tR=0.993 min (Method_1).

The following intermediates are prepared analogously from intermediate T by coupling with corresponding heteroaryl bromides. E15 and E18 are prepared utilizing U2 and U3, respectively.

| # | Structure | IUPAC Name | tR [min] | [M + H] | A.M. |
|---|---|---|---|---|---|
| E15 | 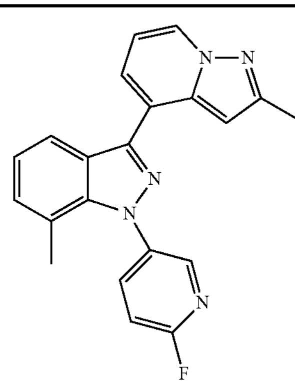 | 1-(6-fluoropyridin-3-yl)-7-methyl-3-(2-methylpyrazolo[1,5-a]pyridin-4-yl)-1H-indazole | 1.062 | 358 | Method_1 |

| # | Structure | IUPAC Name | tR [min] | [M + H] | A.M. |
|---|---|---|---|---|---|
| E16 | 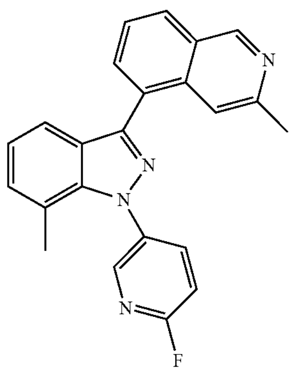 [SMILES: Cc1cc2c(-c3nn(-c4ccc(F)nc4)c4c(C)cccc34)cccc2cn1] | 5-(1-(6-fluoropyridin-3-yl)-7-methyl-1H-indazol-3-yl)-3-methylisoquinoline | 1.001 | 369 | Method_1 |
| E17 | 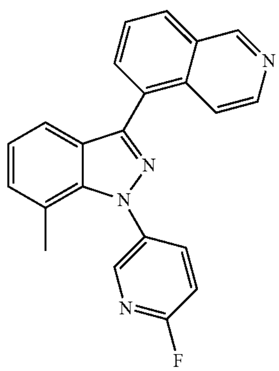 [SMILES: Cc1cccc2c(-c3cccc4cnccc34)nn(-c3ccc(F)nc3)c12] | 5-[1-(6-fluoropyridin-3-yl)-7-methyl-1H-indazol-3-yl]isoquinoline | N.A. | N.A. | N.A: |
| E18 | 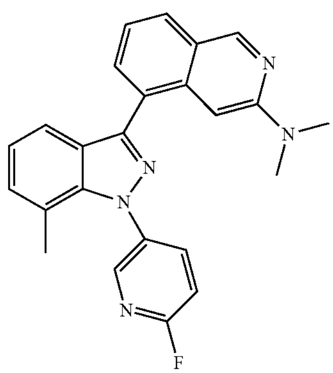 [SMILES: Cc1cccc2c(-c3cccc4cnc(N(C)C)cc34)nn(-c3ccc(F)nc3)c12] | 5-(1-(6-fluoropyridin-3-yl)-7-methyl-1H-indazol-3-yl)-N,N-dimethylisoquinolin-3-amine | 1.138 | 398 | Method_1 |
| E19 | 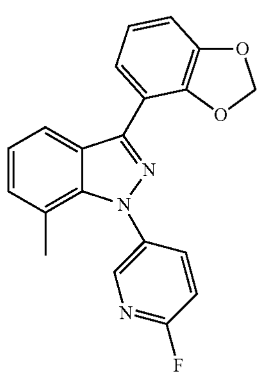 [SMILES: Cc1cccc2c(-c3cccc4c3OCO4)nn(-c3ccc(F)nc3)c12] | 3-(benzo[d][1,3]dioxol-4-yl)-1-(6-fluoropyridin-3-yl)-7-methyl-1H-indazole | 0.772 | 348 | Method_8 |

U1 3-bromo-2-(prop-1-yn-1-yl)pyridine

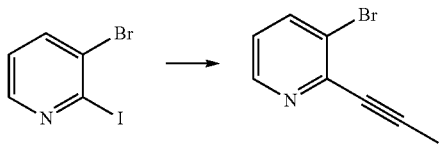

DMF (100 ml) at RT under argon atmosphere is purged with propyne gas for 10 min. 3-Bromo-2-iodopyridine (10 g, 35.2 mmol), dichlorobis(triphenylphosphine)palladium(II) (2.47 g, 3.52 mmol) and copper(I) iodide (669 mg, 3.52 mmol) is added and the mixture stirred for 4 h. The mixture is diluted with water and extracted with EtOAc. The combined organic layers are dried over $Na_2SO_4$ and concentrated in vacuo. The product is purified by NP chromatography. Yield: 4.0 g (58%). HPLC-MS: M+H=196; tR=1.94 min (Method_5).

U2 4-bromo-2-methylpyrazolo[1,5-a]pyridine

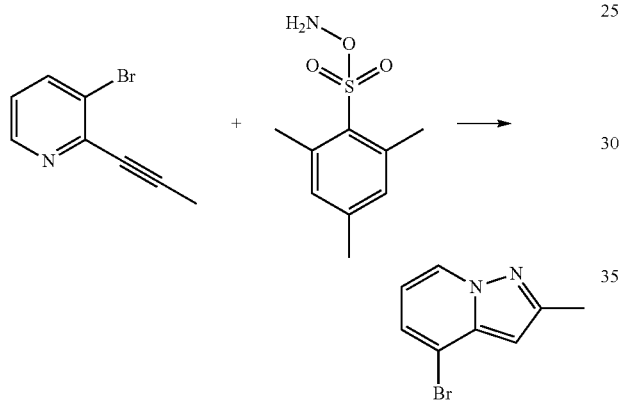

To a stirred mixture of 3-bromo-2-prop-1-ynyl-pyridine U1 (6.0 g; 30.6 mmol) in DCM (55 ml) is added O-(mesitylsulfonyl)hydroxylamine (9.88 g, 45.9 mmol) in DCM (5 ml) at 0° C. The mixture is stirred for 4 h at rt before the solvent is removed under reduced pressure. To the crude material is added DMF (60 ml) and $K_2CO_3$ (12.7 g, 91.8 mmol) at rt and the mixture stirred for 16 h. Water is added and the mixture extracted with diethylether. The combined organic layers are dried over $MgSO_4$ and concentrated in vacuo. The product is purified by RP chromatography. Yield: 900 mg (14%). HPLC-MS: M+H=211; tR=2.10 min (Method_5).

U3) 5-bromo-N,N-dimethylisoquinolin-3-amine

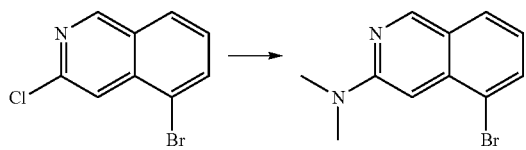

A mixture of 5-bromo-3-chloroisoquinoline (100 mg, 412 µmol), dimethylamine hydrochloride (2.45 g, 30 mmol), NMP (3 ml) and DIPEA (5.1 ml, 30 mmol) is heated to 200° C. for 15 h. The mixture is diluted with water and extracted with EtOAc. The combined organic layers are dried over $MgSO_4$ and concentrated in vacuo. The product is purified by RP chromatography. Yield: 69 mg (67%). HPLC-MS: M+H=251/253; tR=1.045 min (Method_1).

EXAMPLES

Preparation of Examples #1-#45 and Intermediates F

1) Methyl 3-(5-(2',7-dimethyl-1H,2'H-[3,4'-biindazol]-1-yl)pyridin-2-yl)-3-azabicyclo[3.1.0]hexane-6-carboxylate

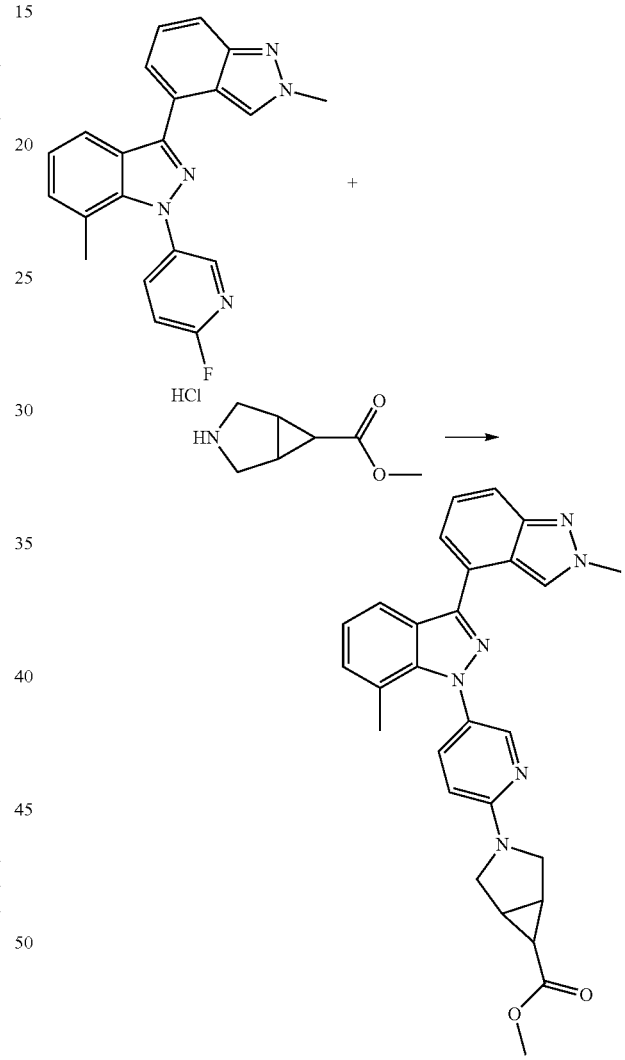

A mixture of 1-(6-fluoropyridin-3-yl)-2',7-dimethyl-1H,2'H-3,4'-biindazole E1 (20 mg, 56 µmol), methyl 3-azabicyclo[3.1.0]hexane-6-carboxylate hydrochloride (10 mg, 56 µmol) and DIPEA (50 µl, 0.29 mmol) in DMSO (0.1 ml) is stirred for 16 h at 80° C. The mixture is diluted with water and extracted with EtOAc. The combined organic layers are dried over $MgSO_4$ and concentrated in vacuo. The product is purified by RP chromatography. Yield: 13 mg (48%). HPLC-MS: M+H=479; tR=1.47 min (Method_2).

The following examples are prepared analogously from intermediates E utilizing corresponding amines. In case of salts of amines (e.g. hydrochlorides) respective equivalents of additional base are used.

| # | Structure | IUPAC Name | tR [min] | [M + H] | A.M. |
|---|---|---|---|---|---|
| #2 | 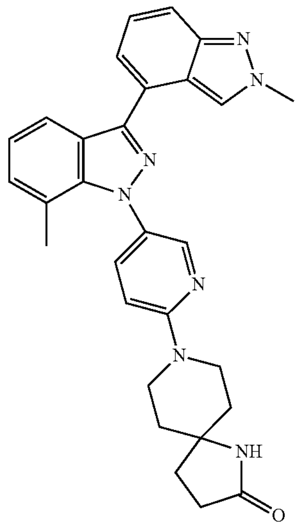 [SMILES: Cc1cccc2c(-c3cccc4nn(C)cc34)nn(-c3ccc(N4CCC5(CCC(=O)N5)CC4)nc3)c12] | 8-(5-{2',7-dimethyl-1H,2'H-[3,4'-biindazol]-1-yl}pyridin-2-yl)-1,8-diazaspiro[4.5]decan-2-one | 1.32 | 492 | Method_2 |
| #3 | 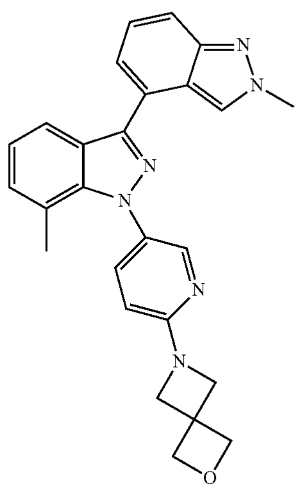 [SMILES: Cc1cccc2c(-c3cccc4nn(C)cc34)nn(-c3ccc(N4CC5(COC5)C4)nc3)c12] | 2',7-dimethyl-1-(6-{2-oxa-6-azaspiro[3.3]heptan-6-yl}pyridin-3-yl)-1H,2'H-3,4'-biindazole | 1.31 | 437 | Method_2 |
| #4 | 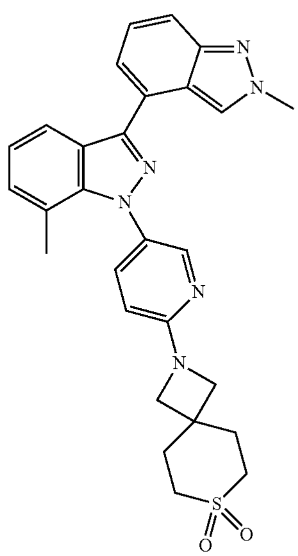 [SMILES: Cc1cccc2c(-c3cccc4nn(C)cc34)nn(-c3ccc(N4CC5(CCS(=O)(=O)CC5)C4)nc3)c12] | 2-(5-{2',7-dimethyl-1H,2'H-[3,4'-biindazol]-1-yl}pyridin-2-yl)-7λ⁶-thia-2-azaspiro[3.5]nonane-7,7-dione | 1.30 | 513 | Method_2 |

| # | Structure | IUPAC Name | tR [min] | [M + H] | A.M. |
|---|---|---|---|---|---|
| #5 | 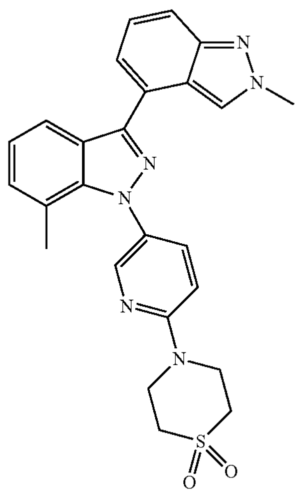 [SMILES: Cc1cccc2c(-c3cccc4nn(C)cc34)nn(-c3ccc(N4CCS(=O)(=O)CC4)nc3)c12] | 4-(5-{2,7-dimethyl-1H,2'H-[3,4'-biindazol]-1-yl}pyridin-2-yl)-1λ⁶-thiomorpholine-1,1-dione | 1.37 | 473 | Method_2 |
| #6 | 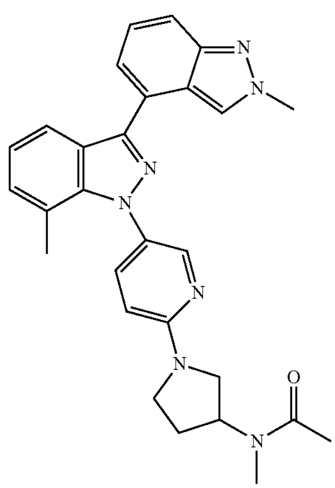 [SMILES: CC(=O)N(C)C1CCN(c2ccc(-n3nc(-c4cccc5nn(C)cc45)c4cccc(C)c43)cn2)C1] | N-[1-(5-{2',7-dimethyl-1H,2'H-[3,4'-biindazol]-1-yl}pyridin-2-yl)pyrrolidin-3-yl]-N-methylacetamide | 1.32 | 480 | Method_2 |
| #7 | 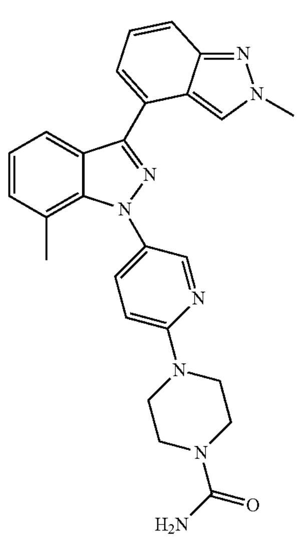 [SMILES: Cc1cccc2c(-c3cccc4nn(C)cc34)nn(-c3ccc(N4CCN(C(N)=O)CC4)nc3)c12] | 4-(5-{2',7-dimethyl-1H,2'H-[3,4'-biindazol]-1-yl}pyridin-2-yl)piperazine-1-carboxamide | 1.23 | 467 | Method_2 |

| # | Structure | IUPAC Name | tR [min] | [M + H] | A.M. |
|---|---|---|---|---|---|
| #8 | 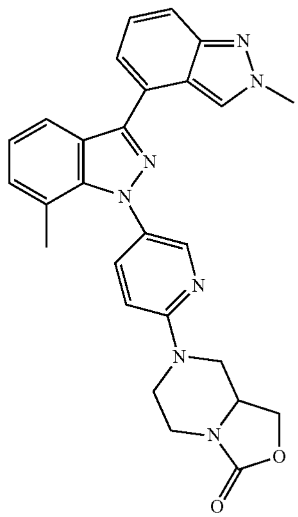 [SMILES: Cc1cccc2c(-c3cccc4nn(C)cc34)nn(-c3ccc(N4CCN5C(=O)OCC5C4)nc3)c12] | 7-(5-{2',7-dimethyl-1H,2'H-[3,4'-biindazol]-1-yl}pyridin-2-yl)-hexahydro-1H-[1,3]oxazolo[3,4-a]pyrazin-3-one | 1.32 | 480 | Method_2 |
| #9 | 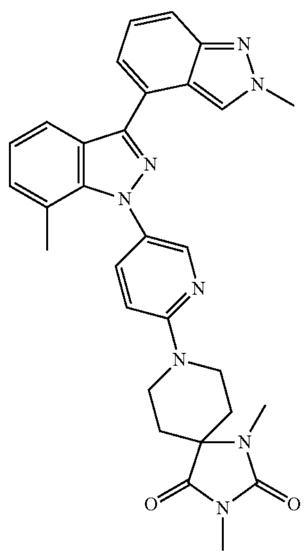 [SMILES: Cc1cccc2c(-c3cccc4nn(C)cc34)nn(-c3ccc(N4CCC5(CC4)C(=O)N(C)C(=O)N5C)nc3)c12] | 8-(5-{2',7-dimethyl-1H,2'H-[3,4'-biindazol]-1-yl}pyridin-2-yl)-1,3-dimethyl-1,3,8-triazaspiro[4.5]decane-2,4-dione | 1.41 | 535 | Method_2 |
| #10 | 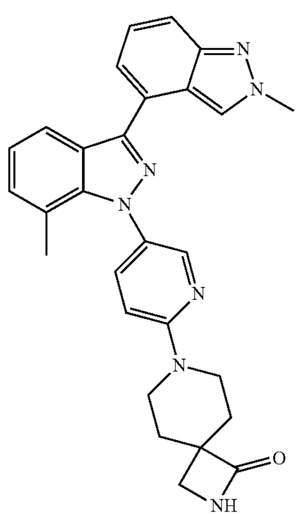 [SMILES: Cc1cccc2c(-c3cccc4nn(C)cc34)nn(-c3ccc(N4CCC5(CC4)CNC5=O)nc3)c12] | 7-(5-{2',7-dimethyl-1H,2'H-[3,4'-biindazol]-1-yl}pyridin-2-yl)-2,7-diazaspiro[3.5]nonan-1-one | 1.29 | 478 | Method_2 |

-continued

| # | Structure | IUPAC Name | tR [min] | [M + H] | A.M. |
|---|---|---|---|---|---|
| #11 | 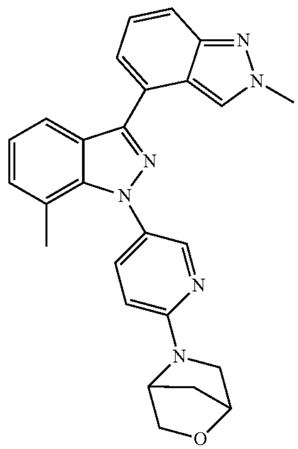 [SMILES: Cc1cccc2c(-c3cccc4nn(C)cc34)nn(-c3ccc(N4CC5CC4CO5)nc3)c12] | 2',7-dimethyl-1-(6-{2-oxa-5-azabicyclo[2.2.1]heptan-5-yl}pyridin-3-yl)-1H,2'H-3,4'-biindazole | 1.37 | 437 | Method_2 |
| #12 | 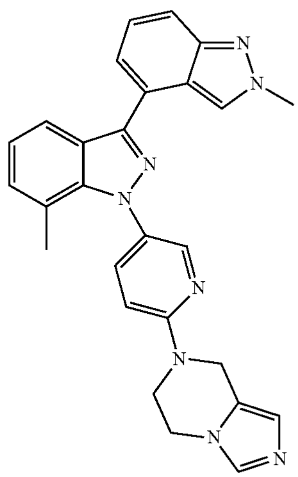 [SMILES: Cc1cccc2c(-c3cccc4nn(C)cc34)nn(-c3ccc(N4CCn5cncc5C4)nc3)c12] | 1-(6-{5H,6H,7H,8H-imidazo[1,5-a]pyrazin-7-yl}pyridin-3-yl)-2',7-dimethyl-1H,2'H-3,4'-biindazole | 1.33 | 461 | Method_2 |
| #13 | 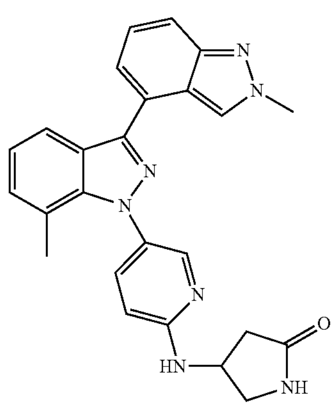 [SMILES: Cc1cccc2c(-c3cccc4nn(C)cc34)nn(-c3ccc(NC4CNC(=O)C4)nc3)c12] | 4-[(5-{2',7-dimethyl-1H,2'H-[3,4'-biindazol]-1-yl}pyridin-2-yl)amino]pyrrolidin-2-one | 1.19 | 438 | Method_2 |

| # | Structure | IUPAC Name | tR [min] | [M + H] | A.M. |
|---|---|---|---|---|---|
| #14 | 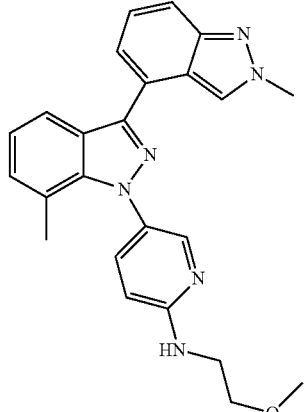 | 5-{2',7-dimethyl-1H,2'H-[3,4'-biindazol]-1-yl}-N-(2-methoxyethyl)pyridin-2-amine | 1.35 | 413 | Method_2 |
| #15 | 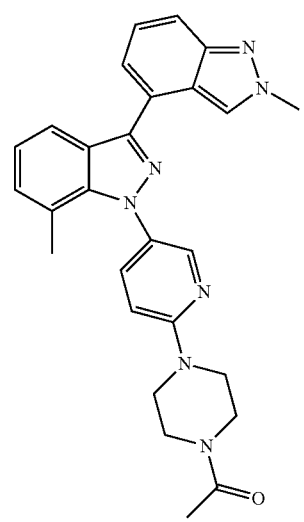 [SMILES: CC(=O)N1CCN(c2ccc(-n3nc(-c4cccc5nn(C)cc45)c4cccc(C)c43)cn2)CC1] | 1-[4-(5-{2',7-dimethyl-1H,2'H-[3,4'-biindazol]-1-yl}pyridin-2-yl)piperazin-1-yl]ethan-1-one | 1.31 | 466 | Method_2 |
| #16 | 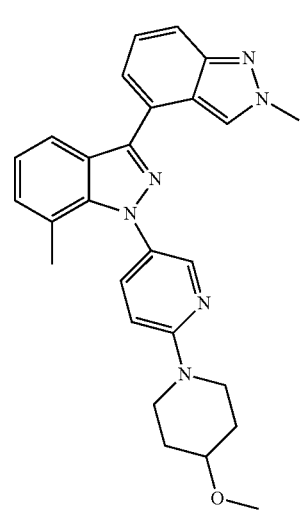 [SMILES: COC1CCN(c2ccc(-n3nc(-c4cccc5nn(C)cc45)c4cccc(C)c43)cn2)CC1] | 1-[6-(4-methoxypiperidin-1-yl)pyridin-3-yl]-2',7-dimethyl-1H,2'H-3,4'-biindazole | 1.52 | 453 | Method_2 |

-continued

| # | Structure | IUPAC Name | tR [min] | [M + H] | A.M. |
|---|---|---|---|---|---|
| #17 | 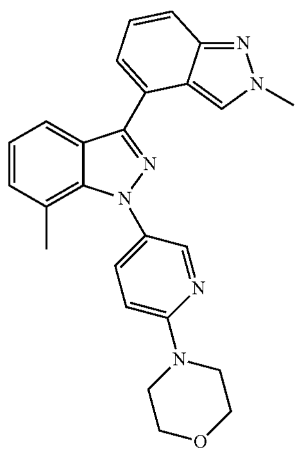 [SMILES: Cc1cccc2c(-c3cccc4nn(C)cc34)nn(-c3ccc(N4CCOCC4)nc3)c12] | 2',7-dimethyl-1-[6-(morpholin-4-yl)pyridin-3-yl]-1H,2'H-3,4'-biindazole | 1.42 | 425 | Method_2 |
| #18 | 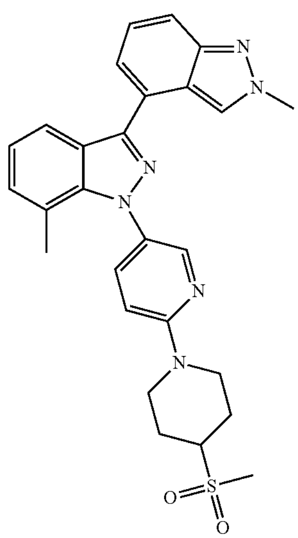 [SMILES: Cc1cccc2c(-c3cccc4nn(C)cc34)nn(-c3ccc(N4CCC(S(C)(=O)=O)CC4)nc3)c12] | 1-[6-(4-methanesulfonylpiperidin-1-yl)pyridin-3-yl]-2',7-dimethyl-1H,2'H-3,4'-biindazole | 1.34 | 501 | Method_2 |
| #19 | 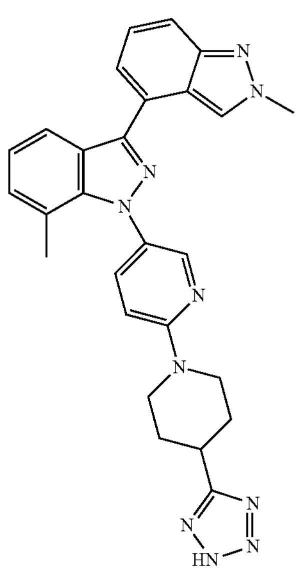 [SMILES: Cc1cccc2c(-c3cccc4nn(C)cc34)nn(-c3ccc(N4CCC(c5nn[nH]n5)CC4)nc3)c12] | 2',7-dimethyl-1-{6-[4-(2H-1,2,3,4-tetrazol-5-yl)piperidin-1-yl]pyridin-3-yl}-1H,2'H-3,4'-biindazole | 1.11 | 491 | Method_2 |

-continued

| # | Structure | IUPAC Name | tR [min] | [M + H] | A.M. |
|---|---|---|---|---|---|
| #20 | 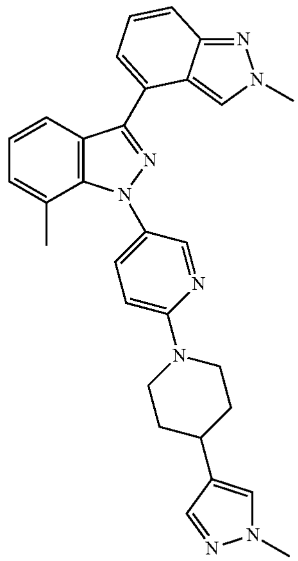 [SMILES: Cc1cccc2c(-c3cccc4nn(C)cc34)nn(-c3ccc(N4CCC(c5cnn(C)c5)CC4)nc3)c12] | 2',7-dimethyl-1-{6-[4-(1-methyl-1H-pyrazol-4-yl)piperidin-1-yl]pyridin-3-yl}-1H,2'H-3,4'-biindazole | 1.49 | 503 | Method_2 |
| #21 | 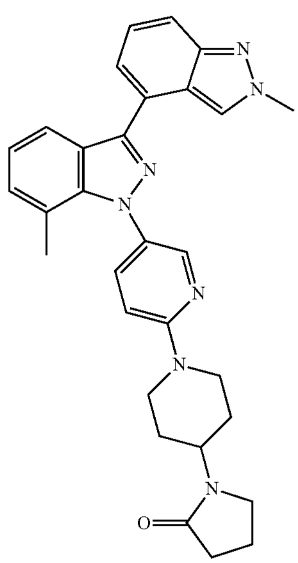 [SMILES: Cc1cccc2c(-c3cccc4nn(C)cc34)nn(-c3ccc(N4CCC(N5CCCC5=O)CC4)nc3)c12] | 1-[1-(5-{2',7-dimethyl-1H,2'H-[3,4'-biindazol]-1-yl}pyridin-2-yl)piperidin-4-yl]pyrrolidin-2-one | 1.31 | 506 | Method_2 |

-continued

| # | Structure | IUPAC Name | tR [min] | [M + H] | A.M. |
|---|---|---|---|---|---|
| #22 | 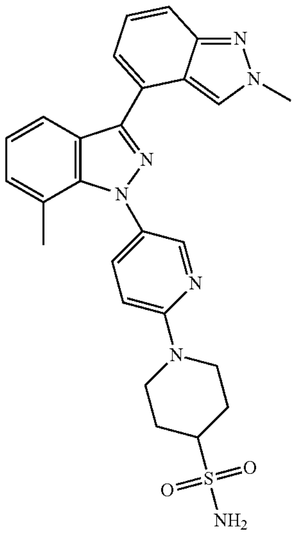 [SMILES: Cc1cccc2c(-c3cccc4nn(C)cc34)nn(-c3ccc(N4CCC(S(N)(=O)=O)CC4)nc3)c12] | 1-(5-{2',7-dimethyl-1H,2'H-[3,4'-biindazol]-1-yl}pyridin-2-yl)piperidine-4-sulfonamide | 1.30 | 502 | Method_2 |
| #23 | 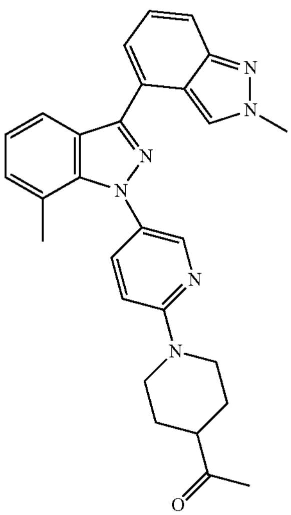 [SMILES: CC(=O)C1CCN(c2ccc(-n3nc(-c4cccc5nn(C)cc45)c4cccc(C)c43)cn2)CC1] | 1-[1-(5-{2',7-dimethyl-1H,2'H-[3,4'-biindazol]-1-yl}pyridin-2-yl)piperidin-4-yl]ethan-1-one | 1.52 | 465 | Method_2 |
| #24 | 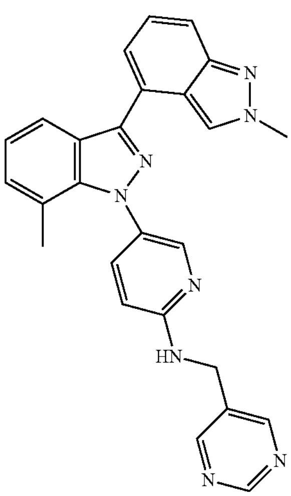 [SMILES: Cc1cccc2c(-c3cccc4nn(C)cc34)nn(-c3ccc(NCc4cncnc4)nc3)c12] | 5-{2',7-dimethyl-1H,2'H-[3,4'-biindazol]-1-yl}-N-[(pyrimidin-5-yl)methyl]pyridin-2-amine | 1.26 | 447 | Method_2 |

-continued

| # | Structure | IUPAC Name | tR [min] | [M + H] | A.M. |
|---|---|---|---|---|---|
| #25 | 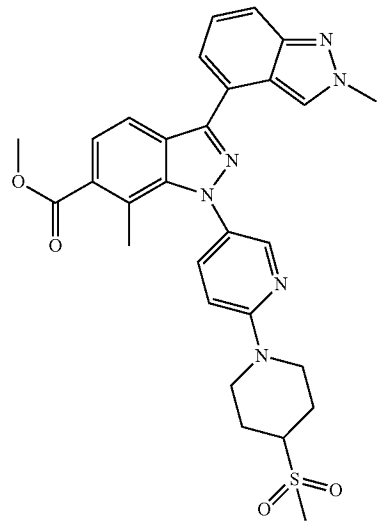 [SMILES: COC(=O)c1ccc2c(-c3cccc4nn(C)cc34)nn(-c3ccc(N4CCC(S(C)(=O)=O)CC4)nc3)c2c1C] | methyl 1-[6-(4-methanesulfonylpiperidin-1-yl)pyridin-3-yl]-2',7-dimethyl-1H,2'H-[3,4'-biindazole]-6-carboxylate | 1.32 | 559 | Method_2 |
| #75 | 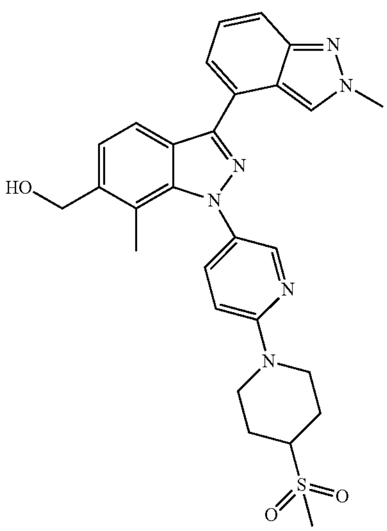 [SMILES: Cc1c(CO)ccc2c(-c3cccc4nn(C)cc34)nn(-c3ccc(N4CCC(S(C)(=O)=O)CC4)nc3)c12] | {1-[6-(4-methanesulfonylpiperidin-1-yl)pyridin-3-yl]-2',7-dimethyl-1H,2'H-[3,4'-biindazol]-6-yl}methanol | 1.09 | 531 | Method_2 |
| #26 | 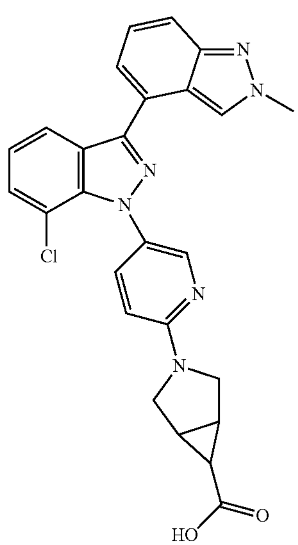 [SMILES: Cn1cc2c(-c3nn(-c4ccc(N5CC6C(C5)C6C(=O)O)nc4)c4c(Cl)cccc34)cccc2n1] | 3-(5-{7-chloro-2'-methyl-1H,2'H-[3,4'-biindazol]-1-yl}pyridin-2-yl)-3-azabicyclo[3.1.0]hexane-6-carboxylic acid | 1.08 | 485 | Method_2 |

-continued
| # | Structure | IUPAC Name | tR [min] | [M + H] | A.M. |
|---|---|---|---|---|---|
| #27 | 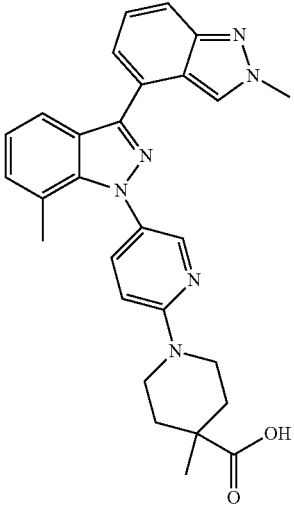 [SMILES: Cc1cccc2c(-c3cccc4nn(C)cc34)nn(-c3ccc(N4CCC(C)(C(=O)O)CC4)nc3)c12] | 1-(5-{2',7-dimethyl-1H,2'H-[3,4'-biindazol]-1-yl}pyridin-2-yl)-4-methylpiperidine-4-carboxylic acid | 1.10 | 481 | Method_2 |
| #28 | 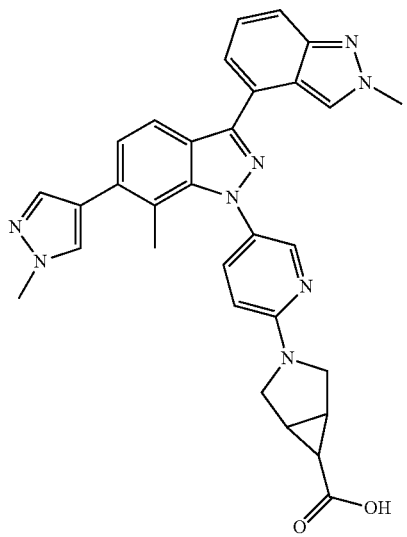 [SMILES: Cc1c(-c2cnn(C)c2)ccc2c(-c3cccc4nn(C)cc34)nn(-c3ccc(N4CC5C(C4)C5C(=O)O)nc3)c12] | 3-{5-[2',7-dimethyl-6-(1-methyl-1H-pyrazol-4-yl)-1H,2'H-[3,4'-biindazol]-1-yl]pyridin-2-yl}-3-azabicyclo[3.1.0]hexane-6-carboxylic acid | 0.99 | 545 | Method_2 |
| #29 | 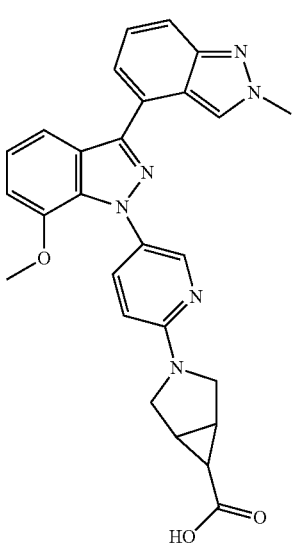 [SMILES: COc1cccc2c(-c3cccc4nn(C)cc34)nn(-c3ccc(N4CC5C(C4)C5C(=O)O)nc3)c12] | 3-(5-{7-methoxy-2'-methyl-1H,2'H-[3,4'-biindazol]-1-yl}pyridin-2-yl)-3-azabicyclo[3.1.0]hexane-6-carboxylic acid | 1.08 | 481 | Method_2 |

| # | Structure | IUPAC Name | tR [min] | [M + H] | A.M. |
| --- | --- | --- | --- | --- | --- |
| #30 | 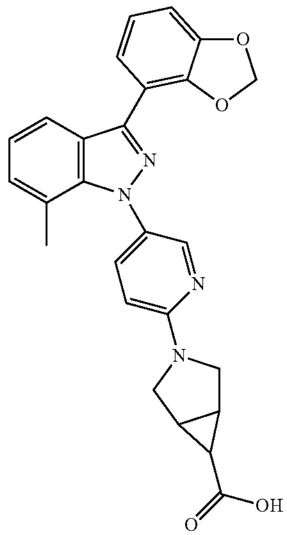 [SMILES: Cc1cccc2c(-c3cccc4c3OCO4)nn(-c3ccc(N4CC5C(C4)C5C(=O)O)nc3)c12] | 3-(5-[3-(2H-1,3-benzodi-oxol-4-yl)-7-methyl-1H-in-dazol-1-yl]pyridin-2-yl}-3-azabicyclo[3.1.0]hexane-6-carboxylic acid | 1.10 | 455 | Method_2 |
| #31 | 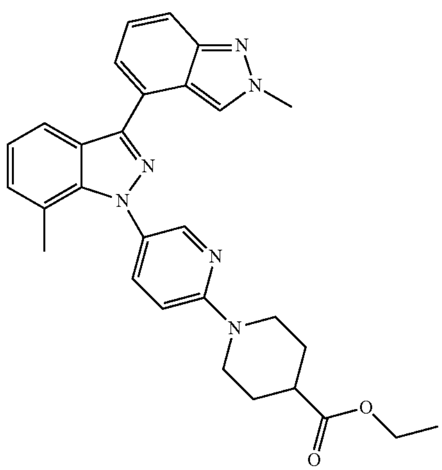 [SMILES: CCOC(=O)C1CCN(c2ccc(-n3nc(-c4cccc5nn(C)cc45)c4cccc(C)c43)cn2)CC1] | ethyl 1-(5-{2',7-dimethyl-1H,2'H-[3,4'-biindazol]-1-yl}pyridin-2-yl)piperidine-4-carboxylate | 1.58 | 495 | Method_2 |
| #32 | 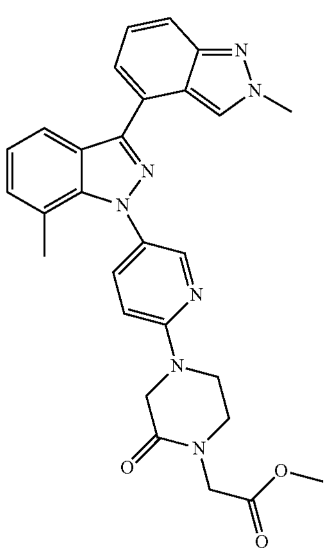 [SMILES: COC(=O)CN1CCN(c2ccc(-n3nc(-c4cccc5nn(C)cc45)c4cccc(C)c43)cn2)CC1=O] | methyl 2-[4-(5-{2',7-di-methyl-1H,2'H-[3,4'-biindazol]-1-yl}pyridin-2-yl)-2-oxopiperazin-1-yl]ac-etate | 0.59 | 510 | Method_3 |

-continued

| # | Structure | IUPAC Name | tR [min] | [M + H] | A.M. |
|---|---|---|---|---|---|
| #33 | 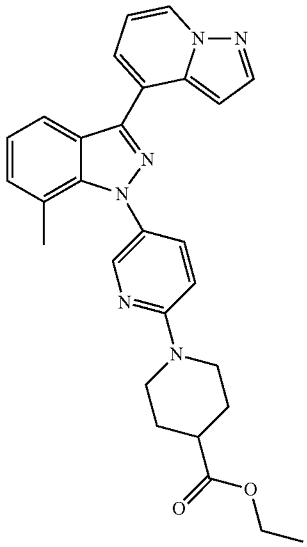 [SMILES: CCOC(=O)C1CCN(c2ccc(-n3nc(-c4cccn5nccc45)c4cccc(C)c43)cn2)CC1] | ethyl 1-[5-(7-methyl-3-{pyrazolo[1,5-a]pyridin-4-yl}-1H-indazol-1-yl)pyridin-2-yl]piperidine-4-carboxylate | 1.136 | 481 | Method_1 |
| #34 | 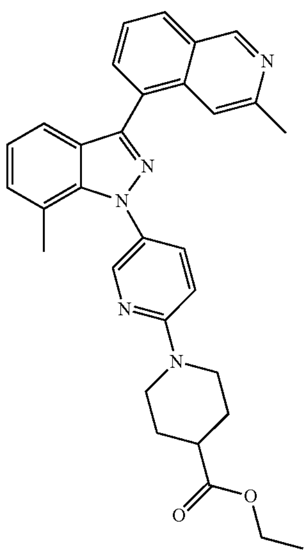 [SMILES: CCOC(=O)C1CCN(c2ccc(-n3nc(-c4cccc5cnc(C)cc45)c4cccc(C)c43)cn2)CC1] | ethyl 1-{5-[7-methyl-3-(3-methylisoquinolin-5-yl)-1H-indazol-1-yl]pyridin-2-yl}piperidine-4-carboxylate | 1.139 | 506 | Method_1 |
| #35 | 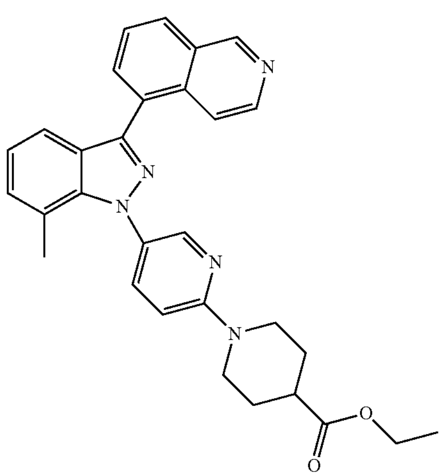 [SMILES: CCOC(=O)C1CCN(c2ccc(-n3nc(-c4cccc5cnccc45)c4cccc(C)c43)cn2)CC1] | ethyl 1-{5-[3-(isoquinolin-5-yl)-7-methyl-1H-indazol-1-yl]pyridin-2-yl}piperidine-4-carboxylate | 1.109 | 492 | Method_1 |

-continued

| # | Structure | IUPAC Name | tR [min] | [M + H] | A.M. |
|---|---|---|---|---|---|
| #36 | 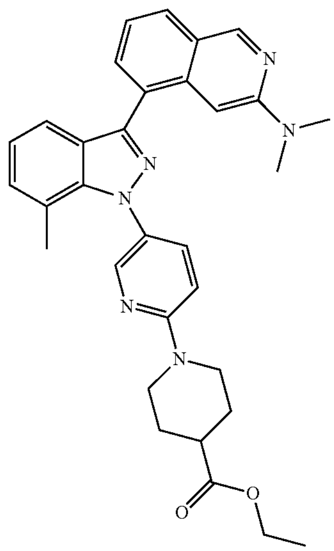 [SMILES: CCOC(=O)C1CCN(c2ccc(-n3nc(-c4cccc5cnc(N(C)C)cc45)c4cccc(C)c43)cn2)CC1] | ethyl 1-(5-{3-[3-(dimethyl-amino)isoquinolin-5-yl]-7-methyl-1H-indazol-1-yl}pyridin-2-yl)piperidine-4-carboxylate | 1.221 | 535 | Method_1 |
| #37 | 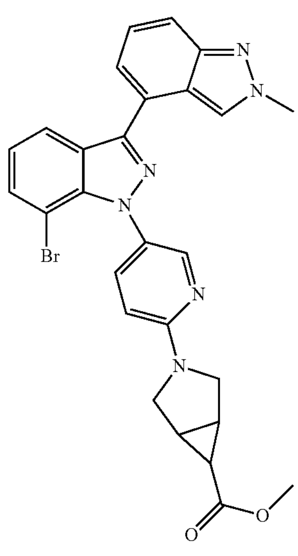 [SMILES: COC(=O)C1C2CN(c3ccc(-n4nc(-c5cccc6nn(C)cc56)c5cccc(Br)c54)cn3)CC21] | methyl 3-(5-{7-bromo-2'-methyl-1H,2'H-[3,4'-biindazol]-1-yl}pyridin-2-yl)-3-azabicyclo[3.1.0]hex-ane-6-carboxylate | 1.089 | 543/545 | Method_1 |

| # | Structure | IUPAC Name | tR [min] | [M + H] | A.M. |
|---|---|---|---|---|---|
| #38 | 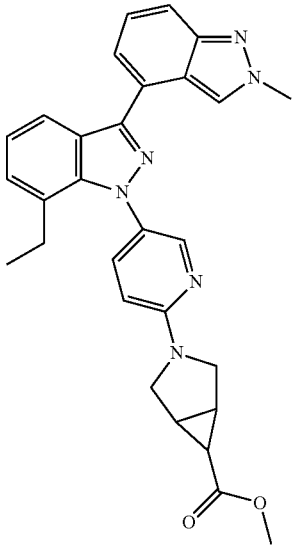 [SMILES: CCc1cccc2c(-c3cccc4nn(C)cc34)nn(-c3ccc(N4CC5C(C4)C5C(=O)OC)nc3)c12] | methyl 3-(5-{7-ethyl-2'-methyl-1H,2'H-[3,4'-biindazol]-1-yl}pyridin-2-yl)-3-azabicyclo[3.1.0]hexane-6-carboxylate | 1.06 | 493 | Method_1 |
| #39 | 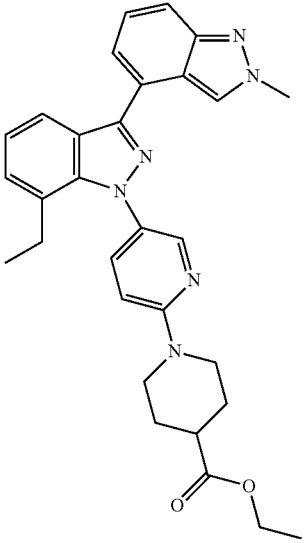 [SMILES: CCOC(=O)C1CCN(c2ccc(-n3nc(-c4cccc5nn(C)cc45)c4cccc(CC)c43)cn2)CC1] | ethyl 1-(5-{7-ethyl-2'-methyl-1H,2'H-[3,4'-biindazol]-1-yl}pyridin-2-yl)piperidine-4-carboxylate | 1.13 | 509 | Method_1 |

-continued
| # | Structure | IUPAC Name | tR [min] | [M + H] | A.M. |
|---|---|---|---|---|---|
| #40 | 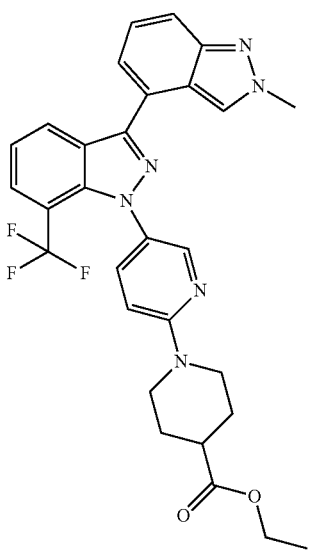 [SMILES: CCOC(=O)C1CCN(c2ccc(-n3nc(-c4cccc5nn(C)cc45)c4cccc(C(F)(F)F)c43)cn2)CC1] | ethyl 1-{5-[2'-methyl-7-(trifluoromethyl)-1H,2'H-[3,4'-biindazol]-1-yl]pyridin-2-yl}piperidine-4-carboxylate | 1.63 | 549 | Method_2 |
| #41 | 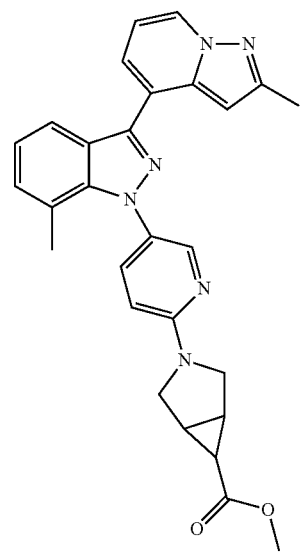 [SMILES: COC(=O)C1C2CN(c3ccc(-n4nc(-c5cccn6nc(C)cc56)c5cccc(C)c54)cn3)CC21] | methyl 3-[5-(7-methyl-3-{2-methylpyrazolo[1,5-a]pyridin-4-yl}-1H-indazol-1-yl)pyridin-2-yl]-3-azabicyclo[3.1.0]hexane-6-carboxylate | 1.54 | 479 | Method_2 |
| #42 | 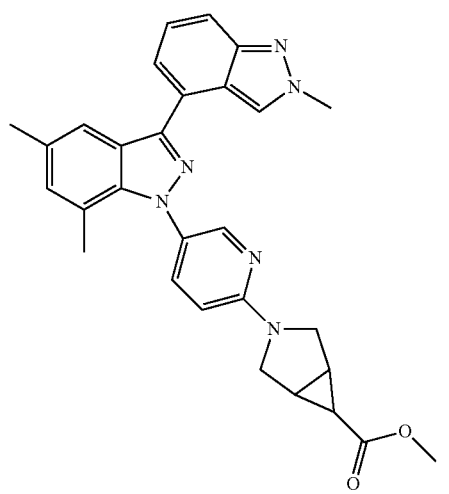 | methyl 3-(5-{2',5,7-trimethyl-1H,2'H-[3,4'-biindazol]-1-yl}pyridin-2-yl)-3-azabicyclo[3.1.0]hexane-6-carboxylate | 1.54 | 493 | Method_2 |

-continued
| # | Structure | IUPAC Name | tR [min] | [M + H] | A.M. |
|---|---|---|---|---|---|
| #43 | 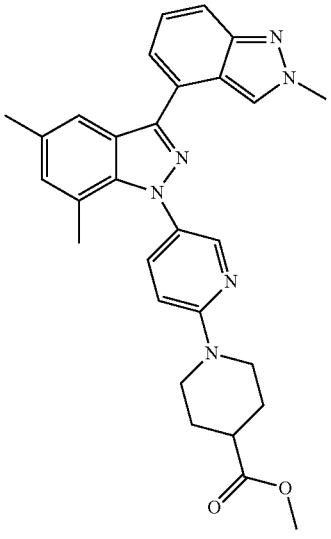 | methyl 1-(5-{2',5,7-tri-methyl-1H,2'H-[3,4'-biindazol]-1-yl}pyridin-2-yl)piperidine-4-carboxylate | 1.66 | 509 | Method_2 |
| #44 | 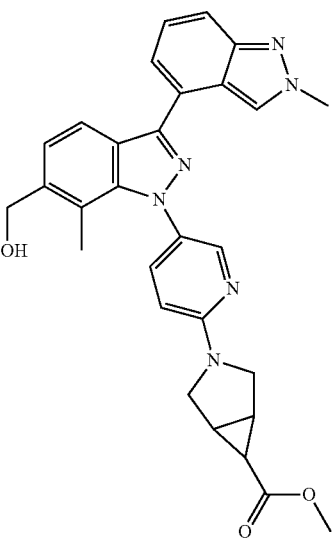 [SMILES: COC(=O)C1C2CN(c3ccc(-n4nc(-c5cccc6nn(C)cc56)c5ccc(CO)c(C)c54)cn3)CC21] | methyl 3-{5-[6-(hydroxymethyl)-2,7-dimethyl-1H,2'H-[3,4'-biindazol]-1-yl] pyridin-2-yl}-3-azabicyclo[3.1.0]hexane-6-carboxylate | 1.22 | 509 | Method_2 |

The following intermediates F are prepared analogously to the synthesis of #1:

| # | Structure | IUPAC Name | tR [min] | [M + H] | A.M. |
|---|---|---|---|---|---|
| F1 | 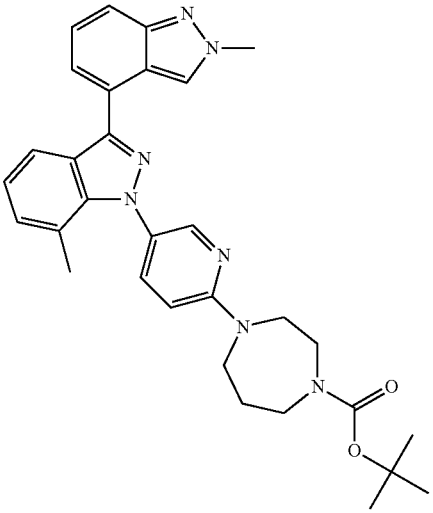 [SMILES: Cc1cccc2c(-c3cccc4nn(C)cc34)nn(-c3ccc(N4CCCN(C(=O)OC(C)(C)C)CC4)nc3)c12] | tert-butyl 4-(5-(2',7-di-methyl-1H,2'H-[3,4'-biindazol]-1-yl)pyridin-2-yl)-1,4-diazepane-1-carboxylate | 1.66 | 538 | Method_2 |
| F2 | 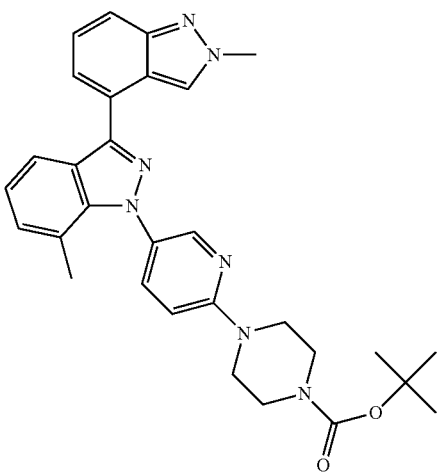 [SMILES: Cc1cccc2c(-c3cccc4nn(C)cc34)nn(-c3ccc(N4CCN(C(=O)OC(C)(C)C)CC4)nc3)c12] | tert-butyl 4-(5-{2',7-di-methyl-1H,2'H-[3,4'-biindazol]-1-yl}pyridin-2-yl)piperazine-1-carboxylate | NA | NA | — |
| F3 | 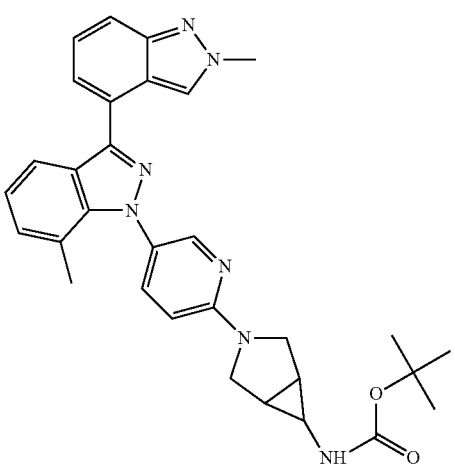 [SMILES: Cc1cccc2c(-c3cccc4nn(C)cc34)nn(-c3ccc(N4CC5C(C4)C5NC(=O)OC(C)(C)C)nc3)c12] | tert-butyl N-[3-(5-{2',7-di-methyl-1H,2'H-[3,4'-biindazol]-1-yl}pyridin-2-yl)-3-azabicyclo[3.1.0]hexan-6-yl]carbamate | 0.76 | 536 | Method_3 |

| # | Structure | IUPAC Name | tR [min] | [M + H] | A.M. |
|---|---|---|---|---|---|
| F4 | 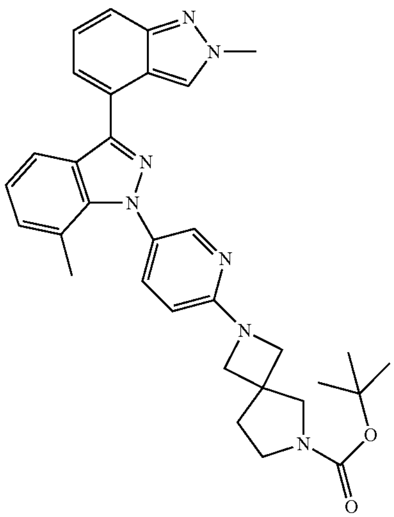 [SMILES: Cc1cccc2c(-c3cccc4nn(C)cc34)nn(-c3ccc(N4CC5(CCN(C(=O)OC(C)(C)C)C5)C4)nc3)c12] | tert-butyl 2-(5-{2',7-dimethyl-1H,2'H-[3,4'-biindazol]-1-yl}pyridin-2-yl)-2,6-diazaspiro[3.4]octane-6-carboxylate | 1.54 | 550 | Method_2 |
| F5 | 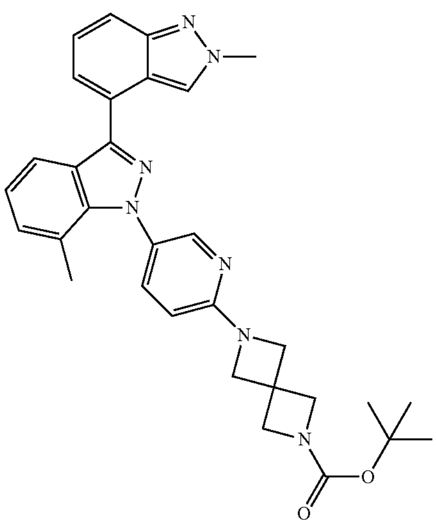 [SMILES: Cc1cccc2c(-c3cccc4nn(C)cc34)nn(-c3ccc(N4CC5(CN(C(=O)OC(C)(C)C)C5)C4)nc3)c12] | tert-butyl 6-(5-{2',7-dimethyl-1H,2'H-[3,4'-biindazol]-1-yl}pyridin-2-yl)-2,6-diazaspiro[3.3]heptane-2-carboxylate | 1.56 | 536 | Method_2 |
| F6 | 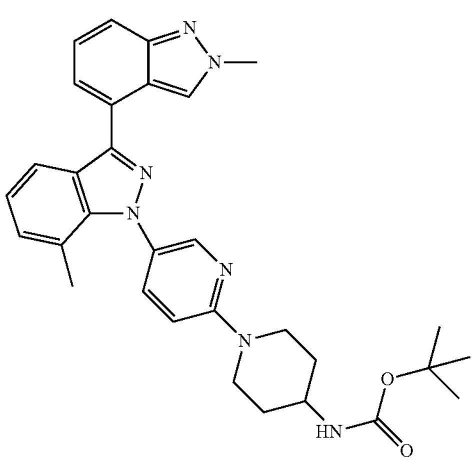 [SMILES: Cc1cccc2c(-c3cccc4nn(C)cc34)nn(-c3ccc(N4CCC(NC(=O)OC(C)(C)C)CC4)nc3)c12] | tert-butyl N-[1-(5-{2',7-dimethyl-1H,2'H-[3,4'-biindazol]-1-yl}pyridin-2-yl)piperidin-4-yl]carbamate | 0.89 | 538 | Method_7 |

Preparation of Examples #45 to #49

45 1-(6-(1,4-diazepan-1-yl)pyridin-3-yl)-2',7-dimethyl-1H,2'H-3,4'-biindazole

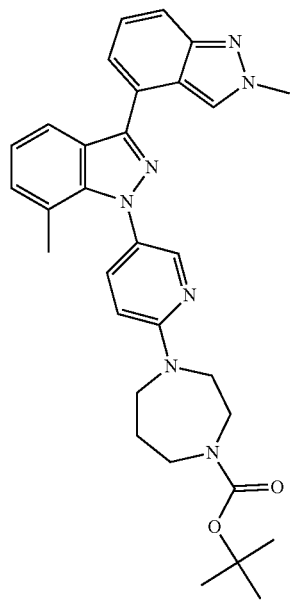

→

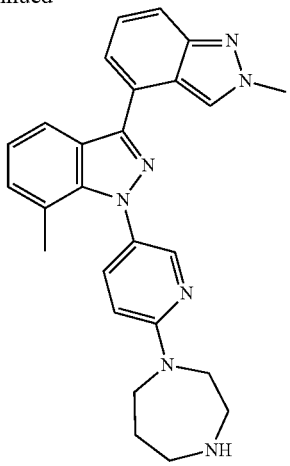

Tert-butyl 4-(5-(2',7-dimethyl-1H,2'H-[3,4'-biindazol]-1-yl)pyridin-2-yl)-1,4-diazepane-1-carboxylate F1 (42 mg, 78 μmol) is stirred at RT in DCM (2 ml) with TFA (400 μl) for 2 h. Toluene (10 ml) is added, the mixture concentrated in vacuo and the product purified by RP chromatography. Yield: 12 mg (35%). HPLC-MS: M+H=438; tR=1.36 min (Method_2)

The following examples are prepared analogously from F2-F6, respectively:

| # | Structure | IUPAC Name | tR [min] | [M + H] | A.M. |
|---|-----------|------------|----------|---------|------|
| #46 | 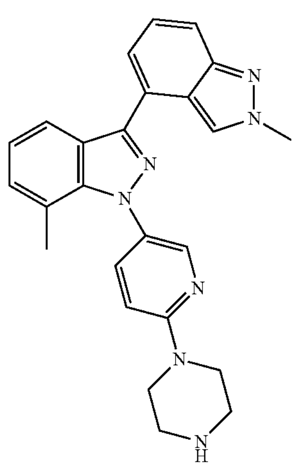 [SMILES: Cc1cccc2c(-c3cccc4nn(C)cc34)nn(-c3ccc(N4CCNCC4)nc3)c12] | 2',7-dimethyl-1-(6-(piperazin-1-yl)pyridin-3-yl)-1H,2'H-3,4'-biindazole | 1.30 | 424 | Method_2 |

| # | Structure | IUPAC Name | tR [min] | [M + H] | A.M. |
|---|---|---|---|---|---|
| #47 | 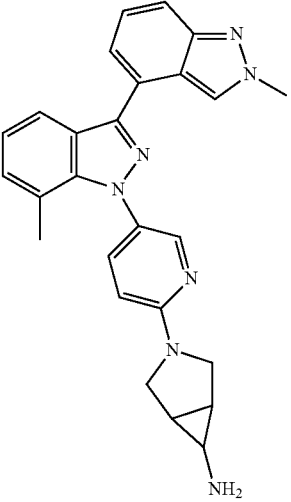 [SMILES: Cc1cccc2c(-c3cccc4nn(C)cc34)nn(-c3ccc(N4CC5C(N)C5C4)nc3)c12] | 3-(5-{2',7-dimethyl-1H,2'H-[3,4'-biindazol]-1-yl}pyridin-2-yl)-3-azabicyclo[3.1.0]hexan-6-amine | 1.29 | 436 | Method_2 |
| #48 | 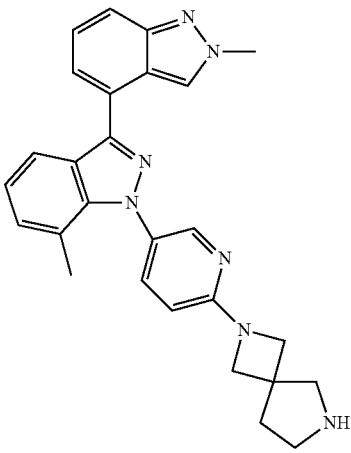 [SMILES: Cc1cccc2c(-c3cccc4nn(C)cc34)nn(-c3ccc(N4CC5(CCNC5)C4)nc3)c12] | 1-(6-2,6-diaza-spiro[3.4]octan-2-yl}pyridin-3-yl)-2',7-dimethyl-1H,2'H-3,4'-biindazole | 1.48 | 450 | Method_2 |
| #49 | 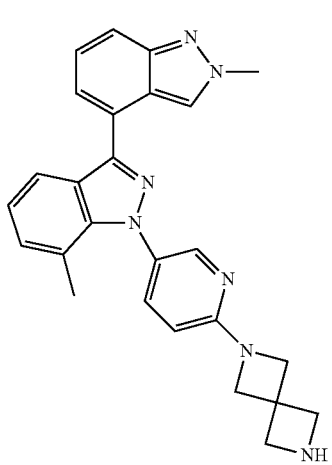 [SMILES: Cc1cccc2c(-c3cccc4nn(C)cc34)nn(-c3ccc(N4CC5(CNC5)C4)nc3)c12] | 1-(6-{2,6-diaza-spiro[3.3]heptan-2-yl}pyridin-3-yl)-2',7-dimethyl-1H,2'H-3,4'-biindazole | 1.31 | 436 | Method_2 |

-continued

| # | Structure | IUPAC Name | tR [min] | [M + H] | A.M. |
|---|---|---|---|---|---|
| #50 | 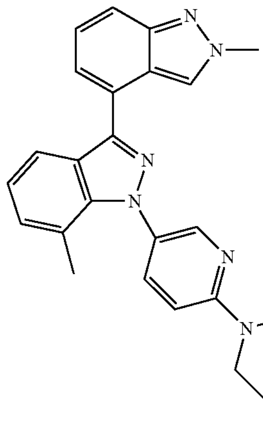 | 1-(5-{2',7-dimethyl-1H,2'H-[3,4'-biindazol]-1-yl}pyridin-2-yl)piperidin-4-amine | 1.31 | 438 | Method_2 |

Preparation of Examples #51 to #54

51 4-(5-(2',7-dimethyl-1H,2'H-[3,4'-biindazol]-1-yl)pyridin-2-yl)piperazine-1-carbaldehyde

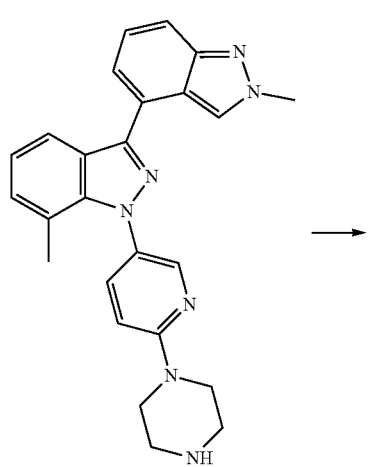

→

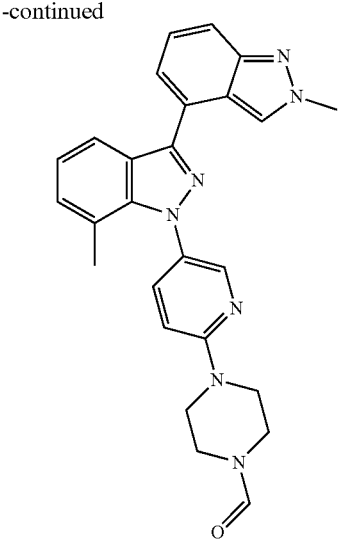

-continued

A mixture of formic acid (2 µl; 53 µmol) and N-methylmorpholine (6 µl; 57 µmol) in DCM (200 µl) is cooled to 0° C. Isobutyl chloroformate (7 µl; 54 µmol) is added and the RM stirred at 20° C. for 2 h. 2',7-dimethyl-1-[6-(piperazin-1-yl)pyridin-3-yl]-1H,2'H-3,4'-biindazole #46 (10 mg, 24 µmol) is added and stirring is continued at RT for 16 h.

The mixture is concentrated in vacuo and the product purified by RP chromatography. Yield: 7 mg (66%). HPLC-MS: M+H=452; tR=1.31 min (Method_2)

The following examples are prepared analogously from #45, #48 and #49, respectively:

| # | Structure | IUPAC Name | tR [min] | [M + H] | A.M. |
|---|---|---|---|---|---|
| #52 | 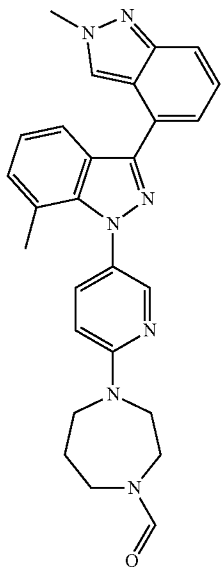 [SMILES: Cc1cccc2c(-c3cccc4nn(C)cc34)nn(-c3ccc(N4CCCN(C=O)CC4)nc3)c12] | 4-(5-{2',7-dimethyl-1H,2'H-[3,4'-biindazol]-1-yl}pyridin-2-yl)-1,4-diazepane-1-carbaldehyde | 1.30 | 466 | Method_2 |
| #53 | 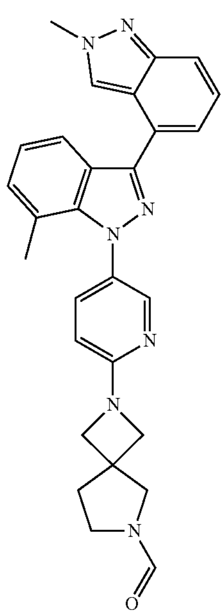 [SMILES: Cc1cccc2c(-c3cccc4nn(C)cc34)nn(-c3ccc(N4CC5(CCN(C=O)C5)C4)nc3)c12] | 2-(5-{2',7-dimethyl-1H,2'H-[3,4'-biindazol]-1-yl}pyridin-2-yl)-2,6-diazaspiro[3.4]octane-6-carbaldehyde | 1.26 | 478 | Method_2 |

| # | Structure | IUPAC Name | tR [min] | [M + H] | A.M. |
|---|---|---|---|---|---|
| #54 | 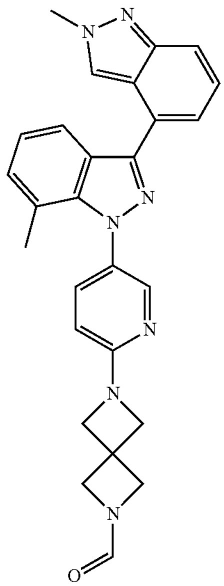 [SMILES: Cc1cccc2c(-c3cccc4nn(C)cc34)nn(-c3ccc(N4CC5(CN(C=O)C5)C4)nc3)c12] | 6-(5-{2',7-dimethyl-1H,2'H-[3,4'-biindazol]-1-yl}pyridin-2-yl)-2,6-diaza-spiro[3.3]heptane-2-carbaldehyde | 1.23 | 464 | Method_2 |

55 N-[3-(5-{2',7-dimethyl-1H,2'H-[3,4'-biindazol]-1-yl}pyridin-2-yl)-3-azabicyclo[3.1.0]hexan-6-yl] acetamide

→

-continued

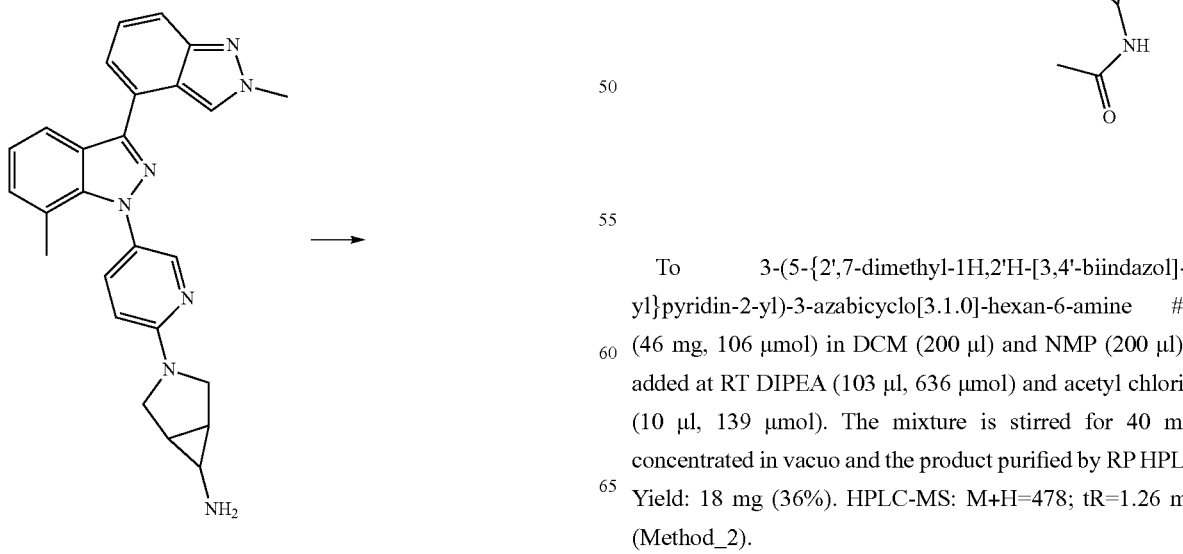

To 3-(5-{2',7-dimethyl-1H,2'H-[3,4'-biindazol]-1-yl}pyridin-2-yl)-3-azabicyclo[3.1.0]-hexan-6-amine #47 (46 mg, 106 μmol) in DCM (200 μl) and NMP (200 μl) is added at RT DIPEA (103 μl, 636 μmol) and acetyl chloride (10 μl, 139 μmol). The mixture is stirred for 40 min, concentrated in vacuo and the product purified by RP HPLC. Yield: 18 mg (36%). HPLC-MS: M+H=478; tR=1.26 min (Method_2).

56 N-[1-(5-{2',7-dimethyl-1H,2'H-[3,4'-biindazol]-1-yl}pyridin-2-yl)piperidin-4-yl]methanesulfonamide

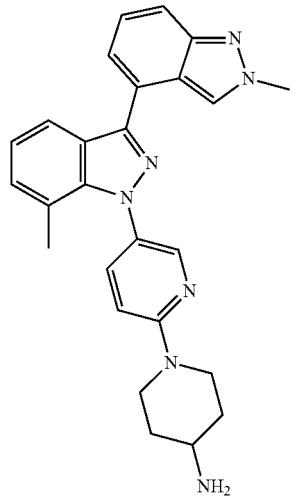

A mixture of 1-(5-{2',7-dimethyl-1H,2'H-[3,4'-biindazol]-1-yl}pyridin-2-yl)piperidin-4-amine #50 (45 mg, 103 μmol), triethylamine (250 μl, 1.8 mmol), NMP (750 μl) and methanesulfonyl chloride (18 μl, 235 μmol) is stirred at RT for 1 h. The mixture is concentrated in vacuo and the product purified by RP HPLC. Yield: 23 mg (43%). HPLC-MS: M+H=516; tR=1.36 min (Method_2).

Preparation of Examples #57 to #71

57 1-(5-(2',7-dimethyl-1H,2'H-[3,4'-biindazol]-1-yl)pyridin-2-yl)piperidine-4-carboxylic acid

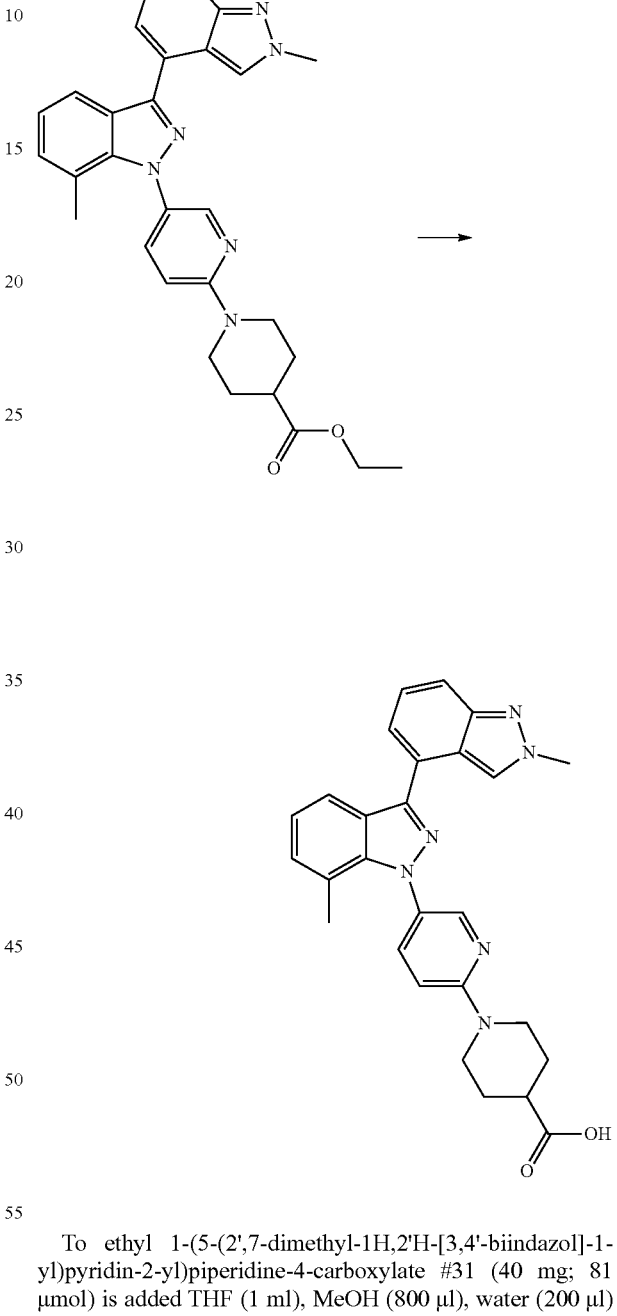

To ethyl 1-(5-(2',7-dimethyl-1H,2'H-[3,4'-biindazol]-1-yl)pyridin-2-yl)piperidine-4-carboxylate #31 (40 mg; 81 μmol) is added THF (1 ml), MeOH (800 μl), water (200 μl) and LiOH (19 mg; 793 μmol). The mixture is stirred at RT for 2 h. After neutralization with aqueous 1N HCl the mixture is extracted with EtOAc. The combined organic layers are dried over MgSO₄, concentrated in vacuo and the product purified by RP HPLC. Yield: 35 mg (93%). HPLC-MS: M+H=467; tR=1.03 min (Method_2).

The following examples are prepared analogously from #32, #1, #33-#44, respectively:

| # | Structure | IUPAC Name | tR [min] | [M + H] | A.M. |
|---|---|---|---|---|---|
| #58 | 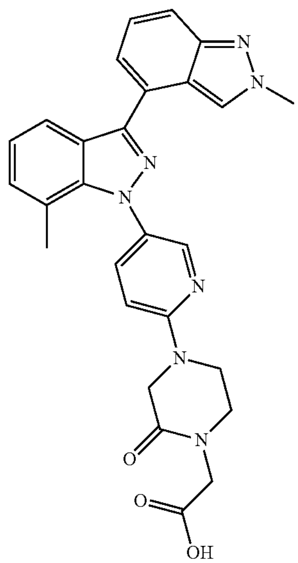 [SMILES: Cc1cccc2c(-c3cccc4nn(C)cc34)nn(-c3ccc(N4CCN(CC(=O)O)C(=O)C4)nc3)c12] | 2-[4-(5-{2',7-dimethyl-1H,2'H-[3,4'-biindazol]-1-yl}pyridin-2-yl)-2-oxopiperazin-1-yl]acetic acid | 1.04 | 496 | Method_2 |
| #59 | 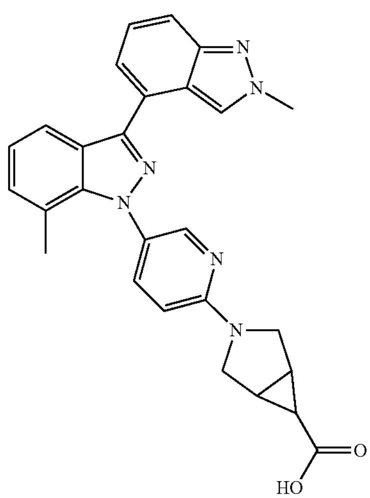 [SMILES: Cc1cccc2c(-c3cccc4nn(C)cc34)nn(-c3ccc(N4CC5C(C4)C5C(=O)O)nc3)c12] | 3-(5-{2',7-dimethyl-1H,2'H-[3,4'-biindazol]-1-yl}pyridin-2-yl)-3-azabicyclo[3.1.0]hexane-6-carboxylic acid | 1.07 | 465 | Method_2 |
| #60 | 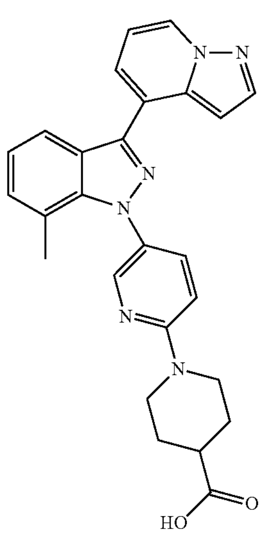 [SMILES: Cc1cccc2c(-c3cccn4nccc34)nn(-c3ccc(N4CCC(C(=O)O)CC4)nc3)c12] | 1-[5-(7-methyl-3-{pyrazolo[1,5-a]pyridin-4-yl}-1H-indazol-1-yl)pyridin-2-yl]piperidine-4-carboxylic acid | 1.03 | 453 | Method_2 |

| # | Structure | IUPAC Name | tR [min] | [M + H] | A.M. |
|---|---|---|---|---|---|
| #61 | 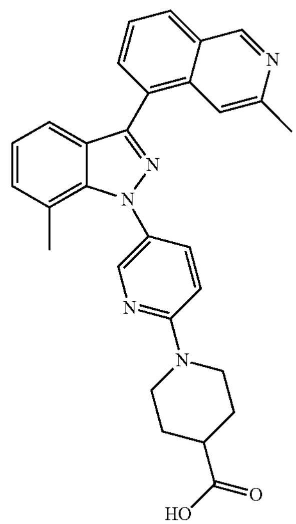 [SMILES: Cc1cc2c(-c3nn(-c4ccc(N5CCC(C(=O)O)CC5)nc4)c4c(C)cccc34)cccc2cn1] | 1-{5-[7-methyl-3-(3-methylisoquinolin-5-yl)-1H-indazol-1-yl]pyridin-2-yl}piperidine-4-carboxylic acid | 1.09 | 478 | Method_2 |
| #62 | 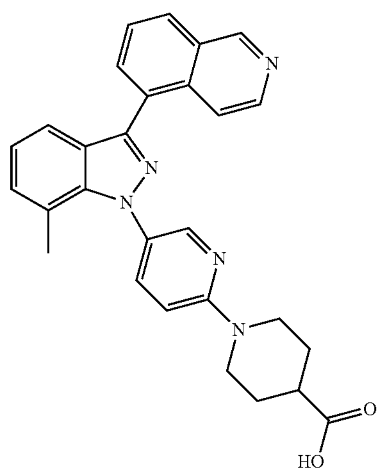 [SMILES: Cc1cccc2c(-c3cccc4cnccc34)nn(-c3ccc(N4CCC(C(=O)O)CC4)nc3)c12] | 1-{5-[3-(isoquinolin-5-yl)-7-methyl-1H-indazol-1-yl]pyridin-2-yl}piperidine-4-carboxylic acid | 0.91 | 464 | Method_2 |
| #63 | 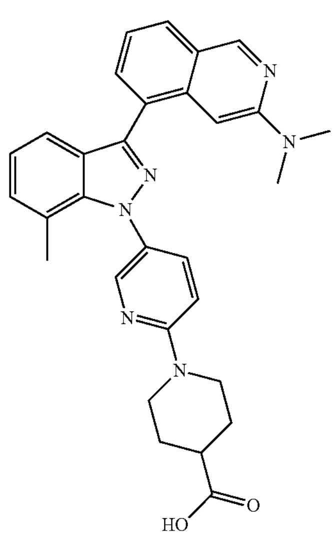 [SMILES: Cc1cccc2c(-c3cccc4cnc(N(C)C)cc34)nn(-c3ccc(N4CCC(C(=O)O)CC4)nc3)c12] | 1-(5-{3-[3-(dimethylamino)isoquinolin-5-yl]-7-methyl-1H-indazol-1-yl}pyridin-2-yl)piperidine-4-carboxylic acid | 1.19 | 507 | Method_2 |

-continued

| # | Structure | IUPAC Name | tR [min] | [M + H] | A.M. |
|---|---|---|---|---|---|
| #64 | 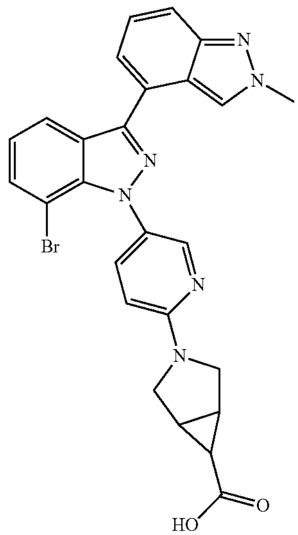 [SMILES: Cn1cc2c(-c3nn(-c4ccc(N5CC6C(C5)C6C(=O)O)nc4)c4c(Br)cccc34)cccc2n1] | 3-(5-{7-bromo-2'-methyl-1H,2'H-[3,4'-biindazol]-1-yl}pyridin-2-yl)-3-azabicyclo[3.1.0]hexane-6-carboxylic acid | 1.09 | 529 | Method_2 |
| #65 | 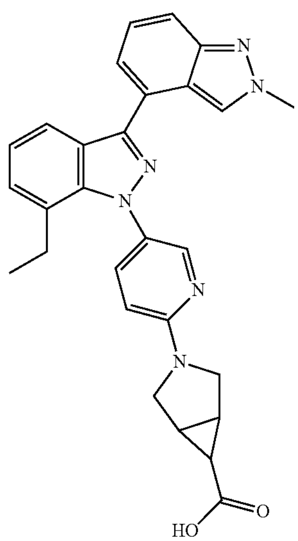 [SMILES: CCc1cccc2c(-c3cccc4nn(C)cc34)nn(-c3ccc(N4CC5C(C4)C5C(=O)O)nc3)c12] | 3-(5-{7-ethyl-2'-methyl-1H,2'H-[3,4'-biindazol]-1-yl}pyridin-2-yl)-3-azabicyclo[3.1.0]hexane-6-carboxylic acid | 1.11 | 479 | Method_2 |
| #66 | 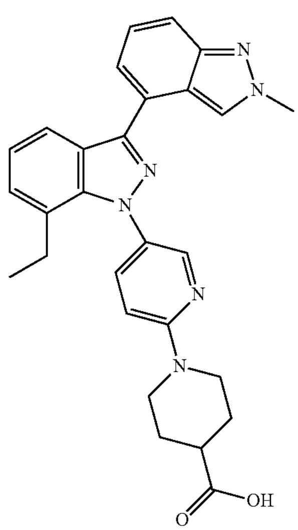 [SMILES: CCc1cccc2c(-c3cccc4nn(C)cc34)nn(-c3ccc(N4CCC(C(=O)O)CC4)nc3)c12] | 1-(5-{7-ethyl-2'-methyl-1H,2'H-[3,4'-biindazol]-1-yl}pyridin-2-yl)piperidine-4-carboxylic acid | 1.14 | 481 | Method_2 |

| # | Structure | IUPAC Name | tR [min] | [M + H] | A.M. |
|---|---|---|---|---|---|
| #67 | 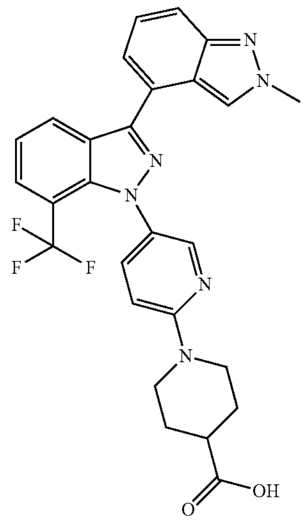 [SMILES: Cn1cc2c(-c3nn(-c4ccc(N5CCC(C(=O)O)CC5)nc4)c4c(C(F)(F)F)cccc34)cccc2n1] | 1-{5-[2'-methyl-7-(trifluoromethyl)-1H,2'H-[3,4'-biindazol]-1-yl]pyridin-2-yl}piperidine-4-carboxylic acid | 1.63 | 521 | Method_2 |
| #68 | 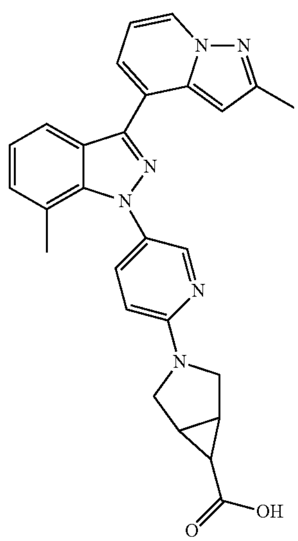 [SMILES: Cc1cc2c(-c3nn(-c4ccc(N5CC6C(C5)C6C(=O)O)nc4)c4c(C)cccc34)cccn2n1] | 3-[5-(7-methyl-3-{2-methylpyrazolo[1,5-a]pyridin-4-yl}-1H-indazol-1-yl)pyridin-2-yl]-3-azabicyclo[3.1.0]hexane-6-carboxylic acid | 1.05 | 465 | Method_2 |
| #69 | 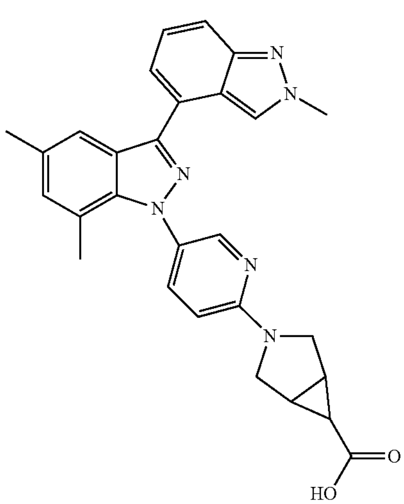 [SMILES: Cc1cc(C)c2c(c1)c(-c1cccc3nn(C)cc13)nn2-c1ccc(N2CC3C(C2)C3C(=O)O)nc1] | 3-(5-{2',5,7-trimethyl-1H,2'H-[3,4'-biindazol]-1-yl}pyridin-2-yl)-3-azabicyclo[3.1.0]hexane-6-carboxylic acid | 2.09 | 479 | Method_2 |

| # | Structure | IUPAC Name | tR [min] | [M + H] | A.M. |
|---|---|---|---|---|---|
| #70 | 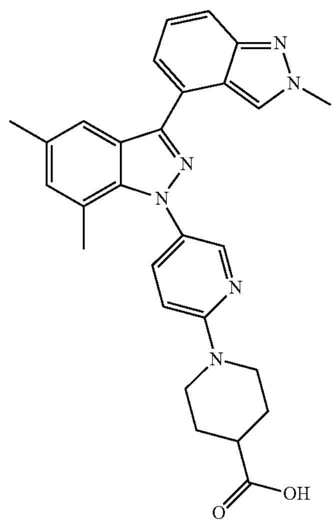 | 1-(5-{2',5,7-trimethyl-1H,2'H-[3,4'-biindazol]-1-yl}pyridin-2-yl)piperidine-4-carboxylic acid | 1.08 | 481 | Method_2 |
| #71 | 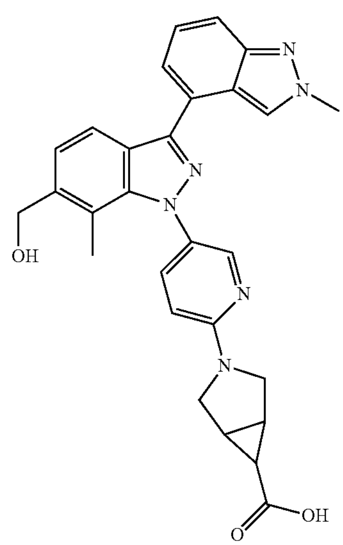 [SMILES: Cc1c(CO)ccc2c(-c3cccc4nn(C)cc34)nn(-c3ccc(N4CC5C(C4)C5C(=O)O)nc3)c12] | 3-{5-[6-(hydroxymethyl)-2',7-dimethyl-1H,2'H-[3,4'-biindazol]-1-yl]pyridin-2-yl}-3-azabicyclo[3.1.0]hexane-6-carboxylic acid | 0.88 | 495 | Method_2 |

Further Examples are Obtained by Additional Chemical Transformations

72 3-(5-{2',7-dimethyl-1H,2'H-[3,4'-biindazol]-1-yl}pyridin-2-yl)-3-azabicyclo[3.1.0]hexane-6-carboxamide

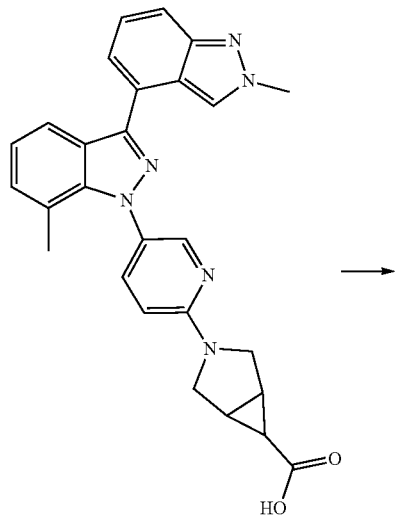

To a mixture of 3-(5-{2',7-dimethyl-1H,2'H-[3,4'-biindazol]-1-yl}pyridin-2-yl)-3-azabicyclo[3.1.0]hexane-6-carboxylic acid #1 (20 mg, 43 µmol), DIPEA (22 µl, 129 µmol) in NMP (500 µl) is added HATU (25 mg, 66 µmol) and the mixture stirred at RT for 10 min. Ammonium chloride (10 mg, 187 µmol) is added and stirring continued for 16 h. The mixture is concentrated in vacuo and the product purified by RP chromatography. Yield: 11 mg (55%). HPLC-MS: M+H=464; tR=1.28 min (Method_2).

Starting from intermediate S2 example #73 is synthesized with building blocks V:

V1 5-bromo-2-(4-methanesulfonylphenyl)pyridine

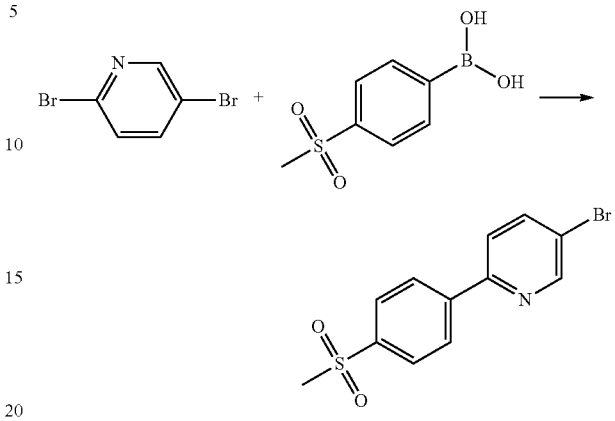

A mixture of 2,5-dibromopyridine (50 mg, 211 µmol), (4-methanesulfonylphenyl)boronic acid (42 mg, 211 mmol) and tetrakis(triphenylphosphine)palladium (25 mg, 21 µmol), dioxane (1 ml) and aqueous sodium carbonate solution (2 mol/l, 264 µl, 528 µmol) is stirred under argon atmosphere for 2 h at 80° C. At RT water (100 ml) is added and the mixture extracted with EtOAc. The combined organic layers are dried over MgSO$_4$, concentrated in vacuo and the product purified by RP HPLC. Yield: 43 mg (65%). HPLC-MS: M+H=312/314; tR=0.57 min (Method_8).

V2 [6-(4-methanesulfonylphenyl)pyridin-3-yl]boronic acid

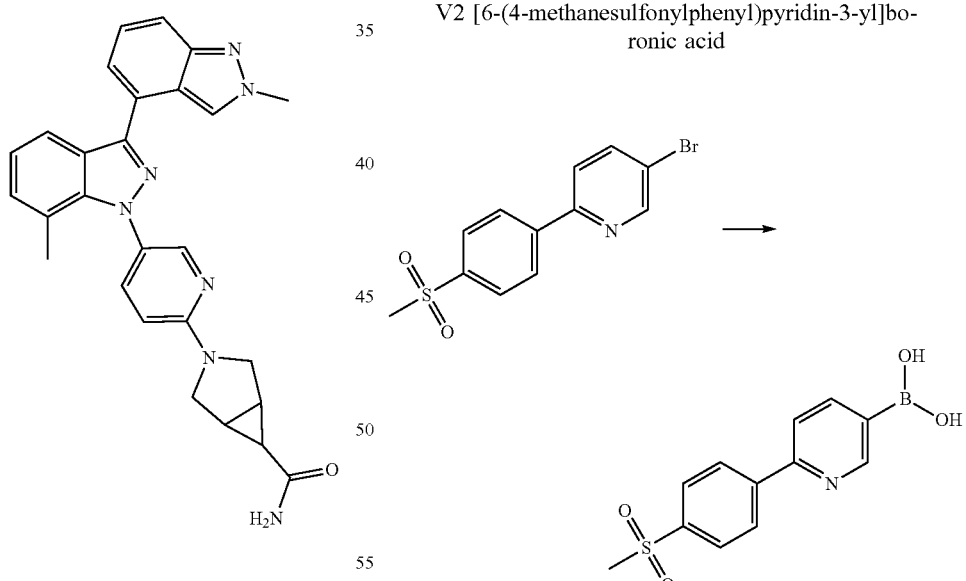

A mixture of 5-bromo-2-(4-methanesulfonylphenyl)pyridine V1 (450 mg, 1.44 mmol), bis(pinacolato)diboron (732 mg, 2.88 mmol), 1,1'-bis(diphenylphosphino)ferrocene]dichloropalladium(II) (121 mg, 144 µmol) and potassium acetate (707 mg, 7.2 mmol) in dioxane (9 ml) is stirred under argon atmosphere for 1 h at 80° C. The solids are filtered off, the filtrate is concentrated in vacuo and the product purified by RP chromatography. Yield: 245 mg (61%). HPLC-MS: M+H=278; tR=0.24 min (Method_2).

73 1-[6-(4-methanesulfonylphenyl)pyridin-3-yl]-2',7-dimethyl-1H,2'H-3,4'-biindazole Example #74 is Synthesized Via W1

W1 methyl 3-(5-{2'-methyl-7-[2-(trimethylsilyl)ethynyl]-1H,2'H-[3,4'-biindazol]-1-yl}pyridin-2-yl)-3-azabicyclo[3.1.0]hexane-6-carboxylate

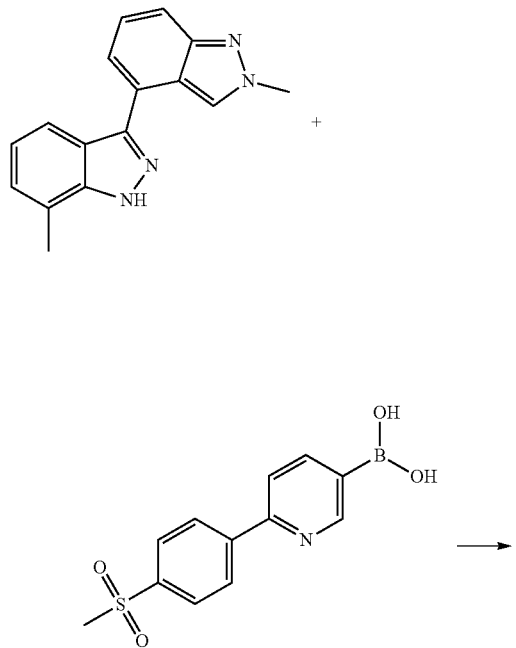

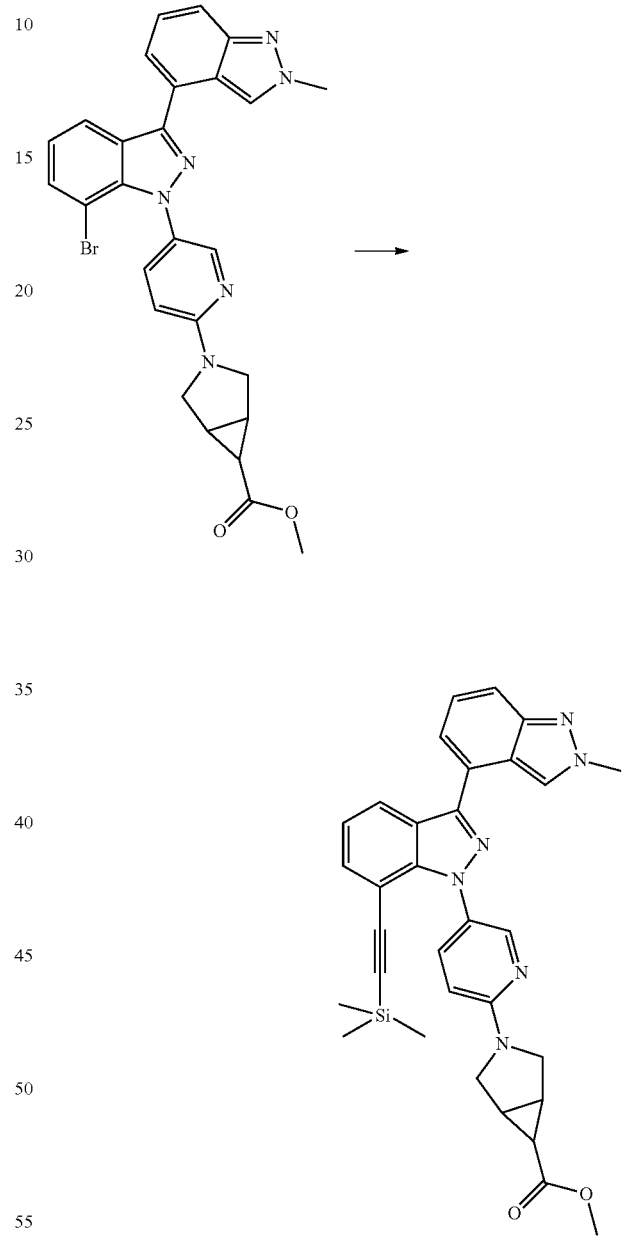

To a mixture of 2',7-dimethyl-1H,2'H-3,4'-biindazole S2 (26 mg, 99 µmol) in ACN (1 ml) and DCM (1 ml) is added pyridine (24 µl, 300 µmol), [6-(4-methanesulfonylphenyl)pyridin-3-yl]boronic acid V2 (87 mg, 303 µmol) and copper (II) acetate (27 mg, 149 µmol). The mixture is stirred for 3 days at 80° C. The solids are filtered off, the filtrate is concentrated in vacuo and the product purified by RP chromatography. Yield: 4.3 mg (9%). HPLC-MS: M+H=494; tR=0.74 min (Method_8).

Dichlorobis(triphenylphosphine)palladium(II) (13 mg, 19 µmol) is added to a mixture of methyl 3-(5-{7-bromo-2'-methyl-1H,2'H-[3,4'-biindazol]-1-yl}pyridin-2-yl)-3-azabicyclo[3.1.0]hexane-6-carboxylate #37 (100 mg, 184 µmol), ethynyltrimethylsilane (181 mg, 1.8 mmol), copper(I) iodide (4 mg, 21 µmol), DIPEA (94 µl, 550 µmol) and NMP (2 ml) under argon atmosphere at RT and is stirred at 50° C. for 4 h. The mixture is concentrated in vacuo and the product purified by RP HPLC. Yield: 24 mg (23%). HPLC-MS: M+H=561; tR=1.214 min (Method_1).

74 3-(5-{7-ethynyl-2'-methyl-1H,2'H-[3,4'-biindazol]-1-yl}pyridin-2-yl)-3-azabicyclo[3.1.0]hexane-6-carboxylic acid

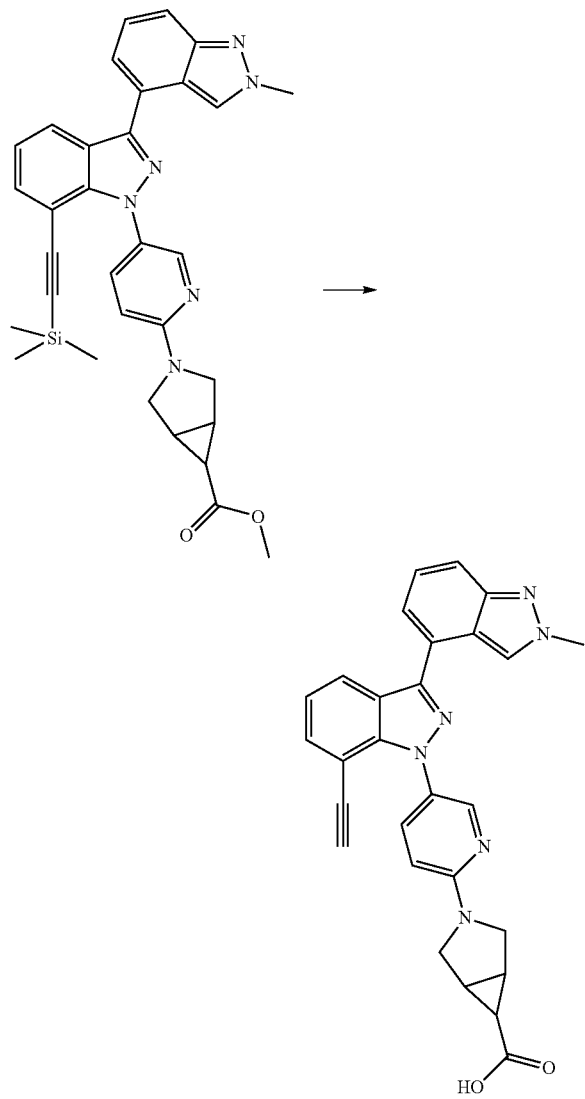

To methyl 3-(5-{2'-methyl-7-[2-(trimethylsilyl)ethynyl]-1H,2'H-[3,4'-biindazol]-1-yl}pyridin-2-yl)-3-azabicyclo[3.1.0]hexane-6-carboxylate W1 (24 mg; 43 μmol) is added THF (1 ml), MeOH (800 μl), water (200 μl) and LiOH (10 mg, 412 μmol). The mixture is stirred at RT for 2 h, concentrated in vacuo and the product purified by RP HPLC. Yield: 2 mg (10%). HPLC-MS: M+H=475; tR=0.777 min (Method_1).

For examples #1, 26, 28, 29, 30, 37, 38, 41, 42, 44, 47, 55, 59, 64, 65, 68, 69, 71, 72, 74 the following values reported represent the isomers containing a (1R,5S,6R)-3-azabicyclo[3.1.0]hexane-6-carboxylic acid or (1R,5S,6S)-3-azabicyclo[3.1.0]hexan-6-amine moiety. In case of example #6 the data of the (R) isomer is shown.

Pharmacological Activity

Interaction with hSTING as Determined by Differential Scanning Fluorimetry (DSF)

In DSF, the temperature at which a protein unfolds, also called the melting temperature $T_m$, is measured by changes in fluorescence of a dye that binds to the hydrophobic parts of the protein. $T_m$ shifts upon binding of a small molecule are correlated with the binding affinity of this small molecule. As target protein, Human STING (hSTING, residues 155-341, MW: 21578.4 Da; protein stock solution: c=1302 μM stock solution in 20 mM Tris, 100 mM NaCl, 2 mM TCEP pH 8.8) was used, as assay buffer 20 mM Tris, 150 mM NaCl pH7.5 was added where and as necessary.

Final concentrations of components in assay: 100 μM test compounds, 5 μM target protein, "5×" SYPR Orange (from stock solution SYPRO orange solution in DMSO (invitrogen cat.-no. S6650-500 ul), concentration "5000×")

Assay Procedure:

1) Dilutions of compound stock solutions (10 mM in DMSO) were prepared in assay buffer (20 mM Tris, 150 mM NaCl; pH7.5)

2) 5 μl fluorescent dye stock solution (5000×SYPRO Orange in DMSO) was mixed with 19 μl target protein (1302 μM) and 976 μl assay buffer.

3) 2 μl of this protein-dye-mixture (25×SYPRO Orange and 25 μM Protein) was added to 8 μl diluted compound solution as prepared in step 1. Final volume was 10 μl.

4) With every 20 compounds, two negative controls were measured.

5) The plates were prepared for duplicate measurement and centrifuged for 2 min at 1000 g.

6) For the measurement, a CFX384 Real-Time System (Bio-Rad) was used. The run consisted of 140 cycles with 0.5° C./cycle (temperature ramp 15 s/cycle, 25° C. to 95° C.).

Data analysis: The melting curves were processed in Bio-Rad CFX Manager. Peak type was set to "negative". Two replicates of TM (melting temperature) measurements were averaged and the standard deviation was calculated.

The changes in TM ("thermal shift") are shown in table 1.

TABLE 1

Interaction with hSTING as determined by DSF

| Example | | | | | | | | | | | | | | | | | | |
|---|---|---|---|---|---|---|---|---|---|---|---|---|---|---|---|---|---|---|
| | #1 | #2 | #3 | #4 | #6 | #7 | #8 | #9 | #10 | #11 | #12 | #14 | #15 | #17 | #18 | #19 | #20 | #21 |
| TM [K] | 21 | 22 | 20 | 20 | 22 | 22 | 21 | 23 | 20 | 21 | 21 | 18 | 21 | 16 | 22 | 21 | 20 | 20 |

| Example | | | | | | | | | | | | | | | | | |
|---|---|---|---|---|---|---|---|---|---|---|---|---|---|---|---|---|---|
| | #22 | #25 | #27 | #28 | #29 | #30 | #45 | #51 | #52 | #53 | #54 | #55 | #56 | #57 | #58 | #59 | #61 | #62 |
| TM [K] | 23 | 25 | 22 | 27 | 22 | 20 | 19 | 15 | 21 | 20 | 21 | 20 | 20 | 17 | 23 | 21 | 16 | 20 |

TABLE 1-continued

Interaction with hSTING as determined by DSF

| | Example | | | | | | | | |
|---|---|---|---|---|---|---|---|---|---|
| | #63 | #65 | #66 | #67 | #68 | #71 | #72 | #74 | #75 |
| TM [K] | 19 | 21 | 16 | 23 | 24 | 29 | 18 | 16 | 26 |

In Vitro Cytokine Induction Measured Via Activation of an Interferon Regulatory Factor Inducible Reporter Gene The cytokine-induction activities of compounds according to the present invention have been demonstrated by using a THP1 reporter cell line, thereby resulting in cellular EC50 values. Activation of the STING protein expressed in cell lines results in an increase of interferon production. By the stable integration of an interferon regulatory factor (IRF)-inducible SEAP gene (secreted embryonic alkaline phosphatase) reporter construct the functional interferon signaling pathway can be monitored. Using Invivogen's THP1-Blue™ ISG colorimetric enzyme assay and a suitable optical density (OD) reader the activity of SEAP can be detected and quantified. This technique could be used to characterize pharmacological modification of the STING pathway.

Several single nucleotide polymorphisms have been identified in the human STING gene. To determine the activity of the above described compounds, THP1-Blue™ ISG reporter cell lines expressing the different human STING variants have been generated. To do so, the endogenous human STING was first deleted using the CRISPR/CAS9 system: THP1-Blue ISG cells were electroporated with ALL-IN-ONE CRISPR plasmids targeting the STING gene (purchased from Sigma encoding the gRNA and GFP as a reporter gene for successful transduction). GFP positive cells then were sorted 24 h post transfection and expanded. Cells were then dispersed in semisolid methocel medium to allow single cell clone isolations. Clones were then screened for cGAMP responsiveness using the Quanti-Blue™ reporter assay. Non-responsive clones were subsequently analysed for STING loss by western blotting and sequencing of the STING locus.

For the overexpression of the human STING variants, a confirmed THP1-Blue™ ISG hSTING KO clone was transduced with individual retroviral plasmids (MSCV-ires-GFP-Blasti) encoding the allelic variants of hSTING (WT (H232R), HAQ, R232H, AQ and R293Q). Transduced cells were sorted for different levels of GFP fluorescence and STING allele expression was analysed by western blot. Populations expressing ectopic STING protein (WT, HAQ, R232H, AQ and R293Q) at comparable levels to endogenous STING levels from the parental, unmodified THP1-Blue ISG cell lines were selected and used for compound characterization.

Measurements of SEAP activity were performed in THP1-Blue™ ISG cells stably expressing the different human STING isoforms and the IRF-inducible SEAP reporter construct. Cells were cultivated in RPMI1640 medium with 10% fetal calf serum, 50 µg/ml Penicillin-Streptomycin, 100 µg/ml Zeocin, and 100 µg/ml Normocin in a 37°, 95% humidity and 5% $CO_2$ incubator.

In preparation for the assay, the cells were distributed into the assay plates with a density of 10000 cells/15 µL per well. Compounds were prepared by an 8 point serial dilution in 50% aqueous DMSO and a final dilution step into medium to ensure a final DMSO concentration of 0.5% in the assay. 5 µL of diluted compounds were added to the plates, followed by a 24 hours incubation at 37° C.

At the day of the assay, 75 µl per well of Quanti-Blue™ reagent was added to all wells of the plate and the plate was incubated another 30 minutes at 37° C. The OD at 620 nm was measured on the EnVision reader (PerkinElmer).

$EC_{50}$ values and Hill slopes were derived from 8-point four parametric non-linear curve fittings with the Megalab software (Boehringer Ingelheim) using the OD at 620 nM. Data of $EC_{50}$ values can be found in tables 2a-2e.

Data of $EC_{50}$ values on STING HAQ-variant can be found in table 2a. Shown data below were either derived from the parental THP1-Blue™ ISG cell lines (which express endogenously HAQ) or from genetically engineered THP1-Blue™ ISG cell lines in which first STING has been knocked-out and the HAQ specific STING isoform has been re-introduced as described above.

TABLE 2a

| | Example | | | | | | | | | | | | | | | | | | | | | | | | | |
|---|---|---|---|---|---|---|---|---|---|---|---|---|---|---|---|---|---|---|---|---|---|---|---|---|---|---|
| | #1 | #2 | #3 | #4 | #5 | #6 | #7 | #8 | #9 | #10 | #11 | #12 | #14 | #15 | #17 | #18 | #19 | #20 | #21 | #22 | #24 | #25 | #26 | #27 |
| $EC_{50}$ [µM] | 0.7 | 0.6 | 3.0 | 1.1 | 1.4 | 3.1 | 0.8 | 1.2 | 1.0 | 2.1 | 3.2 | 1.9 | 6.9 | 1.0 | 6.8 | 0.7 | 6.5 | 2.2 | 4.7 | 0.7 | 2.7 | 0.2 | 0.9 | 5.2 |

| | Example | | | | | | | | | | | | | | | | | | | | |
|---|---|---|---|---|---|---|---|---|---|---|---|---|---|---|---|---|---|---|---|---|---|
| | #28 | #29 | #30 | #31 | #45 | #51 | #52 | #53 | #54 | #55 | #56 | #57 | #58 | #59 | #60 | #61 | #62 | #63 | #64 | #65 | #66 | #67 | #68 | #69 |
| $EC_{50}$ [µM] | 0.08 | 0.8 | 6.1 | 5.4 | 1.9 | 0.3 | 1.9 | 1.7 | 2.1 | 2.3 | 3.0 | 0.7 | 6.8 | 0.2 | 6.6 | 3.0 | 3.1 | 4.9 | 0.7 | 0.2 | 1.6 | 2.2 | 1.6 | 1.4 |

| | Example | | | | | |
|---|---|---|---|---|---|---|
| | #70 | #71 | #72 | #73 | #74 | #75 |
| $EC_{50}$ [µM] | 16.1 | 0.6 | 1.8 | 4.4 | 4.3 | 0.1 |

Data of EC$_{50}$ values on STING H232R-variant can be found in table 2b:

| Example | | | | | | | | | | | | | | | | | | | | | | | |
|---|---|---|---|---|---|---|---|---|---|---|---|---|---|---|---|---|---|---|---|---|---|---|---|
| #1 | #2 | #5 | #7 | #9 | #10 | #12 | #15 | #17 | #18 | #22 | #24 | #26 | #29 | #51 | #53 | #54 | #55 | #56 | #57 | #59 | #61 | #64 | #65 |
| EC$_{50}$ [µM] 0.2 | 0.09 | 0.5 | 0.2 | 0.1 | 0.4 | 0.4 | 0.2 | 2.1 | 0.2 | 0.1 | 2.0 | 0.2 | 0.2 | 0.05 | 0.7 | 0.3 | 0.8 | 0.4 | 0.2 | 0.1 | 2.9 | 0.2 | 0.1 |

| Example | | | | | |
|---|---|---|---|---|---|
| #66 | #67 | #68 | #69 | #72 | #75 |
| EC$_{50}$ [µM] 0.3 | 0.7 | 0.7 | 0.3 | 0.6 | 0.03 |

Data of EC$_{50}$ values on STING R232H-variant can be found in table 2c:

| Example | | | | | | | | | | | | | | | | | | | | | | | |
|---|---|---|---|---|---|---|---|---|---|---|---|---|---|---|---|---|---|---|---|---|---|---|---|
| #1 | #2 | #5 | #7 | #9 | #10 | #12 | #15 | #17 | #18 | #22 | #24 | #26 | #29 | #51 | #53 | #55 | #56 | #57 | #59 | #61 | #64 | #65 | #66 |
| EC$_{50}$ [µM] 0.2 | 0.05 | 1.0 | 0.2 | 0.2 | 0.5 | 0.6 | 0.2 | 2.0 | 0.2 | 0.2 | 2.3 | 0.2 | 0.6 | 0.05 | 0.7 | 0.7 | 0.8 | 0.2 | 0.1 | 2.9 | 0.6 | 0.1 | 0.2 |

| Example | | | | |
|---|---|---|---|---|
| #67 | #68 | #69 | #72 | #75 |
| EC$_{50}$ [µM] 0.8 | 0.7 | 0.3 | 0.3 | 0.05 |

Data of EC$_{50}$ values on STING R293Q-variant can be found in table 2d:

| Example | | | | | | | | | | | | | | | | | | | | | | | |
|---|---|---|---|---|---|---|---|---|---|---|---|---|---|---|---|---|---|---|---|---|---|---|---|
| #1 | #2 | #5 | #7 | #9 | #10 | #12 | #15 | #17 | #18 | #22 | #24 | #26 | #29 | #51 | #53 | #55 | #56 | #57 | #59 | #61 | #64 | #65 | #66 |
| EC$_{50}$ [µM] 0.4 | 0.4 | 1.2 | 0.7 | 0.6 | 2.1 | 2.1 | 0.7 | 6.1 | 0.7 | 0.7 | 2.2 | 0.6 | 0.6 | 0.3 | 1.6 | 1.7 | 2.2 | 0.6 | 0.2 | 2.2 | 0.5 | 0.1 | 0.7 |

| Example | | | | |
|---|---|---|---|---|
| #67 | #68 | #69 | #72 | #75 |
| EC$_{50}$ [µM] 2.1 | 0.8 | 0.7 | 0.7 | 0.1 |

Data of EC$_{50}$ values on STING AQ-variant can be found in table 2e:

| Example | | | | | | | | | | | | | | | | | | | | | | | | | |
|---|---|---|---|---|---|---|---|---|---|---|---|---|---|---|---|---|---|---|---|---|---|---|---|---|---|
| #1 | #2 | #7 | #9 | #10 | #15 | #17 | #18 | #22 | #26 | #29 | #51 | #53 | #54 | #55 | #56 | #57 | #59 | #61 | #65 | #66 | #67 | #68 | #69 | #72 | #75 |
| EC$_{50}$ [µM] 0.2 | 0.2 | 0.6 | 0.7 | 2.2 | 0.7 | 5.7 | 0.6 | 0.7 | 0.7 | 0.7 | 0.2 | 1.9 | 5.3 | 1.2 | 2.1 | 0.3 | 0.1 | 3.0 | 0.1 | 0.8 | 2.3 | 0.8 | 0.7 | 0.8 | 0.1 |

Cellular Permeability Measurements

Caco-2 cells were obtained from Leibniz Institute DSMZ-German Collection of Microorganisms and Cell Cultures (Braunschweig, Germany) and cultured in DMEM (Dulbecco's modified Eagle medium) containing (in final concentrations) 10% FCS (fetal calf serum), 1% NEAA (non-essential amino acids), 2 mM Glutamin, 100 U/mL Penicillin and 100 µg/mL Streptomycin. Caco-2 cells were seeded either onto 24-well Transwell inserts (Corning, #3379) for bidirectional permeability assays at a density of 160,000 cells/cm² and cultured for 3 weeks, with media change on every second day.

For bidirectional permeability assays 10 mM DMSO stock solutions were diluted in transport buffer (final concentrations: 128.13 mM NaCl, 5.36 mM KCl, 1 mM MgSO$_4$, 1.8 mM CaCl$_2$, 4.17 mM NaHCO$_3$, 1.19 mM Na2HPO$_4$, 0.41 mM NaH$_2$PO$_4$, 15 mM 2-[4-(2-hydroxyethyl)piperazin-1-yl]ethanesulfonic acid (HEPES), 20 mM glucose, pH 7.4) containing 0.25% bovine serum albumin to a final concentration of 10 µM of the test compounds and added to the apical or basal compartment. Cells were incubated with the compounds for up to 2 h. Samples from the opposite compartment were taken at different timepoints.

Compound concentrations in the compartments were quantified using a RapidFire-based high-throughput HPLC/MS/MS system (high performance liquid chromatography/mass spectrometry; Bio-Cius) that was customized to a fully automated and flexible platform, termed RIAS. In this modified setup, the sample was aspirated by a vacuum pump into a 10 µL sample loop for 250 ms and flushed onto a C4 cartridge (3.8 µL bed volume; Bio-Cius) with the aqueous mobile phase (99.9% water, 0.09% formic acid, and 0.01% TFA; flow rate 1.5 mL/min). Prior to bioanalysis samples were spiked with internal standard solution and diluted with acetonitrile (ACN) for protein precipitation. Measurement was operated in multiplereaction monitoring (MRM) mode. Quantification was performed using external calibration. A solid-phase extraction step retained the analyte for 3000 ms while interfering matrix (e.g., buffer components) was removed. With a simple step gradient, the analyte was back-eluted from the cartridge for 3,000 ms with the organic mobile phase (99.9% acetonitrile/methanol [1:1, v:v], 0.09% formic acid, and 0.01% TFA) and flushed into the mass spectrometer at a flow rate of 1.25 mL/min. Afterwards, the cartridge was re-equilibrated with the aqueous mobile phase for 500 ms (flow rate 1.5 mL/min). The RapidFire software and a customized control software were obtained from Bio-Cius. QuickQuan 2.3, Xcalibur 2.0.7, and XDK 2.1.0.25 were used to operate the TSQ Vantage mass spectrometer (ThermoFisher, San Jose, Calif.) integrated to the RapidFire system. Mass spectral data-processing software QuickCalc 7.1.9 was purchased from ThermoFisher. The Master software for the RIAS was programmed in-house using LabVIEW (version 8.6.1; National Instruments, Austin, Tex.). Data analysis was performed in AssayExplorer 3.2 (Symyx, Sunnyvale, Calif.), and correlation plots were visualized in Spotfire version 2.2.0 (TIBCO, Palo Alto, Calif.).

Apparent permeability coefficients in the apical to basal direction ($P_{app,AB}$) and in the basal to apical direction ($P_{app,BA}$) and efflux ratios were calculated as follows:

$$P_{app,AB} = Q_{AB}/(C_0 \cdot s \cdot t)$$

$$P_{app,BA} = Q_{BA}/(C_0 \cdot s \cdot t)$$

$$\text{Efflux ratio} = P_{app,BA}/P_{app,AB}$$

where Q is the amount of compound recovered in the receiver compartment after the incubation time t, $C_0$ the initial compound concentration given to the donor compartment, and s the surface area of the Transwell inserts. As quality controls, one reference P-gp substrate (apafant) and one low permeable compound (BI internal reference, $P_{app} \sim 3 \cdot 10^{-7}$ cm/s, no efflux) is included in every assay plate. In addition, transepithelial electrical resistance (TEER) values are measured for each plate before the permeability assay, and total recovery in donor and receiver compartments was determined for each compound. Results can be seen in tables 3a and 3b.

TABLE 3a

Cellular permeability measurements—$P_{app,AB}$:

| | #2 | #6 | #7 | #9 | #10 | #11 | #12 | #14 | #15 | #17 | #18 | #21 | #22 | #27 | #30 | #53 | #54 | #55 | #56 | #57 | #59 | #62 | #63 | #60 |
|---|---|---|---|---|---|---|---|---|---|---|---|---|---|---|---|---|---|---|---|---|---|---|---|---|
| Caco A → B [$10^{-6}$ cm/s] | 20 | 39 | 28 | 23 | 26 | 27 | 11 | 39 | 26 | 26 | 36 | 23 | 10 | 32 | 14 | 50 | 38 | 21 | 21 | 15 | 11 | 11 | 19 | 19 |

| | #61 | #67 | #68 | #69 | #70 | #75 |
|---|---|---|---|---|---|---|
| Caco A → B [$10^{-6}$ cm/s] | 10 | 16 | 16 | 14 | 18 | 9 |

Cellular Permeability Measurements—Efflux Ratio:

| Example | #1 | #2 | #3 | #6 | #7 | #9 | #11 | #12 | #14 | #15 | #17 | #18 | #20 | #21 | #22 | #27 | #30 | #31 | #52 | #53 | #54 | #55 | #56 | #57 |
|---|---|---|---|---|---|---|---|---|---|---|---|---|---|---|---|---|---|---|---|---|---|---|---|---|
| Efflux ratio | 0.4 | 0.6 | 0.6 | 0.4 | 0.6 | 0.3 | 0.3 | 0.4 | 0.3 | 0.5 | 0.3 | 0.3 | 0.8 | 0.3 | 1.6 | 0.5 | 0.9 | 0.6 | 0.4 | 0.2 | 0.8 | 1.0 | 0.6 | 1.2 |

| Example | #59 | #60 | #61 | #62 | #63 | #67 | #68 | #69 | #70 | #73 | #75 |
|---|---|---|---|---|---|---|---|---|---|---|---|
| Efflux ratio | 2.5 | 0.9 | 1.1 | 1.2 | 0.6 | 1.2 | 1.0 | 1 | 1.2 | 0.5 | 4.8 |

Solubility Measurements

Aqueous solubilities were determined from 10 mM stock solutions of the compounds in DMSO diluted to a final concentration of 250 μM with aqueous McIlvaine buffer at pH 6.8, or with acetonitrile/water (1:1) as a reference. Samples were shaken for 24 h at room temperature in 96-well plates (Whatman Uniplate® 96 wells, 750 μL, polypropylene, round bottom). The plate was then centrifuged at 3,000 rpm for 2 min. 250 μL of each sample were transferred to a Millipore MultiScreenHTS filter plate with a polycarbonate membrane, pore size 0.45 μm. Filtrates were collected by centrifugation at 3,000 rpm for 2 min. The dissolved concentrations were determined by UPLC/UV (Ultra-Performance Liquid Chromatography/ultraviolet) on a Waters ACQUITY UPLC® SQD system equipped with a Waters ACQUITY UPLC® BEH 2.1×50 mm C18 column, particle size 1.7 μm, using a short gradient with water/0.1% formic acid as solvent A and acetonitrile/0.1% formic acid as solvent B (5 to 95% B with 1.7 min total cycle time). Compounds signals were measured with a photodiode array UV detector operated at 254 nm. Solubilities were determined with a one point calibration by comparing peak areas relative to the reference standard using Waters Empower software. Results can be found in Table 4.

TABLE 4

Solubility in HTS at pH 6.8

| Example | | | | | |
|---|---|---|---|---|---|
| | #19 | #26 | #28 | #29 | #30 |
| Soblubility [μg/ml] | 51 | 60 | 87 | 63 | 42 |

| Example | | | | | |
|---|---|---|---|---|---|
| | #57 | #58 | #59 | #62 | #63 |
| Soblubility [μg/ml] | 80 | 84 | 66 | 49 | 75 |

| Example | | | | |
|---|---|---|---|---|
| | #67 | #69 | #70 | #71 |
| Soblubility [μg/ml] | 82 | 70 | 74 | 67 |

What we claim:
1. A compound of formula (I)

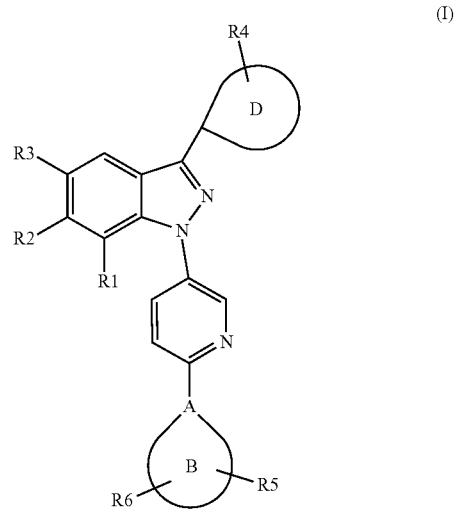

Wherein
A is N or C,
B is a group selected from among the group consisting of
a 5-7-membered monocyclic heterocyclyl containing 1 or 2 N-atoms,
a 6-membered bicyclic heterocyclyl containing 1 N-atom,
a 7-11 membered bicyclic heterocyclyl containing 2 N-atoms,
a 7-membered bicyclic heterocyclyl containing 1 N-atom and 1 O-atom,
a 6-membered monocyclic heterocyclyl containing 1 N-atom and 1 heteroatom selected from the group consisting of O and S,
a 9-membered bicyclic heterocyclyl containing 3 heteroatoms, 2 of which are N and the other is O,
a 9-membered bicyclic heterocyclyl containing 1 N-atom and 1 S-atom,
a 10-membered bicyclic heterocyclyl containing 3 N-atoms, 2 of which are substituted with $C_{1-6}$-alkyl,
phenyl,
a 9-membered bicyclic heteroaryl containing 3 N-atoms,
—$C_{1-4}$-alkylene-pyrimidine, and
—$C_{1-4}$-alkylene-O—$C_{1-3}$-alkyl;
D is a group selected from among the group consisting of
a 9-membered bicyclic heteroaryl containing 2 N-atoms,
a 10-membered bicyclic heteroaryl containing 1 N-atom, and benzodioxole;
$R^1$ is selected from among the group consisting of —H, —$C_{1-6}$-alkyl, —$CF_3$, —$C_{2-6}$-alkynyl, —O—$C_{1-6}$-alkyl and halogen;
$R^2$ is selected from among the group consisting of —H, —$C_{1-6}$-alkyl, —$C_{1-6}$-alkylene-OH, —C(O)OH, —C(O)O—$C_{1-6}$-alkyl and -pyrazolyl-$C_{1-6}$-alkyl;
$R^3$ is —H or —$C_{1-6}$-alkyl;
$R^4$ is selected from among the group consisting of —H, —$C_{1-3}$-alkyl, —$NH_2$, —$NHC_{1-3}$-alkyl and $N(C_{1-3}$-alkyl$)_2$;
$R^5$ is absent or is selected from among the group consisting of —H, —$C_{1-6}$-alkyl, —$S(O_2)$—$C_{1-6}$-alkyl, —NH—$S(O_2)$—$C_{1-6}$-alkyl, =O, —C(O)—$C_{1-6}$-alkyl, —C(O)H, —C(O)OH, —C(O)$NH_2$, —C(O)O—$C_{1-6}$-alkyl, —$NR^{5.1}R^{5.2}$, —$C_{1-6}$-alkylene-C(O)OH, —S(O$_2$)—NH$_2$, -pyrolidin-2-one-1-yl, -tetrazolyl, and a 5-membered heteroaryl with 1 or 2 heteroatoms selected from the group consisting of N and O, substituted with R$^{5.3}$;

R$^{5.1}$ is selected from among the group consisting of —H, —C$_{1-6}$-alkyl, —C(O)—C$_{1-6}$-alkyl and —C$_{1-6}$-alkylene-O—C$_{1-6}$-alkyl;

R$^{5.2}$ is selected from among the group consisting of —H, —C$_{1-6}$-alkyl, —C(O)—C$_{1-6}$-alkyl, —C$_{1-6}$-alkylene-O—C$_{1-6}$-alkyl and —C$_{1-6}$-alkylene-R$^{5.3}$;

R$^{5.3}$ is selected from among the group consisting of —H, —C$_{1-6}$-alkyl and a 6-membered heteroaryl with 1 or 2 heteroatoms selected from a group consisting of N and O;

R$^6$ is absent or is selected from among the group consisting of —H, —C$_{1-6}$-alkyl, =O and —C(O)OH;

or a salt thereof.

2. A compound according to claim 1, wherein

R$^1$ is selected from among the group consisting of —C$_{1-6}$-alkyl, —CF$_3$, —O—C$_{1-6}$-alkyl and halogen;

R$^4$ is —H or —C$_{1-3}$-alkyl;

or a salt thereof.

3. A compound according to claim 1, wherein

D is selected from among the group consisting of

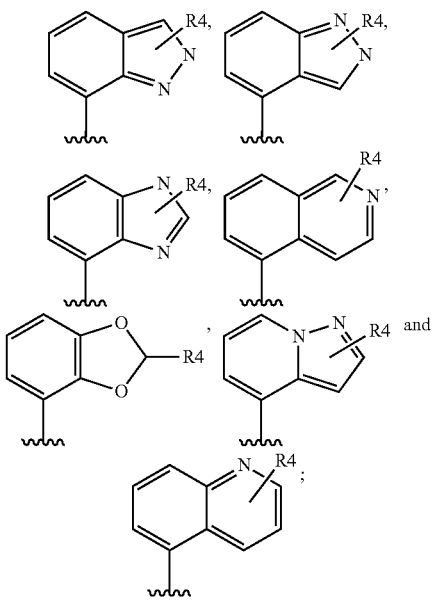

R$^1$ is selected from among the group consisting of —C$_{1-6}$-alkyl, —CF$_3$, —O—C$_{1-6}$-alkyl, —Br and —Cl;

R$^2$ is —H;

R$^3$ is —H;

or a salt thereof.

4. A compound according to claim 1, wherein

D is selected from among the group consisting of

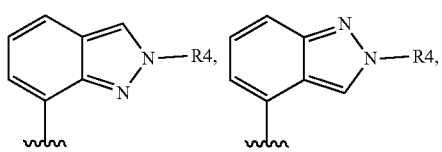

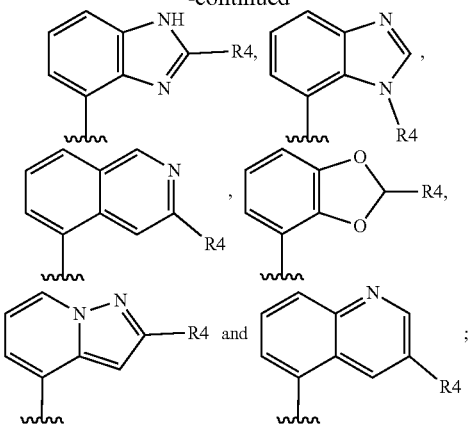

or a salt thereof.

5. A compound according to claim 1, wherein

D is selected from among the group consisting of

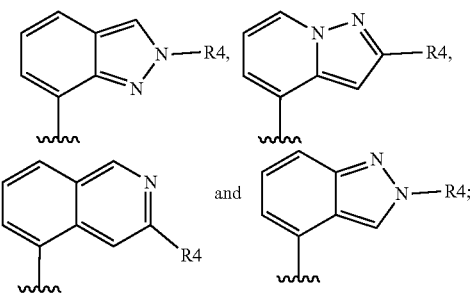

or a salt thereof.

6. A compound according to claim 1, wherein

R$^5$ is selected from among the group consisting of —H, —C$_{1-6}$-alkyl, —S(O$_2$)—C$_{1-6}$-alkyl, =O, —C(O)H, —C(O)NH$_2$, —C(O)OH, —C(O)O—C$_{1-6}$-alkyl, —NR$^{5.1}$R$^{5.2}$ and a 5-membered heteroaryl with 1 or 2 heteroatoms selected from a group consisting of N and O, substituted with R$^{5.3}$;

R$^{5.1}$ is selected from among the group consisting of —H, —C$_{1-6}$-alkyl, —C(O)—C$_{1-6}$-alkyl and —C$_{1-6}$-alkylene-O—C$_{1-6}$-alkyl;

R$^{5.2}$ is selected from among the group consisting of —H, —C$_{1-6}$-alkyl, —C(O)—C$_{1-6}$-alkyl, —C$_{1-6}$-alkylene-O—C$_{1-6}$-alkyl and —C$_{1-6}$-alkyl-R$^{5.3}$;

R$^{5.3}$ is —H or —C$_{1-6}$-alkyl;

or a salt thereof.

7. A compound according to claim 1, wherein B is selected from among the group consisting of

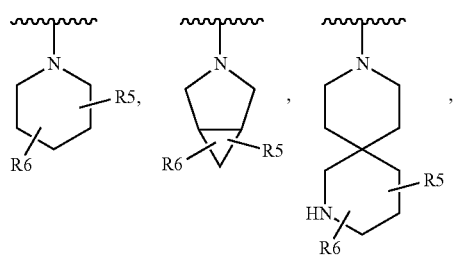

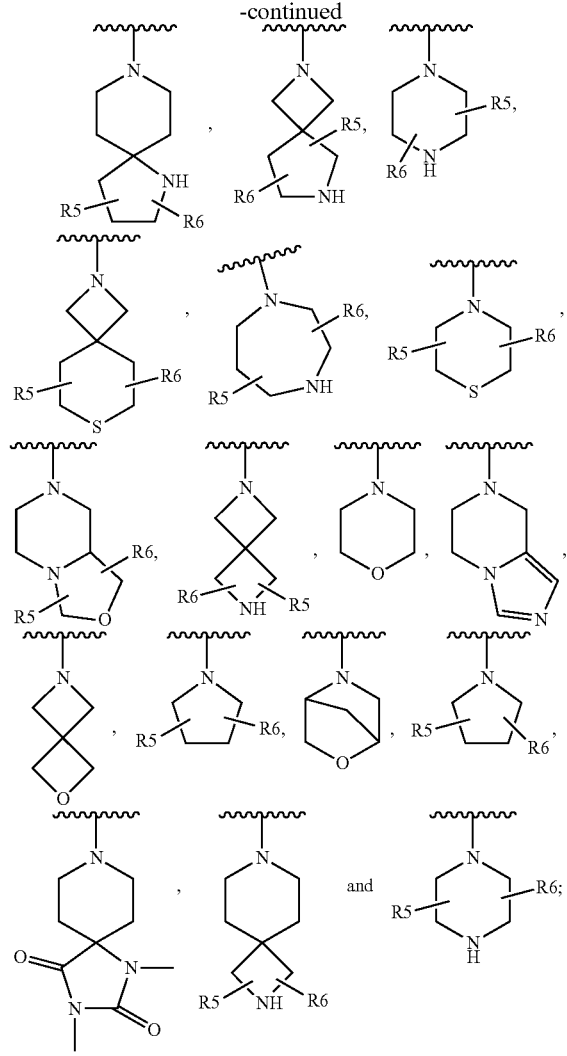
or a salt thereof.
8. A compound according to claim 1, wherein B is selected from among the group consisting of
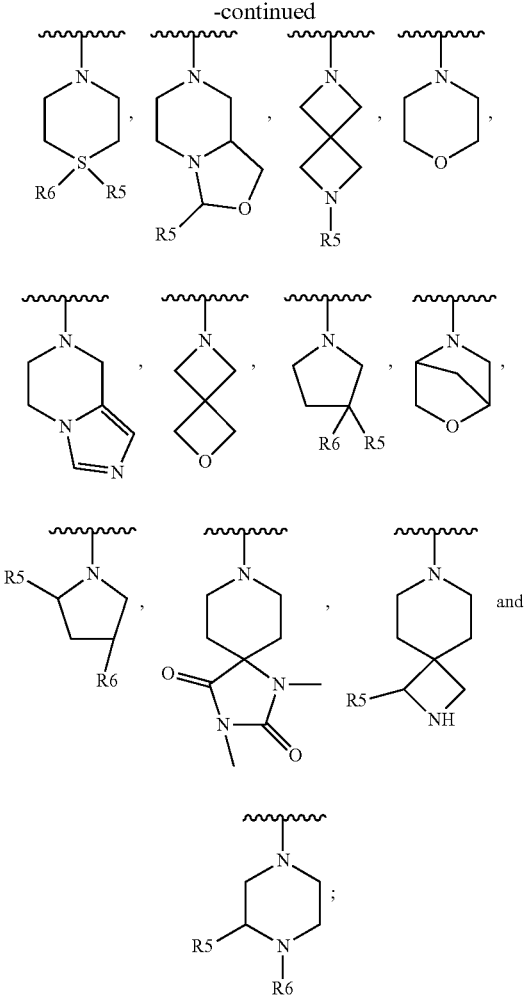
or a salt thereof.
9. A compound according to claim 1, wherein B is selected from among the group consisting of
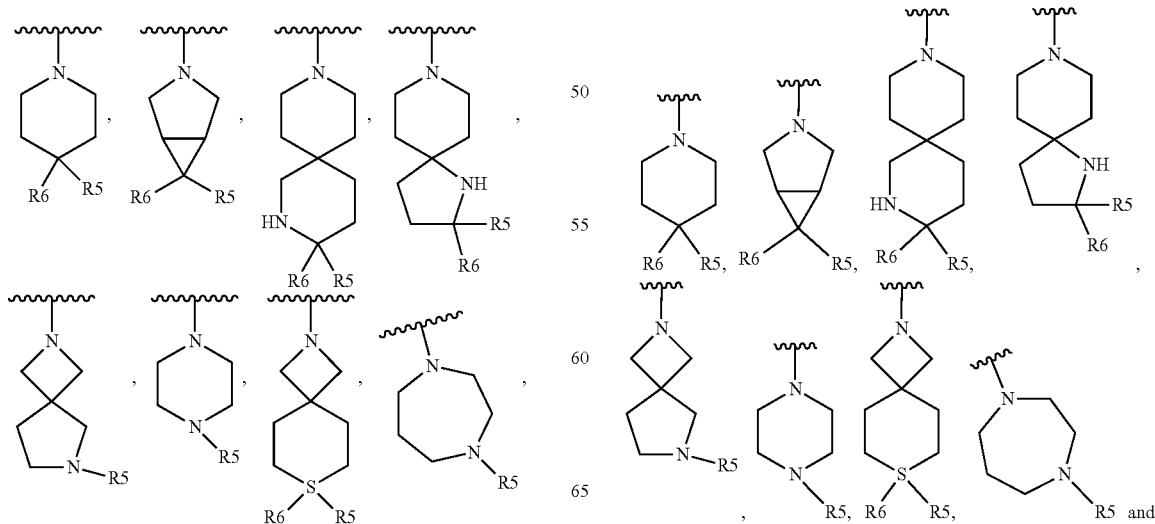

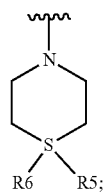
or a salt thereof.
10. A compound according to claim 1, selected from the group consisting of
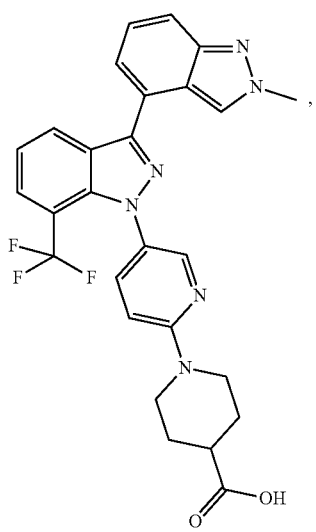
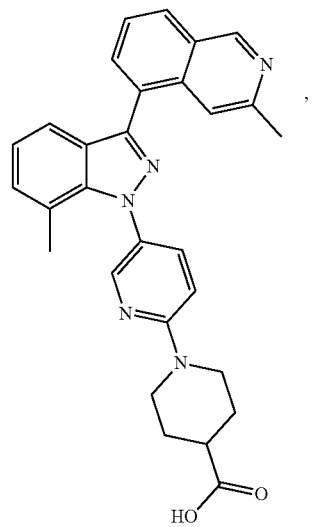
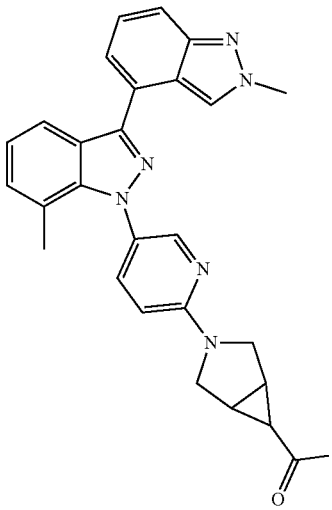
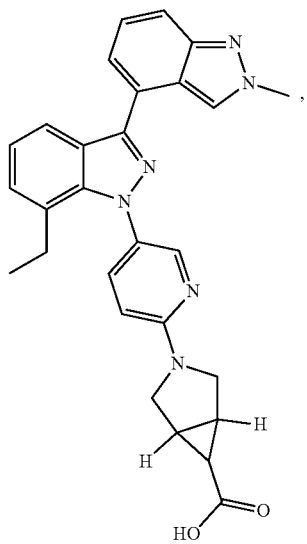
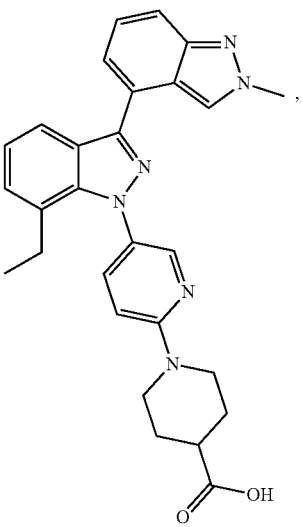

159
-continued
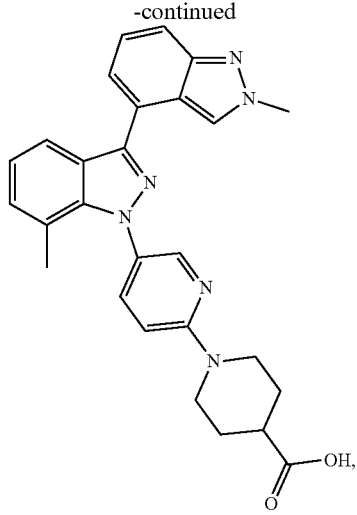
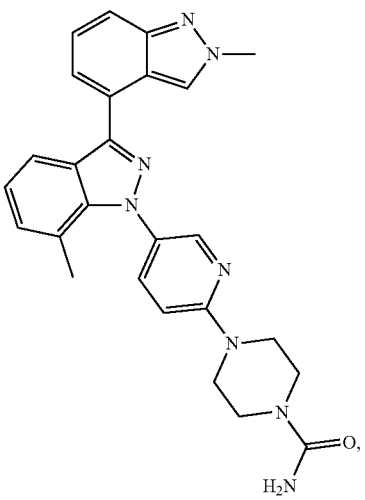
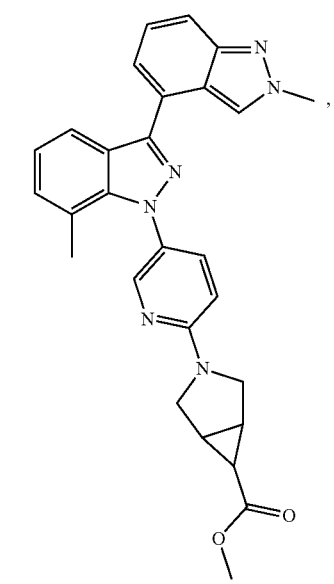
160
-continued
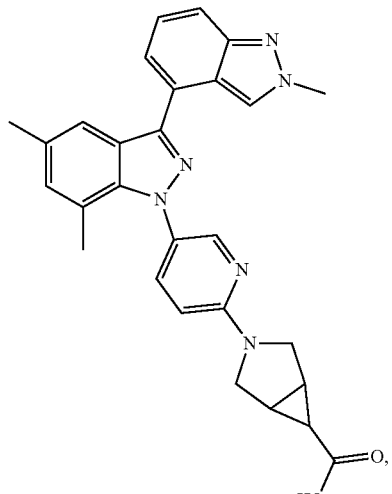
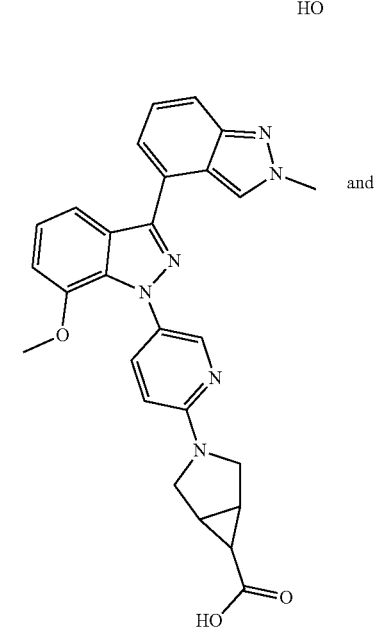
and
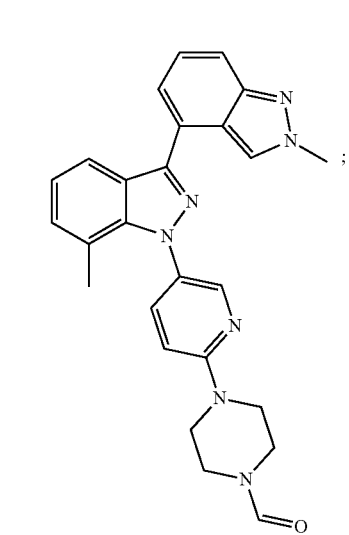
or a pharmaceutically acceptable salt thereof.

11. A compound according to claim 1 in its salt free form.

12. A method for treating a disease selected from among the group consisting of inflammation, allergic and autoimmune diseases, infectious diseases and cancer in a patient comprising administering to the patient a therapeutically effective amount of a compound according to claim 1 or a pharmaceutically acceptable salt thereof.

13. A method according to claim 12, wherein the disease to be treated is cancer and wherein the compound is administered after radiotherapy.

14. A method of stimulating an immune response in a patient to one or more predetermined antigens comprising administering to the patient a compound according to claim 1, or a pharmaceutically acceptable salt thereof, as a vaccine adjuvant together with, or in addition to, one or more vaccines.

15. A pharmaceutical composition comprising at least one compound according to claim 1, or a pharmaceutically acceptable salt thereof, and a pharmaceutically acceptable carrier.

16. A pharmaceutical composition comprising one or more compounds according to claim 1, or a pharmaceutically acceptable salt thereof, and an active substance selected from the group consisting of cytostatic substances, cytotoxic substances, cell proliferation inhibitors, anti-angiogenic substances, steroids, viruses, immunogenic cell death inducers, cancer targeting agents, immuno-modulating agents, antibodies and nanobodies.

17. A compound having the following structure:

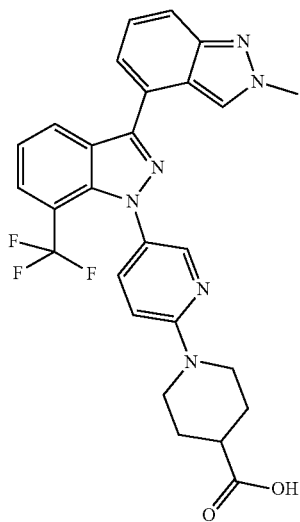 [SMILES: Cn1cc2c(-c3nn(-c4ccc(N5CCC(C(=O)O)CC5)nc4)c4c(C(F)(F)F)cccc34)cccc2n1]

or a pharmaceutically acceptable salt thereof.

18. A compound having the following structure:

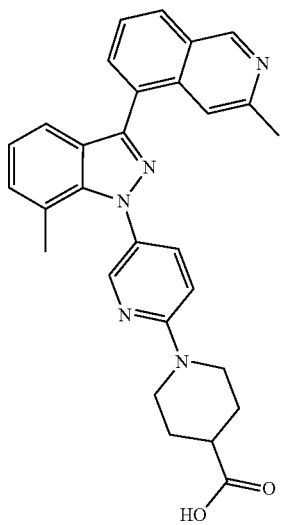 [SMILES: Cc1cc2c(-c3nn(-c4ccc(N5CCC(C(=O)O)CC5)nc4)c4c(C)cccc34)cccc2cn1]

or a pharmaceutically acceptable salt thereof.

19. A compound having the following structure:

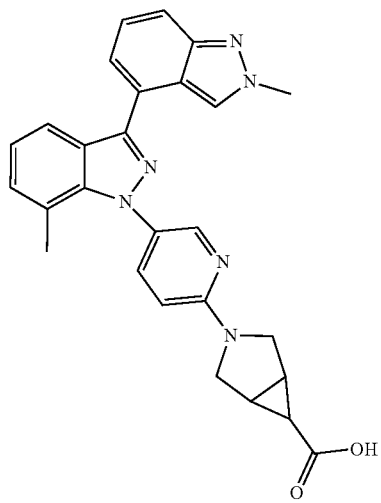 [SMILES: Cc1cccc2c(-c3cccc4nn(C)cc34)nn(-c3ccc(N4CC5C(C4)C5C(=O)O)nc3)c12]

or a pharmaceutically acceptable salt thereof.

20. A compound having the following structure:

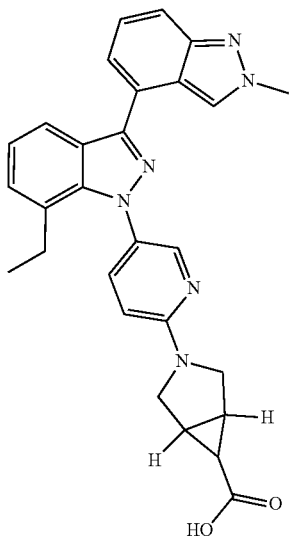 [SMILES: CCc1cccc2c(-c3cccc4nn(C)cc34)nn(-c3ccc(N4CC5C(C4)C5C(=O)O)nc3)c12]

or a pharmaceutically acceptable salt thereof.

21. A compound having the following structure:

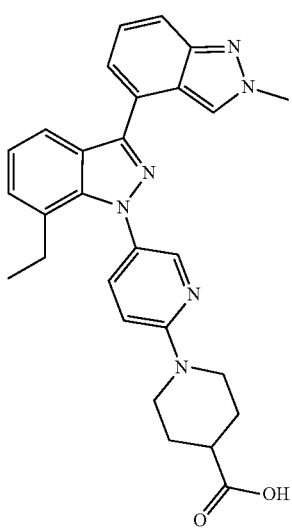 [SMILES: CCc1cccc2c(-c3cccc4nn(C)cc34)nn(-c3ccc(N4CCC(C(=O)O)CC4)nc3)c12]

or a pharmaceutically acceptable salt thereof.

22. A compound having the following structure:

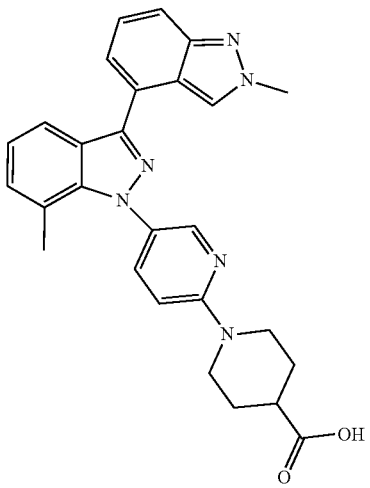 [SMILES: Cc1cccc2c(-c3cccc4nn(C)cc34)nn(-c3ccc(N4CCC(C(=O)O)CC4)nc3)c12]

or a pharmaceutically acceptable salt thereof.

23. A compound having the following structure:

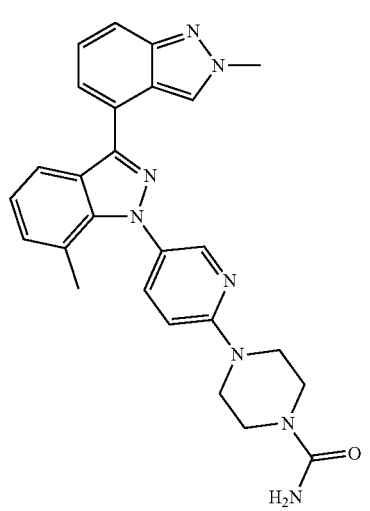 [SMILES: Cc1cccc2c(-c3cccc4nn(C)cc34)nn(-c3ccc(N4CCN(C(N)=O)CC4)nc3)c12]

or a pharmaceutically acceptable salt thereof.

24. A compound having the following structure:

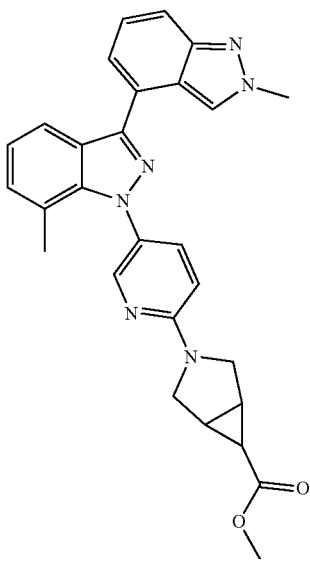 [SMILES: COC(=O)C1C2CN(c3ccc(-n4nc(-c5cccc6nn(C)cc56)c5cccc(C)c54)cn3)CC21]

or a pharmaceutically acceptable salt thereof.

25. A compound having the following structure:

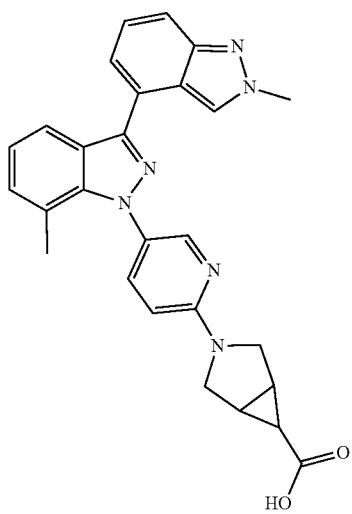 [SMILES: Cc1cccc2c(-c3cccc4nn(C)cc34)nn(-c3ccc(N4CC5C(C4)C5C(=O)O)nc3)c12]

or a pharmaceutically acceptable salt thereof.

26. A compound having the following structure:

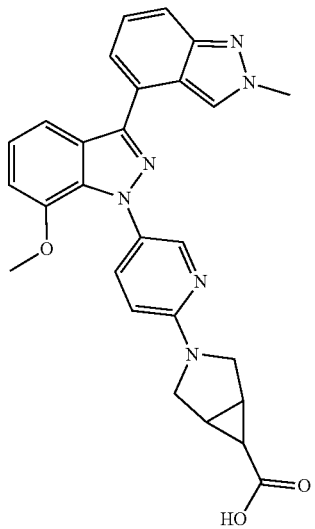 [SMILES: COc1cccc2c(-c3cccc4nn(C)cc34)nn(-c3ccc(N4CC5C(C4)C5C(=O)O)nc3)c12]

or a pharmaceutically acceptable salt thereof.

27. A compound having the following structure:

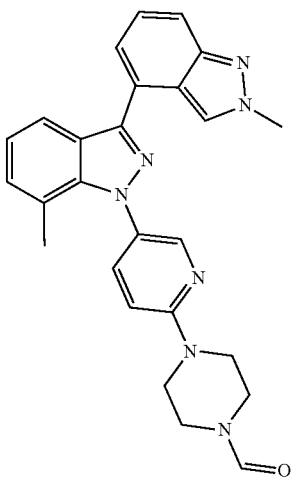 [SMILES: Cc1cccc2c(-c3cccc4nn(C)cc34)nn(-c3ccc(N4CCN(C=O)CC4)nc3)c12]

or a pharmaceutically acceptable salt thereof.

28. A compound having the following structure:
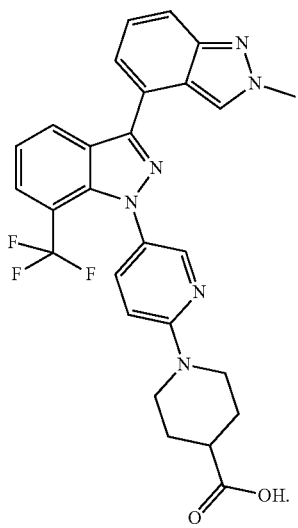 [SMILES: Cn1cc2c(-c3nn(-c4ccc(N5CCC(C(=O)O)CC5)nc4)c4c(C(F)(F)F)cccc34)cccc2n1]
29. A compound having the following structure:
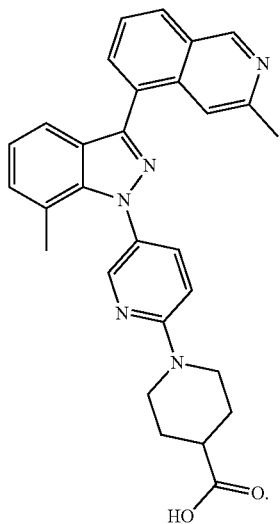 [SMILES: Cc1cc2c(-c3nn(-c4ccc(N5CCC(C(=O)O)CC5)nc4)c4c(C)cccc34)cccc2cn1]
30. A compound having the following structure:
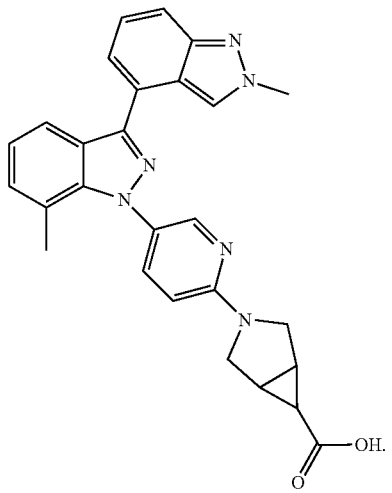 [SMILES: Cc1cccc2c(-c3cccc4nn(C)cc34)nn(-c3ccc(N4CC5C(C4)C5C(=O)O)nc3)c12]
31. A compound having the following structure:
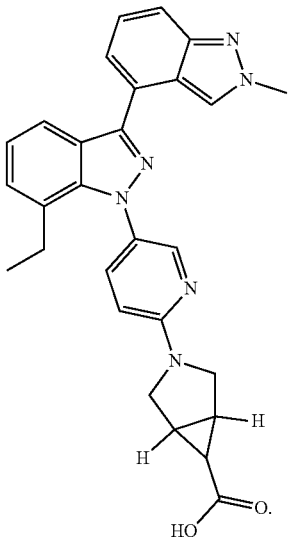 [SMILES: CCc1cccc2c(-c3cccc4nn(C)cc34)nn(-c3ccc(N4CC5C(C4)C5C(=O)O)nc3)c12]

32. A compound having the following structure:
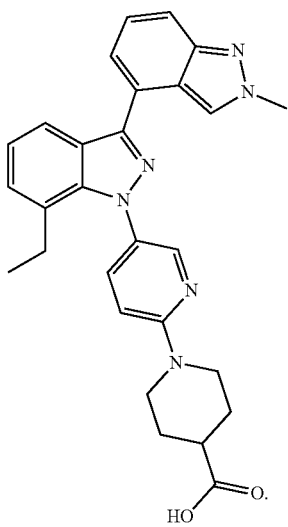 [SMILES: CCc1cccc2c(-c3cccc4nn(C)cc34)nn(-c3ccc(N4CCC(C(=O)O)CC4)nc3)c12]
33. A compound having the following structure:
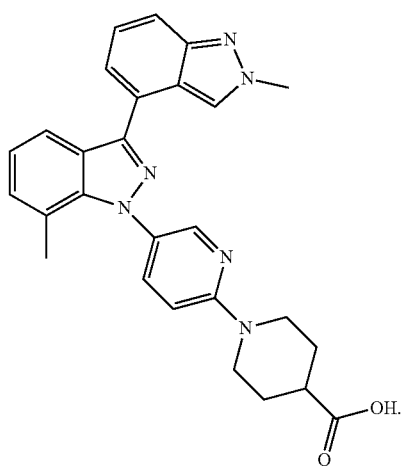 [SMILES: Cc1cccc2c(-c3cccc4nn(C)cc34)nn(-c3ccc(N4CCC(C(=O)O)CC4)nc3)c12]
34. A compound having the following structure:
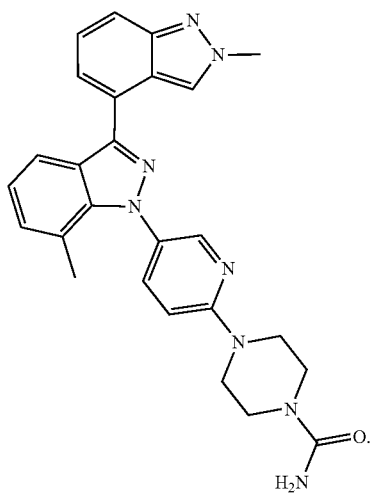 [SMILES: Cc1cccc2c(-c3cccc4nn(C)cc34)nn(-c3ccc(N4CCN(C(N)=O)CC4)nc3)c12]
35. A compound having the following structure:
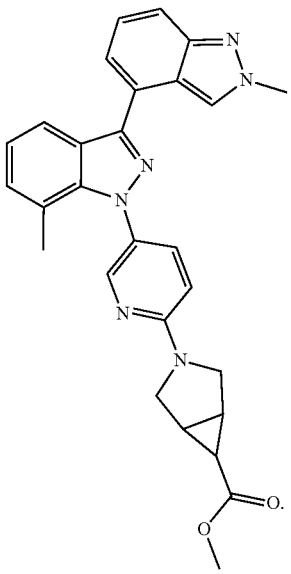 [SMILES: COC(=O)C1C2CN(c3ccc(-n4nc(-c5cccc6nn(C)cc56)c5cccc(C)c54)cn3)CC21]
36. A compound having the following structure:
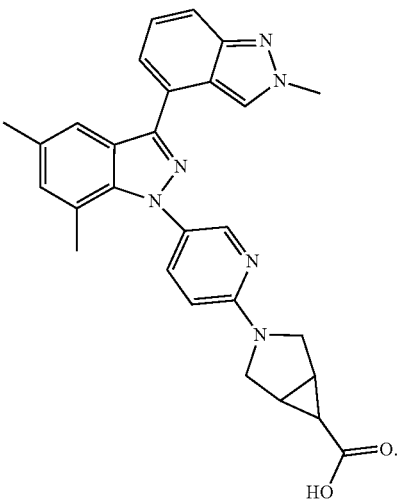 [SMILES: Cc1cc(C)c2c(c1)c(-c1cccc3nn(C)cc13)nn2-c1ccc(N2CC3C(C2)C3C(=O)O)nc1]

37. A compound having the following structure:
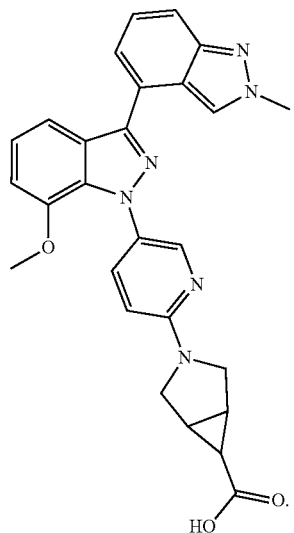
38. A compound having the following structure:
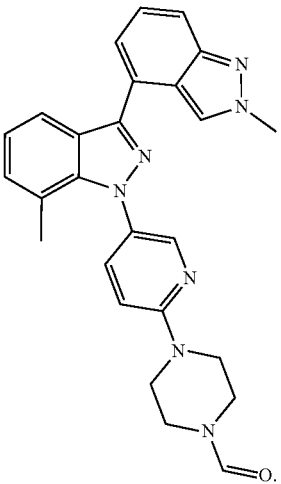 [SMILES: Cc1cccc2c(-c3cccc4nn(C)cc34)nn(-c3ccc(N4CCN(C=O)CC4)nc3)c12]
39. A method according to claim 12, wherein the disease to be treated is non-small cell lung cancer.
40. A method according to claim 13, wherein the disease to be treated is non-small cell lung cancer.
* * * * *